(12) United States Patent
Deisseroth et al.

(10) Patent No.: US 10,974,064 B2
(45) Date of Patent: Apr. 13, 2021

(54) OPTOGENETIC CONTROL OF BEHAVIORAL STATE

(71) Applicant: The Board of Trustees of the Leland Stanford Junior University, Stanford, CA (US)

(72) Inventors: Karl Deisseroth, Stanford, CA (US); Sung-Yon Kim, Cambridge, MA (US); Avishek Adhikari, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 247 days.

(21) Appl. No.: 14/776,513

(22) PCT Filed: Mar. 14, 2014

(86) PCT No.: PCT/US2014/028807
§ 371 (c)(1),
(2) Date: Sep. 14, 2015

(87) PCT Pub. No.: WO2014/144409
PCT Pub. Date: Sep. 18, 2014

(65) Prior Publication Data
US 2016/0038764 A1     Feb. 11, 2016

Related U.S. Application Data

(60) Provisional application No. 61/789,961, filed on Mar. 15, 2013, provisional application No. 61/808,965, filed on Apr. 5, 2013.

(51) Int. Cl.
| | |
|---|---|
| *A61K 41/00* | (2020.01) |
| *A61N 5/06* | (2006.01) |
| *A61K 48/00* | (2006.01) |
| *C12N 15/86* | (2006.01) |
| *A61K 31/00* | (2006.01) |
| *A61K 45/00* | (2006.01) |
| *A61N 1/36* | (2006.01) |

(52) U.S. Cl.
CPC ............ *A61N 5/0618* (2013.01); *A61K 31/00* (2013.01); *A61K 41/00* (2013.01); *A61K 45/00* (2013.01); *A61N 5/0622* (2013.01); *A61N 1/36121* (2013.01); *A61N 5/062* (2013.01); *A61N 2005/0612* (2013.01); *A61N 2005/0663* (2013.01)

(58) Field of Classification Search
CPC .. A61N 5/062; A61N 5/0622; A61N 1/36121; A61N 5/0618; A61K 41/00; A61K 45/00; A61K 31/00; A61K 48/00; A61K 48/0058; A61P 25/22; A61P 43/00; C12N 1515/86
See application file for complete search history.

(56) References Cited

U.S. PATENT DOCUMENTS

| | | |
|---|---|---|
| 2,968,302 A | 1/1961 | Fry et al. |
| 3,131,690 A | 5/1964 | Innis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |

(Continued)

FOREIGN PATENT DOCUMENTS

| | | |
|---|---|---|
| CN | 1079464 A | 12/1993 |
| CN | 1558222 A | 12/2004 |

(Continued)

OTHER PUBLICATIONS

Hammack et al Prog Neuropsychopharmacol Biol Psychiatry. 33(8): 1309-1320 (Year: 2009).*
Soofiyani et al Advanced Pharmaceutical Bulletin,3(2), 249-255 (Year: 2013).*
Williams and Denison Sci. Transl. Med., 5,177ps6 , 1-4 (Year: 2013).*
Kim et al Nature, 496, 219-223 (Year: 2013).*
Gradinaru et al The Journal of Neuroscience, 727(52):14231-14238 (Year: 2007).*
Kaiser Science, 317, 580 (Year: 2007).*
Kay et al Nature Reviews Genetics 12, 316-328 (Year: 2011).*

(Continued)

*Primary Examiner* — Anoop K Singh
(74) *Attorney, Agent, or Firm* — Paula A. Borden; Rudy J. Ng; Bozicevic, Field & Francis LLP

(57) ABSTRACT

The present disclosure provides methods of modulating a feature of a behavioral state. The methods involve inhibiting or activating the activity of a bed nucleus of stria terminalis (BNST) neuron, a BNST subnucleus, or a neuronal output to or from a BNST neuron. Animals encounter environmental conditions that require rapid switching among different behavioral states to increase the likelihood of survival and reproduction.

10 Claims, 35 Drawing Sheets
Specification includes a Sequence Listing.

(56) References Cited

U.S. PATENT DOCUMENTS

| | | |
|---|---|---|
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segal Man et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,289,229 B1 | 9/2001 | Crowley |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischel) et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,716,447 B2 | 5/2014 | Deisseroth et al. |
| 8,729,040 B2 | 5/2014 | Deisseroth et al. |
| 8,815,582 B2 | 8/2014 | Deisseroth et al. |
| 8,834,546 B2 | 9/2014 | Deisseroth et al. |
| 8,864,805 B2 | 10/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 8,956,363 B2 | 2/2015 | Deisseroth et al. |
| 8,962,589 B2 | 2/2015 | Deisseroth et al. |
| 9,057,734 B2 | 6/2015 | Cohen |
| 9,079,940 B2 | 7/2015 | Deisseroth et al. |
| 9,084,885 B2 | 7/2015 | Deisseroth et al. |
| 9,101,690 B2 | 8/2015 | Deisseroth et al. |
| 9,101,759 B2 | 8/2015 | Deisseroth et al. |
| 9,175,095 B2 | 11/2015 | Deisseroth et al. |
| 9,187,745 B2 | 11/2015 | Deisseroth et al. |
| 9,238,150 B2 | 1/2016 | Deisseroth et al. |
| 9,249,200 B2 | 2/2016 | Deisseroth et al. |
| 9,249,234 B2 | 2/2016 | Deisseroth et al. |
| 9,271,674 B2 | 3/2016 | Deisseroth et al. |
| 9,274,099 B2 | 3/2016 | Deisseroth et al. |
| 9,278,159 B2 | 3/2016 | Deisseroth et al. |
| 9,309,296 B2 | 4/2016 | Deisseroth et al. |
| 9,340,589 B2 | 5/2016 | Deisseroth et al. |
| 9,359,449 B2 | 6/2016 | Deisseroth et al. |
| 9,421,258 B2 | 8/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 9,636,380 B2 | 5/2017 | Deisseroth et al. |
| 9,850,290 B2 | 12/2017 | Deisseroth et al. |
| 9,968,652 B2 | 5/2018 | Deisseroth et al. |
| 10,064,912 B2 | 9/2018 | Deisseroth et al. |
| 10,071,132 B2 | 9/2018 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0103949 A1 | 6/2003 | Carpenter et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0260367 A1 | 12/2004 | Taboada et al. |
| 2004/0267118 A1 | 12/2004 | Dawson |
| 2005/0020945 A1 | 1/2005 | Tosaya et al. |
| 2005/0027284 A1 | 2/2005 | Lozano et al. |
| 2005/0058987 A1 | 3/2005 | Shi et al. |
| 2005/0088177 A1 | 4/2005 | Schreck et al. |
| 2005/0102708 A1 | 5/2005 | Lecanu et al. |
| 2005/0107753 A1 | 5/2005 | Rezai et al. |

(56) References Cited

U.S. PATENT DOCUMENTS

| | | |
|---|---|---|
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynsb et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0129126 A1 | 6/2006 | Kaplitt et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0046053 A1 | 1/2008 | Wagner et al. |
| 2008/0033569 A1 | 2/2008 | Ferren et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud et al. |
| 2008/0119421 A1 | 5/2008 | Tuszynsh et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1* | 6/2010 | Vasar ............... A01K 67/0276 800/3 |
| 2010/0190229 A1 | 7/2010 | Zhang et al. |
| 2010/0209352 A1 | 8/2010 | Hultman et al. |
| 2010/0234273 A1 | 9/2010 | Deisseroth et al. |
| 2011/0221970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0233046 A1 | 9/2011 | Nikolenko et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0089503 A1 | 4/2013 | Deisseroth et al. |
| 2013/0144359 A1 | 6/2013 | Kishawi et al. |
| 2013/0284920 A1 | 10/2013 | Deisseroth et al. |
| 2013/0286181 A1 | 10/2013 | Betzig et al. |
| 2013/0288365 A1 | 10/2013 | Deisseroth et al. |
| 2013/0289669 A1 | 10/2013 | Deisseroth et al. |
| 2013/0289675 A1 | 10/2013 | Deisseroth et al. |
| 2013/0296406 A1 | 11/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0082758 A1 | 3/2014 | Deisseroth et al. |
| 2014/0148880 A1 | 5/2014 | Deisseroth et al. |
| 2014/0235826 A1 | 8/2014 | Deisseroth et al. |
| 2014/0271479 A1 | 9/2014 | Lammel et al. |
| 2014/0324133 A1 | 10/2014 | Deisseroth et al. |
| 2015/0040249 A1 | 2/2015 | Deisseroth et al. |
| 2015/0072394 A1 | 3/2015 | Deisseroth et al. |
| 2015/0112411 A1 | 4/2015 | Beckman et al. |
| 2015/0165227 A1 | 6/2015 | Deisseroth et al. |
| 2015/0174244 A1 | 6/2015 | Deisseroth et al. |
| 2015/0217128 A1 | 8/2015 | Deisseroth et al. |
| 2015/0218547 A1 | 8/2015 | Deisseroth et al. |
| 2015/0297719 A1 | 10/2015 | Deisseroth et al. |
| 2016/0002302 A1 | 1/2016 | Deisseroth et al. |
| 2016/0015996 A1 | 1/2016 | Deisseroth et al. |

(56) References Cited

U.S. PATENT DOCUMENTS

| | | |
|---|---|---|
| 2016/0038764 A1 | 2/2016 | Deisseroth et al. |
| 2016/0045599 A1 | 2/2016 | Deisseroth et al. |

FOREIGN PATENT DOCUMENTS

| | | | |
|---|---|---|---|
| CN | 1781019 A | 5/2006 | |
| CN | 102076866 A | 5/2011 | |
| CN | 103313752 A | 9/2013 | |
| CN | 103476456 A | 12/2013 | |
| EP | 1197144 | 4/2002 | |
| EP | 1334748 | 8/2003 | |
| EP | 1444889 | 8/2004 | |
| EP | 1873566 | 1/2008 | |
| JP | 6295350 | 10/1994 | |
| JP | H 09505771 A | 6/1997 | |
| JP | 2004534508 | 11/2004 | |
| JP | 2005034073 A | 2/2005 | |
| JP | 2006217866 | 8/2006 | |
| JP | 2007530027 A | 11/2007 | |
| JP | 2008010422 A | 1/2008 | |
| JP | 2010227537 A | 10/2010 | |
| JP | 2012508581 | 4/2012 | |
| WO | WO 1995/005214 | 2/1995 | |
| WO | WO 1996/032076 | 10/1996 | |
| WO | WO 2000/027293 | 5/2000 | |
| WO | WO 2001/025466 | 4/2001 | |
| WO | WO 2003/016486 | 2/2003 | |
| WO | WO 2003/040323 | 5/2003 | |
| WO | WO 2003/046141 | 6/2003 | |
| WO | WO 2003/084994 | 10/2003 | |
| WO | WO 2003/102156 | 12/2003 | |
| WO | WO 2004/033647 | 4/2004 | |
| WO | WO 2005/093429 | 10/2005 | |
| WO | WO 2006/103678 | 10/2006 | |
| WO | WO 2007/024391 | 3/2007 | |
| WO | WO 2007/131180 | 11/2007 | |
| WO | WO 2008/014382 | 1/2008 | |
| WO | WO 2008/086470 | 7/2008 | |
| WO | WO 2008/106694 | 9/2008 | |
| WO | WO 2009/025819 | 2/2009 | |
| WO | WO 2009/072123 | 6/2009 | |
| WO | WO 2009/119782 | 10/2009 | |
| WO | WO 2009/131837 | 10/2009 | |
| WO | WO 2009/148946 | 12/2009 | |
| WO | WO 2010/006049 | 1/2010 | |
| WO | WO 2010/011404 | 1/2010 | |
| WO | WO 2010/056970 | 5/2010 | |
| WO | WO 2010/123993 | 10/2010 | |
| WO | WO 2011/005978 | 1/2011 | |
| WO | WO 2011/066320 | 6/2011 | |
| WO | WO 2011/106783 | 9/2011 | |
| WO | WO 2011/116238 | 9/2011 | |
| WO | WO2011116238 | 9/2011 | |
| WO | WO 2011/127088 | 10/2011 | |
| WO | WO 2012/032103 | 3/2012 | |
| WO | WO 2012/061676 | 5/2012 | |
| WO | WO 2012/061681 | 5/2012 | |
| WO | WO 2012/061684 | 5/2012 | |
| WO | WO 2012/061688 | 5/2012 | |
| WO | WO2012/061690 * | 5/2012 | |
| WO | WO 2012/061690 | 5/2012 | |
| WO | WO 2012/061741 | 5/2012 | |
| WO | WO 2012/061744 | 5/2012 | |
| WO | WO-2012061690 A2 * | 5/2012 | ......... A01K 67/0275 |
| WO | WO 2012/106407 | 8/2012 | |
| WO | WO-2012106407 A2 * | 8/2012 | ......... G01N 33/6893 |
| WO | WO 2012/134704 | 10/2012 | |
| WO | WO 2013/003557 | 1/2013 | |
| WO | WO 2013/016486 | 1/2013 | |
| WO | WO 2013/090356 | 6/2013 | |
| WO | WO 2013/126521 | 8/2013 | |
| WO | WO 2013/126762 | 8/2013 | |
| WO | WO 2013/142196 | 9/2013 | |
| WO | WO 2014/081449 | 5/2014 | |
| WO | WO 2014/117079 | 7/2014 | |
| WO | WO 2016/019075 | 2/2016 | |

OTHER PUBLICATIONS

Skolnick et al Trends in Biotech, 18, 34-39 (Year: 2000).*
Davis, New Biologist, 2(5), 410-419 (Year: 1990).*
Steimer Dialogues Clin Neurosci. 4:231-249. (Year: 2002).*
Daniel et al Neuropsychopharmacology, 41, 103-125 (Year: 2016).*
Yizhar et al Neuron, 71, 9-34 (Year: 2011).*
Jones, et al.; "Animal Models of Schizophrenia"; British Journal of Pharmacology; vol. 164, pp. 1162-1194 (2011).
Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Coleman, et al.; "Assessing Anxiety in Nonhuman Primates"; Ilar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).

(56) References Cited

OTHER PUBLICATIONS

Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Wang, et al.; "Simultaneous phase and size control of upconversion nanocrystals through lanthanide doping"; Nature; vol. 463, No. 7284, pp. 1061-1065 (Feb. 25, 2010).
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Definition of integral. Merriam-Webster Dictionary, retrieved on Mar. 20, 2017; Retrieved from the internet: <http://www.merriam-webster.com/dictionary/integral>.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Ahmad, et al. "The *Drosophila rhodopsin* cytoplasmic tail domain is required for maintenance of rhabdomere structure." The FASEB Journal, 2007, vol. 21, p. 449-455.

Airan, et al., "Temporally Precise in vivo Control of Intracellular Signaling", 2009, Nature, vol. 458, No. 7241, pp. 1025-1029.
Akirav, et al. "The role of the medial prefrontal cortex-amygdala circuit in stress effects on the extinction of fear", Neural Plasticity, 2007: vol. 2007 Article ID:30873, pp. 1-11.
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant Iox Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-5156.
Arenkiel, et al. "In vivo light-induced activation of neural circuitry in transgenic mice expressing Channelrhodopsin-2", Neuron, 2007, 54:205-218.
Argos, et al. "The integrase family of site-specific recombinases: regional similarities and global diversity", The EMBO Journal, 1986, vol. 5, No. 2, pp. 433-440.
Asano, et al.; "Optically Controlled Contraction of Photosensitive Skeletal Muscle Cells"; Biotechnology & Bioengineering; vol. 109, No. 1, pp. 199-204 (Jan. 2012).
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Babin et al., "Zebrafish Models of Human Motor Neuron Diseases: Advantages and Limitations", Progress in Neurobiology (2014), 118:36-58.
Balint et al., "The Nitrate Transporting Photochemical Reaction Cycle of the Pharanois Halorhodopsin", Biophysical Journal, 2004, 86:1655-1663.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Basil et al., "Is There Evidence for Effectiveness of Transcranial Magnetic Stimulation in the Treatment of Psychiatric Disorders?"; Psychiatry; vol. 1, No. 11, pp. 64-69 (Nov. 2005).
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berke, et al. "Addiction, Dopamine, and the Molecular Mechanisms of Memory", Molecular Plasticity, 2000, vol. 25: pp. 515-532.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Berndt et al. "Bi-stable neural state switches", Nature Neuroscience, 2008, vol. 12, No. 2: pp. 229-234.
Berndt et al., "Structure-guided transformation of channelrhodopsin into a light-activated chloride channel", Science, 2014, 344:420-424.
Berridge et al., "The Versatility and Universality of Calcium Signaling", Nature Reviews: Molecular Cell Biology, 2000, vol. 1: pp. 11-21.

(56) References Cited

OTHER PUBLICATIONS

Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.
Blomer et al., "Highly Efficient and Sustained Gene Transfer in Adult Neurons with Lentivirus Vector", Journal of Virology,1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga *Volvox carteri*", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-7.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cardin, et al. "Driving Fast spiking Cells Induces Gamma Rhythm and Controls Sensory Responses", 2009, Nature, vol. 459, vol. 7247, pp. 663-667.
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.
Cenatiempo "Prokaryotic gene expression in vitro: transcription-translation coupled systems", Biochimie, 1986, vol. 68(4): pp. 505-515.
Chow et al., "Optogenetics and translation medicine", Sci Trans! Med., 2013, 5(177):177.
Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA,1983, vol. 80, p. 1111-1115.

Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Crouse, et al. "Expression and amplification of engineered mouse dihydrofolate reductase minigenes" Mol. Cell. Biol. 1983, vol. 3(2): pp. 257-266.
Cucchiaro et al., "Electron-Microscopic Analysis of Synaptic Input from the Perigeniculate Nucleus to A-Laminae of the Lateral Geniculate Nucleus in Cats", The Journal of Comparitive Neurology, 1991, vol. 310, pp. 316-336.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cui, et al., "Electrochemical deposition and characterization of conducting polymer polypyrrole/PSS on multichannel neural probes," Sensors and Actuators, 2001, vol. 93(1): pp. 8-18.
Dalva, et al. "Rearrangements of Synaptic Connections in Visual Cortex Revealed by Laser Photostimulation", Science, 1994,vol. 265, pp. 255-258.
Date, et al. "Grafting of Encapsulated Dopamine-Secreting Cells in Parkinson's Disease: Long-Term Primate Study", Cell Transplant, 2000, vol. 9, pp. 705-709.
Davis; "The many faces of epidermal growth factor repeats," The New Biologist; vol. 2, No. 5, pp. 410-419 (1990).
Day, et al.; "The Nucleus Accumbens and Pavlovian Reward Learning"; Neuroscientist; vol. 13, No. 2, pp. 148-159 (Apr. 2007).
De Foubert et al. "Fluoxetine-Induced Change in Rat Brain Expression of Brain-Derived Neurotrophic Factor Varies Depending On Length of Treatment," Neuroscience, 2004, vol. 128, pp. 597-604.
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
Dederen, et al. "Retrograde neuronal tracing with cholera toxin B subunit: comparison of three different visualization methods", Histochemical Journal, 1994, vol. 26, pp. 856-862.
Definition of Psychosis (2015).
Deisseroth "Next-generation optical technologies for illuminating genetically targeted brain circuits," The Journal of Neuroscience, 2006, vol. 26, No. 41, pp. 10380-10386.
Deisseroth et al., "Excitation-neurogenesis Coupling in Adult Neural Stem/Progenitor Cells", 2004, Neuron, vol. 42, pp. 535-552.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Signaling from Synapse to Nucleus: the logic Behind the Mechanisms", Currrent Opinion in Neurobiology, 2003, vol. 13, pp. 354-365.
Deisseroth et al., "Translocation of Calmodulin to the Nucleus Supports CREB Phosphorylation in Hippocampal Neurons", Nature, 1998, vol. 392, pp. 198-202.
Deisseroth, et al., "Controlling the Brain with Light", Scientific American, 2010, vol. 303, pp. 48-55.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.

(56) References Cited

OTHER PUBLICATIONS

Do Carmo, et al.; "Modeling Alzheimer's disease in transgenic rats"; Molecular Neurodegeneration; vol. 8, No. 37, 11 pages (2013).
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Ebert et al., "A Moloney MLV-rat somatotropin fusion gene produces biologically active somatotropin in a transgenic pig", Mol. Endocrinology, 1988, vol. 2, pp. 277-283.
EBI accession No. EMBL: J05199; "N. pharaonis halorhodopsin (hop) gene, complete cds"; (Nov. 22, 1990).
EBI accession No. UNIPROT: A7U0Y6; "SubName: Full=Bacteriorhodopsin"; (Aug. 10, 2010).
EBI accession No. UNIPROT: B0R5N9; "Subname: Full=Bacteriorhodopsin"; (Apr. 8, 2008).
EBI accession No. UNIPROT: B4Y103; "SubName: Full=Channelrhodopsin-1"; (Sep. 23, 2008).
EBI accession No. UNIPROT: P15647; "RecName: Full=Halorhodopsin; Short=HR; Alt Name: Full=NpHR"; (Apr. 1, 1990).
Ehrlich I. et al. "Amygdala inhibitory circuits and the control of fear memory", Neuron, 2009, vol. 62: pp. 757-771.
Eijkelkamp, et al. "Neurological perspectives on voltage-gated sodium channels", Brain, 2012, 135:2585-2612.
Eisen, "Treatment of amyotrophic lateral sclerosis", Drugs Aging, 1999; vol. 14, No. 3, pp. 173-196.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Ernst, et al. "Photoactivation of Channelrhodopsin", J. Biol. Chem., 2008, vol. 283, No. 3, pp. 1637-1643.
Esposito et al. "The integrase family of tyrosine recombinases: evolution of a conserved active site domain" , Nucleic Acids Research, 1997, vol. 25, No. 18, pp. 3605-3614.
Evanko "Optical excitation yin and yang" Nature Methods, 2007, 4:384.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fenno et al., "The development and application of optogenetics", Annual Review of Neuroscience, 2011, vol. 34, No. 1, pp. 389-412.
Fiala et al., "Optogenetic approaches in neuroscience", Current Biology, Oct. 2010, 20(20):R897-R903.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Fox et al., "A gene neuron expression fingerprint of C. elegans embryonic motor neurons", BMC Genomics, 2005, 6(42):1-23.
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Garrido et al., "A targeting motif involved in sodium channel clustering at the axonal initial segment", Science, 2003, vol. 300, No. 5628, pp. 2091-2094.
Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurrn, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine 02 receptor 1-4, 24-25 gene, promoter region and exon 1. Jan. 31, 1997.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al. , "The course of neural projection from the prefrontal cortex to the nucleus accumbens in the rat ", Neuroscience, 1997, vol. 76, No. 3, pp. 689-706.
Goshen et al. "Dynamics of Retrieval Strategies for Remote Memories", Cell, 2011, col. 147: pp. 678-589.
Gottesman et al."Bacterial regulation: global regulatory networks," Ann. Rev. Genet. , 1984, vol. 18, pp. 415-441.
Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al., "Ultrafast optogenetic control", Nature Neuroscience, 2010, vol. 13, No. 3, pp. 387-392.

(56) References Cited

OTHER PUBLICATIONS

Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Han, et a.; "Virogenetic and optogenetic mechanisms to define potential therapeutic targets in psychiatric disorders"; Neuropharmacology; vol. 62, pp. 89-100 (2012).
Han, et al., "Millisecond-Timescale Optical Control of Neural Dynamics in the Nonhuman Primate Brain"; Neuron; vol. 62, pp. 191-198 (Apr. 30, 2009).
Han, et al., "Multiple-Color Optical Activation, Silencing, and Desynchronization of Neural Activity with Single-Spike Temporal Resolution", PLoS One, 2007, vol. 2, No. 3, pp. 1-12.
Han; et al., "Two-color, bi-directional optical voltage control of genetically-targeted neurons", CoSyne Abstract Presentation, Presented Feb. 24, 2007.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetylycholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in *Schizosaccharomyces pombe* pumps protons through the plasma membrane, " PNAS, 1993, vol. 90, pp. 3578-3582.
Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 51, No. 3: pp. 237-47.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers" Journal of Cell Science, 2005, vol. 118, p. 1935-1943.
Hosokawa, T. et al. "Imaging spatia-temporal patterns of long-term potentiation in mouse hippocampus." Philos. Trans. R. Soc. Lond. B., 2003, vol. 358, pp. 689-693.

Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.
Isenberg et al.; "Cloning of a Putative Neuronal Nicotinic Aceylcholine Receptor Subunit"; Journal of Neurochemistry; vol. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.
Jimenez S.A & Maren S. et al/ "Nuclear disconnection within the amygdala reveals a direct pathway to fear", Learning Memory, 2009, vol. 16: pp. 766-768.
Johansen, et al., "Optical Activation of Lateral Amygdala Pyramidal Cells Instructs Associative Fear Learning", 2010, PNAS, vol. 107, No. 28, pp. 12692-12697.
Johnston et al. "Isolation of the yeast regulatory gene GAL4 and analysis of its dosage effects on the galactose/melibiose regulon," PNAS, 1982, vol. 79, pp. 6971-6975.
Kaiser; "Clinical research. Death prompts a review of gene therapy vector"; Science; 317(5838):580, 1 page. (Aug. 3, 2007).
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karra, et al. "Transfection Techniques for Neuronal Cells", The Journal of Neuroscience, 2010, vol. 30, No. 18, pp. 6171-6177.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract p. S2 only.
Katz, et al. "Scanning laser photostimulation: a new approach for analyzing brain circuits," Journal of Neuroscience Methods, 1994, vol. 54, pp. 205-218.
Kay; "State-of-the-art gene-based therapies: the road ahead"; Nature Reviews Genetics; vol. 12, pp. 316-328 (May 2011).
Kelder et al., "Glycoconjugates in human and transgenic animal milk", Advances in Exp. Med. And Biol., 2001, vol. 501, pp. 269-278.
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carted are Photochromic Proteins that are Specifically Expressed in Somatic

(56) References Cited

OTHER PUBLICATIONS

Cells under Control of Light, Temperature, and the Sex Inducer", 2009, Plant Physiology, vol. 151, No. 1, pp. 347-366.
Kim et al., "Diverging neural pathways assemble a behavioural state from separable features in anxiety" Nature, 2013, 496(7444):219-23.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kim et al., "PDZ domain proteins of synapses", Nature Reviews Neuroscience, 2004, vol. 5, No. 10, pp. 771-781.
Kingston et al. "Transfection and Expression of Cloned DNA," Supplement 31, Current Protocols in Immunology, 1999, 10.13.1-10.13.9.
Kingston et al. "Transfection of DNA into Eukaryotic Cells," Supplement 63, Current Protocols in Molecular Biology, 1996, 9.1.1-9.1.11, 11 pages.
Kinoshita, et al., "Optogenetically Induced Supression of Neural Activity in the Macaque Motor Cortex", Poster Sessions Somatomotor System, Others, Society for Neuroscience Meeting, 2010, pp. 141-154.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitabatake et al., "Impairment of reward-related learning by cholinergic cell ablationn in the striatum", PNAS, Jun. 2003, 100(13):7965-7970.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Knopfel, et al. "Optical Probing of Neuronal Circuit Dynamics: Gentically Encoded Versus Classical Fluorescent Sensors", 2006, Trends Neurosci, vol. 29, No. 3, pp. 160-166.
Knopfel, et al.; "A comprehensive concept of optogenetics"; Progress in Brain Research; vol. 196, pp. 1-28 (2012).
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Kokel et al., "Photochemical activation of TRPA1 channels in neurons and animals", Nat Chem Biol, 2013, 9(4):257-263.
Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Lalumiere, R., "A new technique for controlling the brain: optogenetics and its potential for use in research and the clinic", Brain Stimulation, 2011, vol. 4, pp. 1-6.
Lammel et al., "Input-specific control of reward and aversion in the ventral tegmental area", Nature, 2012, 491(7423): 212-217.
Landy, A. "Mechanistic and structural complexity in the site-specific recombination pathways of Int and FLP", Current Opinion in Genetics and Development, 1993, vol. 3, pp. 699-707.
Lanyi et al. "The primary structure of a Halorhodopsin from Natronobacterium Pharaonis" Journal of Biological Chemistry, 1990, vol. 265, No. 3, p. 1253-1260.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gene Therapy Can Prevent Neuron Death Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Li et al., "Surface Expression of Kv1 Channels is Governed by a C-Terminal Motif", J. Biol. Chem. (2000), 275(16):11597-11602.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992,vol. 9, pp. 861-871.
Lin, "A user's guide to char nelrhodopsin variants: features, limitations and future developments", Exp Physiol, 2010, vol. 96, No. 1, pp. 19-25.
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.
Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research, 1996, vol. 24, No. 19: pp. 3784-3789.
Ma et al. "Role of ER Export Signals in Controlling Surface Potassium Channel Numbers," Science, 2001, vol. 291, pp. 316-319.
Malin et al., "Involvement of the rostral anterior cingulate cortex in consolidation of inhibitory avoidance memory: Interaction with the basolateral amygdala", Neurobiol Learn Mem., Feb. 2007, 87(2):295-302.
Mancuso et al., "Optogenetic probing of functional brain circuitry", Experimental Physiology, 2010, vol. 96.1, pp. 26-33.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mann; "Synapses"; The Nervous System in Action; Chapter 13, http://michaeldmann.net/mann13.html (downloaded Apr. 2014).
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Mattis et al., "Principles for applying optogenetic tools derived from direct comparative analysis of microbial opsins", Nat Methods, 2011, 9(2):159-72.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
Mayford et al., "Control of memory formation through regulated expression of CaMKII transgene", Science, Dec. 1996,274(5293):1678-1683.
McAllister, "Cellular and Molecular Mechanisms of Dendrite Growth", 2000, Cereb Cortex, vol. 10, No. 10, pp. 963-973.

(56) References Cited

OTHER PUBLICATIONS

McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging , 2001, vol. 24, No. 3, pp. 366-372.
Milella et al. "Opposite roles of dopamine and orexin in quinpirole-induced excessive drinking: a rat model of psychotic polydipsia" Psychopharmacology, 2010, 211:355-366.
Monje et al., "Irradiation Induces Neural Precursor-Cell Dysfunction", Natural Medicine, 2002, vol. 8, No. 9, pp. 955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Mortensen et al. "Selection of Transfected Mammalian Cells," Supplement 86, Current Protocols in Molecular Biology, 1997, 9.5.1-09.5.19.
Mourot et al., "Rapid Optical Control of Nociception with an Ion Channel Photoswitch", Nat Methods, 2012, 9(4):396-402.
Mueller, et al.; "Clinical Gene Therapy Using Recombinant Adeno-Associated Virus Vectors"; Gene Therapy; vol. 15, pp. 858-863 (2008).
Mullins et al., "Expression of the DBA/2J Ren-2 gene in the adrenal gland of transgenic mice", EMBO, 1989, vol. 8, pp. 4065-4072.
Mullins et al., "Fulminant hypertension in transgenic rats harbouring the mouse Ren-2 gene", Nature, 1990, vol. 344, pp. 541-544.
Nacher, et al. "NMDA receptor antagonist treatment increases the production of new neurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.
Nieh et al., "Optogenetic dissection of neural circuits underlying emotional valence and motivated behaviors", Brain Research, E-pub 2012, 1511:73-92.
Nirenberg, et al. "The Light Response of Retinal Ganglion Cells is Truncated by a Displaced Amacrine Circuit", Neuron, 1997, vol. 18: pp. 637-650.
No Authors Listed; "Two bright new faces in gene therapy," Nature Biotechnology, 1996, vol. 14: p. 556.
Nonet, "Visualization of synaptic specializations in live C. elegans with synaptic vesicle protein-GFP fusions", J. Neurosci. Methods, 1999, 89:33-40.
Nunes-Duby, et al. "Similarities and differences among 105 members of the Int family of site-specific recombinases", Nucleic Acids Research, 1998, vol. 26, No. 2: pp. 391-406.

O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Packer, et al.; "Targeting Neurons and Photons for Optogenetics"; Nature Neuroscience; vol. 16, No. 7, pp. 805-815 (Jul. 2013).
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Palmer et al., "The Adult Rat Hippocampus Contains Primordial Neural Stem Cells", Molecular and Cellular Neuroscience, 1997, vol. 8, pp. 389-404.
Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pandya, et al.; "Where in the Brain Is Depression?"; Curr. Psychiatry Rep.; vol. 14, pp. 634-642 (2012).
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .I-9.1 1 .I 8.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Peterlin, et al. "Optical probing of neuronal circuits with calcium indicators," PNAS, 2000, vol. 97, No. 7: pp. 3619-3624.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Pinkham et al., "Neural bases for impaired social cognition in schizophrenia and autism spectrum disorders", Schizophrenia Research, 2008, vol. 99, pp. 164-175.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Qiu et al. "Induction of photosensitivity by heterologous expression of melanopsin", Nature, 2005, vol. 433: pp. 745-749.
Ramalho, et al.; "Mouse genetic corneal disease resulting from transgenic insertional mutagenesis"; Br. J. Ophthalmol.; vol. 88, No. 3, pp. 428-432 (Mar. 2004).
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.

(56) References Cited

OTHER PUBLICATIONS

Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Rathnasingham et al., "Characterization of implantable microfabricated fluid delivery devices," IEEE Transactions on Biomedical Engineering, 2004, vol. 51, No. 1: pp. 138-145.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Ristevski; "Making Better Transgenic Models: Conditional, Temporal, and Spatial Approaches"; Molecular Biotechnology; vol. 29, No. 2, pp. 153-163 (Feb. 2005).
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Sajdyk, et al., "Excitatory Amino Acid Receptors in the Basolateral Amygdala Regulate Anxiety Responses in the Social Interaction Test", Brain Research, 1997, vol. 764, pp. 262-264.
Salzman, et al. "Cortical microstimulation influences perceptual judgements of motion direction", Nature, 1990, vol. 346, pp. 174-177.
Samuelson; "Post-traumatic stress disorder and declarative memory functioning: a review"; Dialogues in Clinical Neuroscience; vol. 13, No. 3, pp. 346-351 (2011).
Santana et al., "Can Zebrafish Be Used as Animal Model to Study Alzheimer's Disease?" Am. J. Neurodegener. Dis. (2012), 1(1):32-48.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008,vol. 33, pp. 368-377.
Schroll et al., "Light-induced activation of distinct modulatory neurons triggers appetitive or aversive learning in drosophila larvae", Current Biology, Sep. 2006, 16(17):1741-1747.
Sclimenti, et al. "Directed evolution of a recombinase for improved genomic integration at a native human sequence," Nucleic Acids Research, 2001, vol. 29, No. 24: pp. 5044-5051.
Sheikh et al., "Neurodegenerative Diseases: Multifactorial Conformational Diseases and Their Therapeutic Interventions", Journal of Neurodegenerative Diseases (2013), Article ID 563481:1-8.
Shepherd, et al. "Circuit Analysis of Experience-Dependent Plasticity in the Developing Rat Barrel Cortex", Neuron, 2003, vol. 38: pp. 277-289.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Sigmund; "Viewpoint: Are Studies in Genetically Altered Mice Out of Control?"; Arterioscler Thromb Vasc Biol.; vol. 20, No, 6, pp. 1425-1429 (Jun. 2000).
Silver, et al. "Amino terminus of the yeast GAL4 gene product is sufficient for nuclear localization" PNAS, 1984, vol. 81, No. 19: pp. 5951-5955.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al.; "Intramolecular Proton Transfer in Channelrhodopsins"; Biophysical Journal; vol. 104, No. 4, pp. 807-807 (Feb. 2013).
Sineshchekov et al., "Two Rhodopsins Mediate Phototaxis to Low and High Intensity Light in Chlamydomas Reinhardtil", PNAS, 2002, vol. 99, No. 13, pp. 8689-8694.
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Slamovits et al., "A bacterial proteorhodopsin proton pump in marie eukaryotes", Nature Comm, 2011, 2:183.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Sohal et al., "Parvalbumin neurons and gamma rhythms enhance cortical circuit performance", Nature, 2009, vol. 459, No. 7247, pp. 698-702.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet, 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Suzuki et al., "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.

(56) References Cited

OTHER PUBLICATIONS

Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Tamai, "Progress in Pathogenesis and Therapeutic Research in Retinitis Pigmentosa and Age Related Macular Degeneration", Nippon Ganka Gakkai Zasshi, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tønnesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$ Influx Through Single Human $Ca_v 2.1$ Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai, et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Varo et al.,"Light-Driven Chloride Ion Transport by Halorhodopsin from Natronobacterium pharaonic. 2. Chloride Release and Uptake, Protein Conformation Change, and Thermodynamics", Biochemistry (1995), 34(44):14500-14507.
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9.1-19.39.

Wall, "Transgenic livestock: Progress and prospects for the future", Theriogenology, 1996, vol. 45, pp. 57-68.
Wang, et al. "Direct-current Nanogenerator Driven by Ultrasonic Waves," Science, 2007, vol. 316, pp. 102-105.
Wang, et al., "High-speed mapping of synaptic connectivity using photostimulation in Channelrhodopsin-2 transgenic mice", PNAS, 2007, vol. 104, No. 19, pp. 8143-8148.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Wang, et al., "Mrgprd-Expressing Polymodal Nociceptive Neurons Innervate Most Known Classes of Substantia Gelatinosa Neurons", J Neurosci, 2009, 29(42):13202-13209.
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Williams et al., "From optogenetic technologies to neuromodulation therapies", Sci Transl Med., 2013, 5(177):177.
Witten et. al., "Cholinergic Interneurons Control Local Circuit Activity and Cocaine Conditioning", Science, 2010, vol. 330, No. 6011: pp. 1677-1681.
Witten et. al., Supporting Online Material for: "Cholinergic Interneurons Control Local Circuit Activity and Cocaine Conditioning", Science, 2010, vol. 330: 17 pages.
Written opinion of PCT Application No. PCT/US2011/059383 (dated May 9, 2012).
Xiong et al., "Interregional connectivity to primary motor cortex revealed using MRI resting state images", Hum Brain Mapp, 1999, 8(2-3):151-156.
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.
Yizhar et al., "Optogenetics in neural systems", Neuron Primer, vol. 71, No. 1, pp. 9-34 (Jul. 14, 2011).
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang "Multimodal fast optical interrogation of neural circuitry," Nature, 2007, vol. 446, pp. 633-641.

(56) References Cited

OTHER PUBLICATIONS

Zhang, et al. "Channelrhodopsin-2 and optical control of excitable cells," Nature Methods, 2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008, vol. 11, No. 6, pp. 631-633.
Zhang, et al., "The Microbial Opsin Family of Optogenetic Tools", Cell, 2011, vol. 147, No. 7, pp. 1146-1457.
Zhang, et al.; "Optogenetic interrogation of neural circuits: Technology for probing mammalian brain structures"; Nature Protocols; vol. 5, No. 3, pp. 439-456 (Feb. 18, 2010).
Zhao, et al., "Improved Expression of Halorhodopsin for Light-Induced Silencing of Neuronal Activity", Brain Cell Biology, 2008, vol. 36 (1-4), pp. 141-154.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Tsuchida; "Nervous Control of Micturition"; The Japanese Journal of Urology; vol. 80, No. 9, pp. 1257-1277 (1989).
Co-pending U.S. Appl. No. 14/822,552, filed Aug. 10, 2015.
Co-pending U.S. Appl. No. 14/886,763, filed Oct. 19, 2015.
Co-pending U.S. Appl. No. 14/911,405, filed Feb. 26, 2016.
Co-pending U.S. Appl. No. 15/008,214, filed Jan. 27, 2016.
Co-pending U.S. Appl. No. 15/059,159, filed Mar. 2, 2016.
Definition of Implant; Merriam-Webster Dictionary; retrieved Nov. 7, 2016 (http://www.merriam-webster.com/dictionary/implant).
Ferenczi, et al.; "Optogenetic approaches addressing extracellular modulation of neural excitability"; Scientific Reports; vol. 6, 20 pages (Apr. 5, 2016).
Li, et al.; "A Method for Activiation of Endogenous Acid-sensing Ion Channel 1a (ASIC1 a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Gritton, et al.; "Optogenetically-evoked cortical cholinergic transients in mice expressing channelrhodopsin-2 (Ch R2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Kugler, et al.; "Neuron-Specific Expression of Therapeutic Proteins: Evaluation of Different Cellular Promoters in Recombinant Adenoviral Vectors"; Molecular and Cellular Neuroscience; vol. 17, pp. 78-96 (2001).
Masaki, et al.; "β2-Adrenergic Receptor Regulation of the Cardiac L-Type Ca2+ Channel Coexpressed in a Fibroblast Cell Line"; Receptor; vol. 5, pp. 219-231 (1996).
Smith, et al.; "Proton binding sites involved in the activation of acid-sensing ion channel ASIC2a"; Neuroscience Letters; vol. 426, pp. 12-17 (2007).
Bass, et al.; "Optogenetic control of striatal dopamine release in rats"; Journal of Neurochemistry; vol. 114, pp. 1344-1352 (2010).
Johansen; "Neuroscience: Anxiety is the sum of its parts"; Nature; 2 pages (2013).
Stefanik, et al.; "Optogenetic inhibition of cocaine seeking in rats"; Addiction Biology; vol. 18, pp. 50-53 (2012).
Tsubota, et al.; "Optogenetic Inhibition of Purkinje Cell Activity Reveals Cerebellar Control of Blood Pressure During Postural Alterations in Anesthetized Rats"; Neuroscience; vol. 210, pp. 137-144 (2012).
Wang, et al.; "Approaches to Optical Neuromodulation from Rodents to Non-Human Primates by Integrated Optoelectronic Devices"; 33rd Annual International Conference of the IEEE EMBS; pp. 7525-7528 (Aug. 30-Sep. 3, 2011).
Wang, et al.; "Integrated device for combined optical neuromodulation and electrical recording for chronic in vivo applications"; J. Neural. Eng.; vol. 9, 14 pages (2012).
Boyden, et al.; "A history of optogenetics: the development of tools for controlling brain circuits with light"; F1000 Biology Reports; vol. 3, No. 11, 12 pages (May 3, 2011).
Knox, et al.; "Heterologous Expression of *Limulus* Rhodopsin"; The Journal of Biological Chemistry; vol. 278, No. 42, pp. 40493-40502 (Oct. 17, 2003).
Lin, et al.; "Characterization of Engineered Channelrhodopsin Variants with Improved Properties and Kinetics"; Biophysical Journal; vol. 96, No. 5, pp. 1803-1814 (Mar. 2009).
Friedman, et al.; "VTA Dopamine Neuron Bursting is Altered in an Animal Model of Depression and Corrected by Desipramine"; J. Mol. Neurosci.; vol. 34, pp. 201-209 (2008).
Hackmann, et al.; "Static and time-resolved step-scan Fourier transform infrared investigations of the photoreaction of halorhodopsin from Natronobacterium pharaonis: consequences for models of the anion translocation mechanism"; Biophysical Journal; vol. 81, pp. 394-406 (Jul. 2001).
Weiss, et al.; "Galanin: A Significant Role in Depression?"; Annals New York Academy of Sciences; vol. 863, No. 1, pp. 364-382 (1998).
Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).
Bibel, et al.; "Differentiation of mouse embryonic stem cells into a defined neuronal lineage"; Nature Neuroscience; vol. 7, No. 9, pp. 1033-1009 (Sep. 2004).
Daniel, et al.; "Stress Modulation of Opposing Circuits in the Bed Nucleus of the Stria Terminalis"; Neuropsychopharmacology Reviews; vol. 41, pp. 103-125 (2016).
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Knopfel, et al.; "Remote control of cells"; Nature Nanotechnology; vol. 5, pp. 560-561 (Aug. 2010).
Steimer; "The biology of fear- and anxiety-related behaviors"; Dialogues in Clinical Neuroscience; vol. 4, No. 3, pp. 231-249 (Sep. 2002).
Stuber; "Dissecting the neural circuitry of addiction and psychiatric disease with optogenetics"; Neuropsychopharmacology; vol. 35, No. 1, pp. 341-342 (2010).
Gerits, et al.; "Optogenetically Induced Behavioral and Functional Network Changes in Primates"; Current Biology; vol. 22, pp. 1722-1726 (Sep. 25, 2012).

(56) References Cited

OTHER PUBLICATIONS

Han, et al.; "Optogenetics in the nonhuman primate"; Prog. Brain Res.; vol. 196, pp. 215-233 (2012).
Duvarci, et al., "The bed Nucleus of the Stria Terminalis Mediates inter-individual variations in anxiety and fear", J. Neurosci., 29(33) 10357-10361 (2009).
Matsuda "Bed nucleus of stria terminalis (BNST)" Benshi Seishin Igaku (Molecular Psychiatric Medicine), 2009, vol. 9 No. 3, p. 46-49.
Neuropsychopharmacology, 2011, vol. 36 No. Suppl.1, p. S110 (Abstract No. 67) (Newly cited document).
Neuropsychopharmacology, 2012, vol. 38 No. Suppl.1, p. S48 (Abstract No. 37.2).
Walker et al. "Selective Participation of the Bed Nucleus of the Stria Terminalis and CRF in Sustained Anxiety-like versus Phasic Fear-Like Responses," Prog Neuropsychopharmacol Bio Psychiatry, 13: 33(8) 1291-1308 (2009).
Gonzalez-Barrios, et al.; "Neurotensin Polyplex as an Efficient Carrier for Delivering the Human GDNF Gene into Nigral Dopamine Neurons of Hemiparkinsonian Rats"; Molecular Therapy; vol. 14, No. 6, pp. 857-865 (Dec. 2006).
Tsukamoto, et al.; "Homotrimer Formation and Dissociation of pharaonis Halorhodopsin in Detergent System"; Biophysical Journal; vol. 102, pp. 2906-2915 (Jun. 2012).
Zhang, et al.; "Normalization of Striatal Tyrosine Hydroxylase and Reversal of Motor Impairment in Experimental Parkinsonism with Intravenous Nonviral Gene Therapy and a Brain-Specific Promoter"; Human Gene Therapy; vol. 15, No. 4, 2 pages (Jul. 7, 2004).
Belzung et al., "Optogenetics to study the circuits of fear- and depresssion-like behaviors: A critical analysis," Pharmacology, Biochemistry and Behavior, 2014, 122: 144-157.
Bernstein & Boyden "Optogenetic tools for analyzing the neural circuits of behavior," Trends Cogn Sci., 2011 15(12): 592-600.
Sharma et al., (2007) "Evolution of rhodopsin ion pumps in haloarchaea," BMC Evolutionary Biology, 7:79 pp. 1-13.
Lobo, et al.; "Cell Type Specific Loss of BDNF Signaling Mimics Optogenetic Control of Cocaine Reward"; Science; vol. 330, No. 6002, pp. 385-390 (Oct. 15, 2010).
Mattis, et al.; "Principles for applying optogenetic tools derived from direct comparative analysis of microbial opsins"; Nat Methods; vol. 9, No. 2, pp. 159-172 (Sep. 17, 2014).
Tsukamoto, et al.; "Homotrimer Formation and Dissociation of pharaonis Halorhodopsin in Detergent System"; Biophysical Journal; vol. 102, No. 12, pp. 2906-2915 (Jun. 2012).
Ahmad, et al. "Heterplogous expression of bovine rhodopsin in *Drosophila* photoreceptor cells" Invest Ophthalmol Vis Sci. 2006, 3722-3728.
Clare "Targeting Ion Channels for Drug Discovery" Discov Med. 2010 vol. 9 No. 46 pp. 1-6.
Clare "Functional Expression of Ion Channels in Mammalian Systems" Protein Science Encyclopedia A.R. Fersht (Ed.) 2008 pp. 79-109.
Reeves et al., "Structure and function in rhodosin: A tetracycline-inducible system in stable mammalian cell lines for high-level expression of opsin mutants" PNAS, 2002 vol. 99 No. 21 pp. 13413-13418.

\* cited by examiner

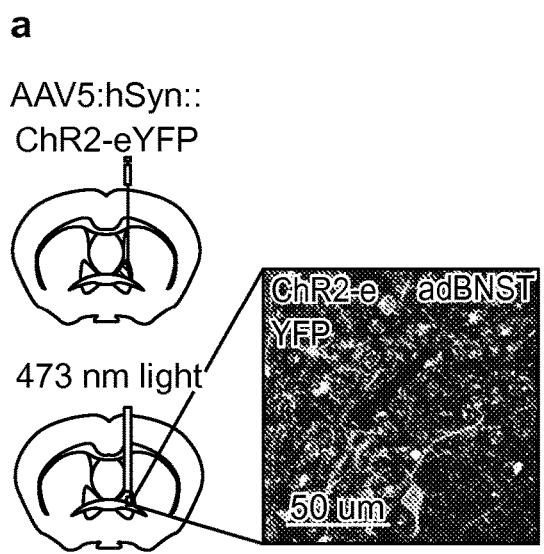
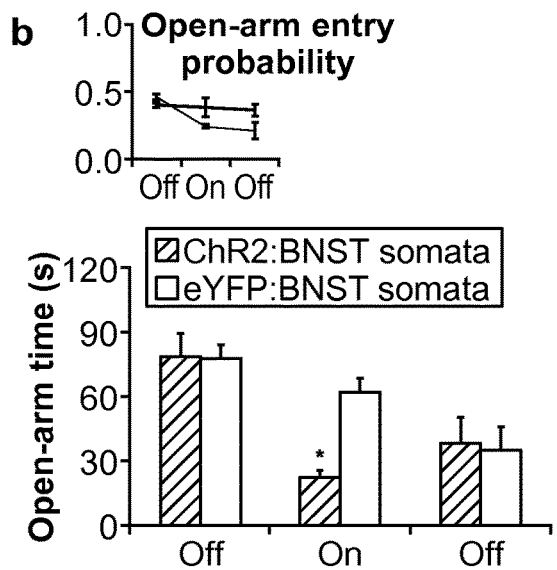
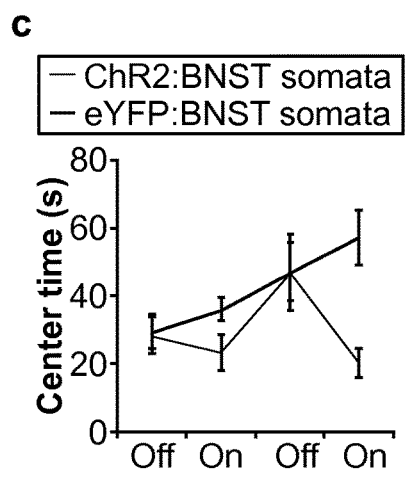
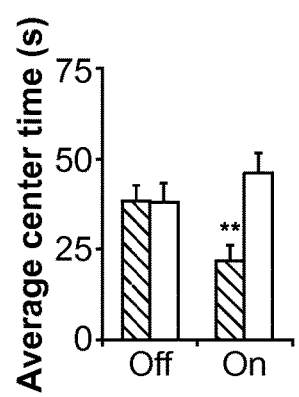
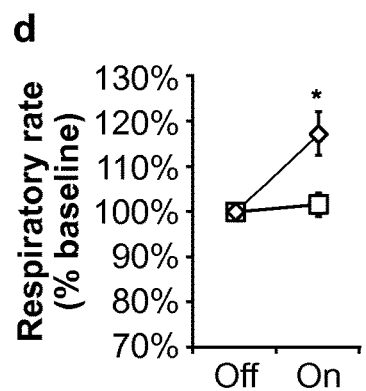
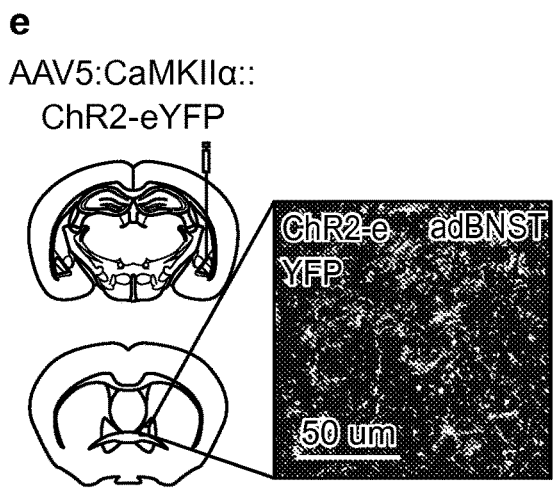
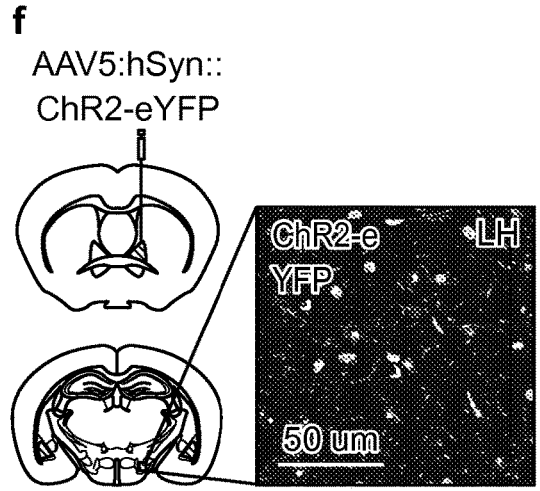
FIG. 7

INHIBITORY

The amino acid sequence of NpHR without the signal peptide:

VTQRELFEFVLNDPLLASSLYINIALAGLSILLFVFMTRGLDDPRAKLIAVSTILVPVVSIAS
YTGLASGLTISVLEMPAGHFAEGSSVMLGGEEVDGVVTMWGRYLTWALSTPMILLALG
LLAGSNATKLFTAITFDIAMCVTGLAAALTTSSHLMRWFWYAISCACFLVVLYILLVEW
AQDAKAAGTADMFNTLKLLTVVMWLGYPIVWALGVEGIAVLPVGVTSWGYSFLDIVA
KYIFAFLLLNYLTSNESVVSGSILDVPSASGTPADD (SEQ ID NO:1).

The amino acid sequence of eYFP-NpHR3.0:

MTETLPPVTESAVALQAEVTQRELFEFVLNDPLLASSLYINIALAGLSILLFVFMTRGLDD
PRAKLIAVSTILVPVVSIASYTGLASGLTISVLEMPAGHFAEGSSVMLGGEEVDGVVTMW
GRYLTWALSTPMILLALGLLAGSNATKLFTAITFDIAMCVTGLAAALTTSSHLMRWFWY
AISCACFLVVLYILLVEWAQDAKAAGTADMFNTLKLLTVVMWLGYPIVWALGVEGIAV
LPVGVTSWGYSFLDIVAKYIFAFLLLNYLTSNESVVSGSILDVPSASGTPADDAAAKSRIT
SEGEYIPLDQIDINVVSKGEELFTGVVPILVELDGDVNGHKFSVSGEGEGDATYGKLTLKF
ICTTGKLPVPWPTLVTTFGYGLQCFARYPDHMKQHDFFKSAMPEGYVQERTIFFKDDGN
YKTRAEVKFEGDTLVNRIELKGIDFKEDGNILGHKLEYNYNSHNVYIMADKQKNGIKVN
FKIRHNIEDGSVQLADHYQQNTPIGDGPVLLPDNHYLSYQSALSKDPNEKRDHMVLLEF
VTAAGITLGMDELYKFCYENEV (SEQ ID NO:2).

The amino acid sequence of eYFP-NpHR3.1:

MVTQRELFEFVLNDPLLASSLYINIALAGLSILLFVFMTRGLDDPRAKLIAVSTILVPVVSI
ASYTGLASGLTISVLEMPAGHFAEGSSVMLGGEEVDGVVTMWGRYLTWALSTPMILLA
LGLLAGSNATKLFTAITFDIAMCVTGLAAALTTSSHLMRWFWYAISCACFLVVLYILLVE
WAQDAKAAGTADMFNTLKLLTVVMWLGYPIVWALGVEGIAVLPVGVTSWGYSFLDIV
AKYIFAFLLLNYLTSNESVVSGSILDVPSASGTPADDAAAKSRITSEGEYIPLDQIDINVVS
KGEELFTGVVPILVELDGDVNGHKFSVSGEGEGDATYGKLTLKFICTTGKLPVPWPTLVT
TFGYGLQCFARYPDHMKQHDFFKSAMPEGYVQERTIFFKDDGNYKTRAEVKFEGDTLV
NRIELKGIDFKEDGNILGHKLEYNYNSHNVYIMADKQKNGIKVNFKIRHNIEDGSVQLAD
HYQQNTPIGDGPVLLPDNHYLSYQSALSKDPNEKRDHMVLLEFVTAAGITLGMDELYKF
CYENEV (SEQ ID NO:3).

The amino acid sequence of GtR3:

ASSFGKALLEFVFIVFACITLLLGINAAKSKAASRVLFPATFVTGIASIAYFSMASGGGWVI
APDCRQLFVARYLDWLITTPLLLIDLGLVAGVSRWDIMALCLSDVLMIATGAFGSLTVG
NVKWVWWFFGMCWFLHIIFALGKSWAEAAKAKGGDSASVYSKIAGITVITWFCYPVV
WVFAEGFGNFSVTFEVLIYGVLDVISKAVFGLILMSGAATGYESI (SEQ ID NO:4).

FIG. 28A

The amino acid sequence of eArch:

MDPIALQAGYDLLGDGRPETLWLGIGTLLMLIGTFYFLVRGWGVTDKDAREYYAVTIL
VPGIASAAYLSMFFGIGLTEVTVGGEMLDIYYARYADWLFTTPLLLLDLALLAKVDRV
TIGTLVGVDALMIVTGLIGALSHTAIARYSWWLFSTICMIVVLYFLATSLRSAAKERGPE
VASTFNTLTALVLVLWTAYPILWIIGTEGAGVVGLGIETLLFMVLDVTAKVGFGFILLR
SRAILGDTEAPEPSAGADVSAAD (SEQ ID NO:12).

The amino acid sequence of eArch3.0-EYFP:

MDPIALQAGYDLLGDGRPETLWLGIGTLLMLIGTFYFLVRGWGVTDKDAREYYAVTIL
VPGIASAAYLSMFFGIGLTEVTVGGEMLDIYYARYADWLFTTPLLLLDLALLAKVDRV
TIGTLVGVDALMIVTGLIGALSHTAIARYSWWLFSTICMIVVLYFLATSLRSAAKERGPE
VASTFNTLTALVLVLWTAYPILWIIGTEGAGVVGLGIETLLFMVLDVTAKVGFGFILLR
SRAILGDTEAPEPSAGADVSAADRPVVAVSKAAAKSRITSEGEYIPLDQIDINVVSKGEE
LFTGVVPILVELDGDVNGHKFSVSGEGEGDATYGKLTLKFICTTGKLPVPWPTLVTTFG
YGLQCFARYPDHMKQHDFFKSAMPEGYVQERTIFFKDDGNYKTRAEVKFEGDTLVNR
IELKGIDFKEDGNILGHKLEYNYNSHNVYIMADKQKNGIKVNFKIRHNIEDGSVQLAD
HYQQNTPIGDGPVLLPDNHYLSYQSALSKDPNEKRDHMVLLEFVTAAGITLGMDELY
KFCYENEV (SEQ ID NO:13).

ArchT 3.0

MDPIALQAGYDLLGDGRPETLWLGIGTLLMLIGTFYFIVKGWGVTDKEAREYYSITILVP
GIASAAYLSMFFGIGLTEVTVAGEVLDIYYARYADWLFTTPLLLDLALLAKVDRVSIGT
LVGVDALMIVTGLIGALSHTPLARYSWWLFSTICMIVVLYFLATSLRAAAKERGPEVAST
FNTLTALVLVLWTAYPILWIIGTEGAGVVGLGIETLLFMVLDVTAKVGFGFILLRSRAIL
GDTEAPEP (SEQ ID NO:14)

Mac 3.0

MIVDQFEEVLMKTSQLFPLPTATQSAQPTHVAPVPTVLPDTPIYETVGDSGSKTLWVVFV
LMLIASAAFTALSWKIPVNRRLYHVITTIITLTAALSYFAMATGHGVALNKIVIRTQHDH
VPDTYETVYRQVYYARYIDWAITTPLLLLDLGLLAGMSGAHIFMAIVADLIMVLTGLFAA
FGSEGTPQKWGWYTIACIAYIFVVWHLVLNGGANARVKGEKLRSFFVAIGAYTLILWTAY
PIVWGLADGARKIGVDGEIIAYAVLDVLAKGVFGAWLLVTHANLRESDVELNGFWANGLN
REGAIRIGEDDGARPVVAVSK (SEQ ID NO:15)

FIG. 28B

EXCITATORY

The amino acid sequence of ChR2:

MDYGGALSAVGRELLFVTNPVVVNGSVLVPEDQCYCAGWIESRGTNGAQTASNVLQW
LAAGFSILLLMFYAYQTWKSTCGWEEIYVCAIEMVKVILEFFFEFKNPSMLYLATGHRVQ
WLRYAEWLLTCPVILIHLSNLTGLSNDYSRRTMGLLVSDIGTIVWGATSAMATGYVKVIF
FCLGLCYGANTFFHAAKAYIEGYHTVPKGRCRQVVTGMAWLFFVSWGMFPILFILGPEG
FGVLSVYGSTVGHTIIDLMSKNCWGLLGHYLRVLIHEHILIHGDIRKTTKLNIGGTEIEVET
LVEDEAEAGAVP (SEQ ID NO:5).

The amino acid sequence of SFO:

MDYGGALSAVGRELLFVTNPVVVNGSVLVPEDQCYCAGWIESRGTNGAQTASNVLQW
LAAGFSILLLMFYAYQTWKSTCGWEEIYVCAIEMVKVILEFFFEFKNPSMLYLATGHRVQ
WLRYAEWLLTSPVILIHLSNLTGLSNDYSRRTMGLLVSDIGTIVWGATSAMATGYVKVIF
FCLGLCYGANTFFHAAKAYIEGYHTVPKGRCRQVVTGMAWLFFVSWGMFPILFILGPEG
FGVLSVYGSTVGHTIIDLMSKNCWGLLGHYLRVLIHEHILIHGDIRKTTKLNIGGTEIEVET
LVEDEAEAGAVP (SEQ ID NO:6).

The amino acid sequence of SSFO:

MDYGGALSAVGRELLFVTNPVVVNGSVLVPEDQCYCAGWIESRGTNGAQTASNVLQW
LAAGFSILLLMFYAYQTWKSTCGWEEIYVCAIEMVKVILEFFFEFKNPSMLYLATGHRVQ
WLRYAEWLLTSPVILIHLSNLTGLSNDYSRRTMGLLVSAIGTIVWGATSAMATGYVKVIF
FCLGLCYGANTFFHAAKAYIEGYHTVPKGRCRQVVTGMAWLFFVSWGMFPILFILGPEG
FGVLSVYGSTVGHTIIDLMSKNCWGLLGHYLRVLIHEHILIHGDIRKTTKLNIGGTEIEVET
LVEDEAEAGAVP (SEQ ID NO:7).

The amino acid sequence of C1V1:

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGYQTW
KSTCGWEEIYVATIEMIKFIIEYFHEFDEPAVIYSSNGNKTVWLRYAEWLLTCPVLLIHL
SNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISPYGSAIGHSI
LDLIAKNMWGVLGNYLRVKIHEHILLYGDIRKKQKITIAGQEMEVETLVAEEED (SEQ
ID NO:8).

The amino acid sequence of C1V1 (E122T):

MSRRPWLLALALAVALAAGSAGASTGSDATVPVATQDGPDYVFHRAHERMLFQTSYTL
ENNGSVICIPNNGQCFCLAWLKSNGTNAEKLAANILQWITFALSALCLMFYGYQTWKST
CGWETIYVATIEMIKFIIEYFHEFDEPAVIYSSNGNKTVWLRYAEWLLTCPVLLIHLSNLT
GLKDDYSKRTMGLLVSDVGCIVWGATSAMCTGWTKILFFLISLSYGMYTYFHAAKVYIE
AFHTVPKGICRELVRVMAWTFFVAWGMFPVLFLLGTEGFGHISPYGSAIGHSILDLIAKN
MWGVLGNYLRVKIHEHILLYGDIRKKQKITIAGQEMEVETLVAEEED (SEQ ID NO:9).

FIG. 28C

The amino acid sequence of C1V1 (E162T):

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGYQTW
KSTCGWEEIYVATIEMIKFIIEYFHEFDEPAVIYSSNGNKTVWLRYATWLLTCPVLLIHL
SNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISPYGSAIGHSI
LDLIAKNMWGVLGNYLRVKIHEHILLYGDIRKKQKITIAGQEMEVETLVAEEED (SEQ
ID NO:10).

The amino acid sequence of C1V1 (E122T/E162T):

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGYQTW
KSTCGWETIYVATIEMIKFIIEYFHEFDEPAVIYSSNGNKTVWLRYATWLLTCPVLLIHL
SNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISPYGSAIGHSI
LDLIAKNMWGVLGNYLRVKIHEHILLYGDIRKKQKITIAGQEMEVETLVAEEED (SEQ
ID NO:11).

SEQUENCE LISTING

<160> NUMBER OF SEQ ID NOS: 28

<210> SEQ ID NO 1
<211> LENGTH: 273
<212> TYPE: PRT
<213> ORGANISM: Natronomonas pharaonis

<400> SEQUENCE: 1

Val Thr Gln Arg Glu Leu Phe Glu Phe Val Leu Asn Asp Pro Leu Leu
1               5                   10                  15

Ala Ser Ser Leu Tyr Ile Asn Ile Ala Leu Ala Gly Leu Ser Ile Leu
            20                  25                  30

Leu Phe Val Phe Met Thr Arg Gly Leu Asp Asp Pro Arg Ala Lys Leu
        35                  40                  45

Ile Ala Val Ser Thr Ile Leu Val Pro Val Val Ser Ile Ala Ser Tyr
    50                  55                  60

Thr Gly Leu Ala Ser Gly Leu Thr Ile Ser Val Leu Glu Met Pro Ala
65                  70                  75                  80

Gly His Phe Ala Glu Gly Ser Ser Val Met Leu Gly Gly Glu Glu Val
                85                  90                  95

Asp Gly Val Val Thr Met Trp Gly Arg Tyr Leu Thr Trp Ala Leu Ser
            100                 105                 110

Thr Pro Met Ile Leu Leu Ala Leu Gly Leu Leu Ala Gly Ser Asn Ala
        115                 120                 125

Thr Lys Leu Phe Thr Ala Ile Thr Phe Asp Ile Ala Met Cys Val Thr
    130                 135                 140

Gly Leu Ala Ala Ala Leu Thr Thr Ser Ser His Leu Met Arg Trp Phe

```
                145                 150                 155                 160
Trp Tyr Ala Ile Ser Cys Ala Cys Phe Leu Val Val Leu Tyr Ile Leu
                    165                 170                 175

Leu Val Glu Trp Ala Gln Asp Ala Lys Ala Ala Gly Thr Ala Asp Met
            180                 185                 190

Phe Asn Thr Leu Lys Leu Leu Thr Val Val Met Trp Leu Gly Tyr Pro
                195                 200                 205

Ile Val Trp Ala Leu Gly Val Glu Gly Ile Ala Val Leu Pro Val Gly
        210                 215                 220

Val Thr Ser Trp Gly Tyr Ser Phe Leu Asp Ile Val Ala Lys Tyr Ile
225                 230                 235                 240

Phe Ala Phe Leu Leu Leu Asn Tyr Leu Thr Ser Asn Glu Ser Val Val
                245                 250                 255

Ser Gly Ser Ile Leu Asp Val Pro Ser Ala Ser Gly Thr Pro Ala Asp
                260                 265                 270

Asp

<210> SEQ ID NO 2
<211> LENGTH: 559
<212> TYPE: PRT
<213> ORGANISM: Artificial Sequence
<220> FEATURE:
<223> OTHER INFORMATION: synthetic amino acid sequence

<400> SEQUENCE: 2

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240
```

Val Gly Val Thr Ser Trp Gly Tyr Ser Phe Leu Asp Ile Val Ala Lys
            245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
            275                 280                 285

Ala Asp Asp Ala Ala Ala Lys Ser Arg Ile Thr Ser Glu Gly Glu Tyr
            290                 295                 300

Ile Pro Leu Asp Gln Ile Asp Ile Asn Val Val Ser Lys Gly Glu Glu
305                 310                 315                 320

Leu Phe Thr Gly Val Val Pro Ile Leu Val Glu Leu Asp Gly Asp Val
            325                 330                 335

Asn Gly His Lys Phe Ser Val Ser Gly Glu Gly Glu Gly Asp Ala Thr
            340                 345                 350

Tyr Gly Lys Leu Thr Leu Lys Phe Ile Cys Thr Thr Gly Lys Leu Pro
            355                 360                 365

Val Pro Trp Pro Thr Leu Val Thr Thr Phe Gly Tyr Gly Leu Gln Cys
            370                 375                 380

Phe Ala Arg Tyr Pro Asp His Met Lys Gln His Asp Phe Phe Lys Ser
385                 390                 395                 400

Ala Met Pro Glu Gly Tyr Val Gln Glu Arg Thr Ile Phe Phe Lys Asp
            405                 410                 415

Asp Gly Asn Tyr Lys Thr Arg Ala Glu Val Lys Phe Glu Gly Asp Thr
            420                 425                 430

Leu Val Asn Arg Ile Glu Leu Lys Gly Ile Asp Phe Lys Glu Asp Gly
            435                 440                 445

Asn Ile Leu Gly His Lys Leu Glu Tyr Asn Tyr Asn Ser His Asn Val
450                 455                 460

Tyr Ile Met Ala Asp Lys Gln Lys Asn Gly Ile Lys Val Asn Phe Lys
465                 470                 475                 480

Ile Arg His Asn Ile Glu Asp Gly Ser Val Gln Leu Ala Asp His Tyr
            485                 490                 495

Gln Gln Asn Thr Pro Ile Gly Asp Gly Pro Val Leu Leu Pro Asp Asn
            500                 505                 510

His Tyr Leu Ser Tyr Gln Ser Ala Leu Ser Lys Asp Pro Asn Glu Lys
            515                 520                 525

Arg Asp His Met Val Leu Leu Glu Phe Val Thr Ala Ala Gly Ile Thr
            530                 535                 540

Leu Gly Met Asp Glu Leu Tyr Lys Phe Cys Tyr Glu Asn Glu Val
545                 550                 555

<210> SEQ ID NO 3
<211> LENGTH: 542
<212> TYPE: PRT
<213> ORGANISM: Artificial sequence
<220> FEATURE:
<223> OTHER INFORMATION: synthetic amino acid sequence

<400> SEQUENCE: 3

Met Val Thr Gln Arg Glu Leu Phe Glu Phe Val Leu Asn Asp Pro Leu
1               5                   10                  15

Leu Ala Ser Ser Leu Tyr Ile Asn Ile Ala Leu Ala Gly Leu Ser Ile
            20                  25                  30

Leu Leu Phe Val Phe Met Thr Arg Gly Leu Asp Asp Pro Arg Ala Lys
            35                  40                  45

Leu Ile Ala Val Ser Thr Ile Leu Val Pro Val Ser Ile Ala Ser
            50                  55                  60

Tyr Thr Gly Leu Ala Ser Gly Leu Thr Ile Ser Val Leu Glu Met Pro
 65                  70                  75                  80

Ala Gly His Phe Ala Glu Gly Ser Ser Val Met Leu Gly Gly Glu Glu
                 85                  90                  95

Val Asp Gly Val Val Thr Met Trp Gly Arg Tyr Leu Thr Trp Ala Leu
                100                 105                 110

Ser Thr Pro Met Ile Leu Leu Ala Leu Gly Leu Leu Ala Gly Ser Asn
            115                 120                 125

Ala Thr Lys Leu Phe Thr Ala Ile Thr Phe Asp Ile Ala Met Cys Val
        130                 135                 140

Thr Gly Leu Ala Ala Ala Leu Thr Thr Ser Ser His Leu Met Arg Trp
145                 150                 155                 160

Phe Trp Tyr Ala Ile Ser Cys Ala Cys Phe Leu Val Val Leu Tyr Ile
                165                 170                 175

Leu Leu Val Glu Trp Ala Gln Asp Ala Lys Ala Ala Gly Thr Ala Asp
            180                 185                 190

Met Phe Asn Thr Leu Lys Leu Leu Thr Val Val Met Trp Leu Gly Tyr
        195                 200                 205

Pro Ile Val Trp Ala Leu Gly Val Glu Gly Ile Ala Val Leu Pro Val
210                 215                 220

Gly Val Thr Ser Trp Gly Tyr Ser Phe Leu Asp Ile Val Ala Lys Tyr
225                 230                 235                 240

Ile Phe Ala Phe Leu Leu Leu Asn Tyr Leu Thr Ser Asn Glu Ser Val
                245                 250                 255

Val Ser Gly Ser Ile Leu Asp Val Pro Ser Ala Ser Gly Thr Pro Ala
            260                 265                 270

Asp Asp Ala Ala Ala Lys Ser Arg Ile Thr Ser Glu Gly Glu Tyr Ile
        275                 280                 285

Pro Leu Asp Gln Ile Asp Ile Asn Val Val Ser Lys Gly Glu Glu Leu
        290                 295                 300

Phe Thr Gly Val Val Pro Ile Leu Val Glu Leu Asp Gly Asp Val Asn
305                 310                 315                 320

Gly His Lys Phe Ser Val Ser Gly Glu Gly Glu Gly Asp Ala Thr Tyr
                325                 330                 335

Gly Lys Leu Thr Leu Lys Phe Ile Cys Thr Thr Gly Lys Leu Pro Val
            340                 345                 350

Pro Trp Pro Thr Leu Val Thr Thr Phe Gly Tyr Gly Leu Gln Cys Phe
        355                 360                 365

Ala Arg Tyr Pro Asp His Met Lys Gln His Asp Phe Phe Lys Ser Ala
        370                 375                 380

Met Pro Glu Gly Tyr Val Gln Glu Arg Thr Ile Phe Phe Lys Asp Asp
385                 390                 395                 400

Gly Asn Tyr Lys Thr Arg Ala Glu Val Lys Phe Glu Gly Asp Thr Leu
                405                 410                 415

Val Asn Arg Ile Glu Leu Lys Gly Ile Asp Phe Lys Glu Asp Gly Asn
            420                 425                 430

Ile Leu Gly His Lys Leu Glu Tyr Asn Tyr Asn Ser His Asn Val Tyr
        435                 440                 445

Ile Met Ala Asp Lys Gln Lys Asn Gly Ile Lys Val Asn Phe Lys Ile
        450                 455                 460

```
Arg His Asn Ile Glu Asp Gly Ser Val Gln Leu Ala Asp His Tyr Gln
465                 470                 475                 480

Gln Asn Thr Pro Ile Gly Asp Gly Pro Val Leu Leu Pro Asp Asn His
            485                 490                 495

Tyr Leu Ser Tyr Gln Ser Ala Leu Ser Lys Asp Pro Asn Glu Lys Arg
        500                 505                 510

Asp His Met Val Leu Leu Glu Phe Val Thr Ala Ala Gly Ile Thr Leu
    515                 520                 525

Gly Met Asp Glu Leu Tyr Lys Phe Cys Tyr Glu Asn Glu Val
530                 535                 540

<210> SEQ ID NO 4
<211> LENGTH: 223
<212> TYPE: PRT
<213> ORGANISM: Guillardia theta

<400> SEQUENCE: 4

Ala Ser Ser Phe Gly Lys Ala Leu Leu Glu Phe Val Phe Ile Val Phe
1               5                   10                  15

Ala Cys Ile Thr Leu Leu Gly Ile Asn Ala Ala Lys Ser Lys Ala
            20                  25                  30

Ala Ser Arg Val Leu Phe Pro Ala Thr Phe Val Thr Gly Ile Ala Ser
        35                  40                  45

Ile Ala Tyr Phe Ser Met Ala Ser Gly Gly Trp Val Ile Ala Pro
50                  55                  60

Asp Cys Arg Gln Leu Phe Val Ala Arg Tyr Leu Asp Trp Leu Ile Thr
65                  70                  75                  80

Thr Pro Leu Leu Leu Ile Asp Leu Gly Leu Val Ala Gly Val Ser Arg
                85                  90                  95

Trp Asp Ile Met Ala Leu Cys Leu Ser Asp Val Leu Met Ile Ala Thr
                100                 105                 110

Gly Ala Phe Gly Ser Leu Thr Val Gly Asn Val Lys Trp Val Trp Trp
            115                 120                 125

Phe Phe Gly Met Cys Trp Phe Leu His Ile Ile Phe Ala Leu Gly Lys
130                 135                 140

Ser Trp Ala Glu Ala Ala Lys Ala Lys Gly Gly Asp Ser Ala Ser Val
145                 150                 155                 160

Tyr Ser Lys Ile Ala Gly Ile Thr Val Ile Thr Trp Phe Cys Tyr Pro
                165                 170                 175

Val Val Trp Val Phe Ala Glu Gly Phe Gly Asn Phe Ser Val Thr Phe
            180                 185                 190

Glu Val Leu Ile Tyr Gly Val Leu Asp Val Ile Ser Lys Ala Val Phe
        195                 200                 205

Gly Leu Ile Leu Met Ser Gly Ala Ala Thr Gly Tyr Glu Ser Ile
    210                 215                 220

<210> SEQ ID NO 5
<211> LENGTH: 310
<212> TYPE: PRT
<213> ORGANISM: Chlamydomonas reinhardtii

<400> SEQUENCE: 5

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30
```

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 6
<211> LENGTH: 310
<212> TYPE: PRT
<213> ORGANISM: Artificial sequence
<220> FEATURE:
<223> OTHER INFORMATION: synthetic amino acid sequence

<400> SEQUENCE: 6

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
            85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
            130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
            165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Pro
305                 310

<210> SEQ ID NO 7
<211> LENGTH: 310
<212> TYPE: PRT
<213> ORGANISM: Artificial sequence
<220> FEATURE:
<223> OTHER INFORMATION: synthetic amino acid sequence

<400> SEQUENCE: 7

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
            50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
            85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 8
<211> LENGTH: 349
<212> TYPE: PRT
<213> ORGANISM: Artificial sequence
<220> FEATURE:
<223> OTHER INFORMATION: synthetic amino acid sequence

<400> SEQUENCE: 8

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

```
Leu Thr Gly Leu Lys Asp Asp Tyr Ser Lys Arg Thr Met Gly Leu Leu
                180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
        210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
        290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp Ser Glu Gln Ile Asp
            340                 345

<210> SEQ ID NO 9
<211> LENGTH: 344
<212> TYPE: PRT
<213> ORGANISM: Artificial sequence
<220> FEATURE:
<223> OTHER INFORMATION: synthetic amino acid sequence

<400> SEQUENCE: 9

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190
```

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
        260                 265                 270

Thr Glu Gly Phe Gly His Ile Ser Pro Tyr Gly Ser Ala Ile Gly His
    275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 10
<211> LENGTH: 349
<212> TYPE: PRT
<213> ORGANISM: Artificial sequence
<220> FEATURE:
<223> OTHER INFORMATION: synthetic amino acid sequence

<400> SEQUENCE: 10

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

```
Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp Ser Glu Gln Ile Asp
            340                 345
```

<210> SEQ ID NO 11
<211> LENGTH: 349
<212> TYPE: PRT
<213> ORGANISM: Artificial sequence
<220> FEATURE:
<223> OTHER INFORMATION: synthetic amino acid sequence

<400> SEQUENCE: 11

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
            115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220
```

```
Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
            290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp Ser Glu Gln Ile Asp
            340                 345

<210> SEQ ID NO 12
<211> LENGTH: 258
<212> TYPE: PRT
<213> ORGANISM: Halorubrum sodomense

<400> SEQUENCE: 12

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255
```

Ala Asp

<210> SEQ ID NO 13
<211> LENGTH: 534
<212> TYPE: PRT
<213> ORGANISM: Artificial sequence
<220> FEATURE:
<223> OTHER INFORMATION: synthetic amino acid sequence

<400> SEQUENCE: 13

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Arg Pro Val Val Ala Val Ser Lys Ala Ala Ala Lys Ser Arg
            260                 265                 270

Ile Thr Ser Glu Gly Glu Tyr Ile Pro Leu Asp Gln Ile Asp Ile Asn
        275                 280                 285

Val Val Ser Lys Gly Glu Glu Leu Phe Thr Gly Val Val Pro Ile Leu
    290                 295                 300

Val Glu Leu Asp Gly Asp Val Asn Gly His Lys Phe Ser Val Ser Gly
305                 310                 315                 320

Glu Gly Glu Gly Asp Ala Thr Tyr Gly Lys Leu Thr Leu Lys Phe Ile
                325                 330                 335

Cys Thr Thr Gly Lys Leu Pro Val Pro Trp Pro Thr Leu Val Thr Thr
            340                 345                 350

Phe Gly Tyr Gly Leu Gln Cys Phe Ala Arg Tyr Pro Asp His Met Lys
            355                 360                 365

Gln His Asp Phe Phe Lys Ser Ala Met Pro Glu Gly Tyr Val Gln Glu
    370                 375                 380

Arg Thr Ile Phe Phe Lys Asp Asp Gly Asn Tyr Lys Thr Arg Ala Glu
385                 390                 395                 400

Val Lys Phe Glu Gly Asp Thr Leu Val Asn Arg Ile Glu Leu Lys Gly
                405                 410                 415

Ile Asp Phe Lys Glu Asp Gly Asn Ile Leu Gly His Lys Leu Glu Tyr
                420                 425                 430

Asn Tyr Asn Ser His Asn Val Tyr Ile Met Ala Asp Lys Gln Lys Asn
            435                 440                 445

Gly Ile Lys Val Asn Phe Lys Ile Arg His Asn Ile Glu Asp Gly Ser
        450                 455                 460

Val Gln Leu Ala Asp His Tyr Gln Gln Asn Thr Pro Ile Gly Asp Gly
465                 470                 475                 480

Pro Val Leu Leu Pro Asp Asn His Tyr Leu Ser Tyr Gln Ser Ala Leu
                485                 490                 495

Ser Lys Asp Pro Asn Glu Lys Arg Asp His Met Val Leu Leu Glu Phe
            500                 505                 510

Val Thr Ala Ala Gly Ile Thr Leu Gly Met Asp Glu Leu Tyr Lys Phe
        515                 520                 525

Cys Tyr Glu Asn Glu Val
    530

<210> SEQ ID NO 14
<211> LENGTH: 248
<212> TYPE: PRT
<213> ORGANISM: Artificial sequence
<220> FEATURE:
<223> OTHER INFORMATION: synthetic amino acid sequence

<400> SEQUENCE: 14

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Ile Val Lys Gly Trp Gly Val Thr Asp Lys Glu
            35                  40                  45

Ala Arg Glu Tyr Tyr Ser Ile Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
                100                 105                 110

Val Asp Arg Val Ser Ile Gly Thr Leu Val Gly Val Asp Ala Leu Met
            115                 120                 125

Ile Val Thr Gly Leu Ile Gly Ala Leu Ser His Thr Pro Leu Ala Arg
        130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
                165                 170                 175

-continued

```
Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro
                245

<210> SEQ ID NO 15
<211> LENGTH: 321
<212> TYPE: PRT
<213> ORGANISM: Artificial sequence
<220> FEATURE:
<223> OTHER INFORMATION: synthetic amino acid sequence

<400> SEQUENCE: 15

Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
        35                  40                  45

Asp Ser Gly Ser Lys Thr Leu Trp Val Val Phe Val Leu Met Leu Ile
    50                  55                  60

Ala Ser Ala Ala Phe Thr Ala Leu Ser Trp Lys Ile Pro Val Asn Arg
65                  70                  75                  80

Arg Leu Tyr His Val Ile Thr Ile Ile Thr Leu Thr Ala Ala Leu
            85                  90                  95

Ser Tyr Phe Ala Met Ala Thr Gly His Gly Val Ala Leu Asn Lys Ile
                100                 105                 110

Val Ile Arg Thr Gln His Asp His Val Pro Asp Thr Tyr Glu Thr Val
            115                 120                 125

Tyr Arg Gln Val Tyr Tyr Ala Arg Tyr Ile Asp Trp Ala Ile Thr Thr
        130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
    210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285
```

Val Glu Leu Asn Gly Phe Trp Ala Asn Gly Leu Asn Arg Glu Gly Ala
        290                 295                 300

Ile Arg Ile Gly Glu Asp Asp Gly Ala Arg Pro Val Val Ala Val Ser
305                 310                 315                 320

Lys

<210> SEQ ID NO 16
<211> LENGTH: 20
<212> TYPE: PRT
<213> ORGANISM: Homo sapiens

<400> SEQUENCE: 16

Lys Ser Arg Ile Thr Ser Glu Gly Glu Tyr Ile Pro Leu Asp Gln Ile
1               5                   10                  15

Asp Ile Asn Val
            20

<210> SEQ ID NO 17
<211> LENGTH: 26
<212> TYPE: PRT
<213> ORGANISM: Homo sapiens

<400> SEQUENCE: 17

Met Asp Tyr Gly Gly Ala Leu Ser Ala Val Gly Arg Glu Leu Leu Phe
1               5                   10                  15

Val Thr Asn Pro Val Val Val Asn Gly Ser
            20                  25

<210> SEQ ID NO 18
<211> LENGTH: 27
<212> TYPE: PRT
<213> ORGANISM: Homo sapiens

<400> SEQUENCE: 18

Met Ala Gly His Ser Asn Ser Met Ala Leu Phe Ser Phe Ser Leu Leu
1               5                   10                  15

Trp Leu Cys Ser Gly Val Leu Gly Thr Glu Phe
            20                  25

<210> SEQ ID NO 19
<211> LENGTH: 23
<212> TYPE: PRT
<213> ORGANISM: Homo sapiens

<400> SEQUENCE: 19

Met Gly Leu Arg Ala Leu Met Leu Trp Leu Leu Ala Ala Ala Gly Leu
1               5                   10                  15

Val Arg Glu Ser Leu Gln Gly
            20

<210> SEQ ID NO 20
<211> LENGTH: 18
<212> TYPE: PRT
<213> ORGANISM: Homo sapiens

<400> SEQUENCE: 20

Met Arg Gly Thr Pro Leu Leu Leu Val Val Ser Leu Phe Ser Leu Leu
1               5                   10                  15

Gln Asp

<210> SEQ ID NO 21

```
<211> LENGTH: 5
<212> TYPE: PRT
<213> ORGANISM: Artificial sequence
<220> FEATURE:
<223> OTHER INFORMATION: synthetic amino acid sequence
<220> FEATURE:
<221> NAME/KEY: MISC_FEATURE
<222> LOCATION: (2)..(3)
<223> OTHER INFORMATION: the amino acid in this position can be any
      amino acid

<400> SEQUENCE: 21

Val Xaa Xaa Ser Leu
1               5

<210> SEQ ID NO 22
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 22

Val Lys Glu Ser Leu
1               5

<210> SEQ ID NO 23
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 23

Val Leu Gly Ser Leu
1               5

<210> SEQ ID NO 24
<211> LENGTH: 16
<212> TYPE: PRT
<213> ORGANISM: Artificial sequence
<220> FEATURE:
<223> OTHER INFORMATION: synthetic amino acid sequence

<400> SEQUENCE: 24

Asn Ala Asn Ser Phe Cys Tyr Glu Asn Glu Val Ala Leu Thr Ser Lys
1               5                   10                  15

<210> SEQ ID NO 25
<211> LENGTH: 6
<212> TYPE: PRT
<213> ORGANISM: Artificial sequence
<220> FEATURE:
<223> OTHER INFORMATION: synthetic amino acid sequence
<220> FEATURE:
<221> NAME/KEY: MISC_FEATURE
<222> LOCATION: (2)..(2)
<223> OTHER INFORMATION: the amino acid in this position can be any
      amino acid

<400> SEQUENCE: 25

Phe Xaa Tyr Glu Asn Glu
1               5

<210> SEQ ID NO 26
<211> LENGTH: 7
<212> TYPE: PRT
<213> ORGANISM: Artificial sequence
<220> FEATURE:
```

<223> OTHER INFORMATION: synthetic amino acid sequence

<400> SEQUENCE: 26

Phe Cys Tyr Glu Asn Glu Val
1               5

<210> SEQ ID NO 27
<211> LENGTH: 18
<212> TYPE: PRT
<213> ORGANISM: Artificial sequence
<220> FEATURE:
<223> OTHER INFORMATION: synthetic amino acid sequence

<400> SEQUENCE: 27

Met Thr Glu Thr Leu Pro Pro Val Thr Glu Ser Ala Val Ala Leu Gln
1               5                   10                  15

Ala Glu

<210> SEQ ID NO 28
<211> LENGTH: 238
<212> TYPE: PRT
<213> ORGANISM: Artificial sequence
<220> FEATURE:
<223> OTHER INFORMATION: synthetic amino acid sequence

<400> SEQUENCE: 28

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

US 10,974,064 B2

OPTOGENETIC CONTROL OF BEHAVIORAL STATE

CROSS-REFERENCE

This application claims the benefit of U.S. Provisional Patent Application Nos. 61/789,961, filed Mar. 15, 2013, and 61/808,965, filed Apr. 5, 2013, which applications are incorporated herein by reference in their entirety.

INCORPORATION BY REFERENCE OF SEQUENCE LISTING PROVIDED AS A TEXT FILE

A Sequence Listing is provided herewith as a text file, "STAN-1017WO SeqList_ST25.txt" created on Mar. 6, 2014 and having a size of 51 KB. The contents of the text file are incorporated by reference herein in their entirety.

INTRODUCTION

Animals encounter environmental conditions that require rapid switching among different behavioral states to increase the likelihood of survival and reproduction. Such states consist of a constellation of changes coordinated by distinct modalities of nervous system output, and understanding this behavioral-state assembly from diverse features is of fundamental interest. A well-studied example is the fearful state, wherein the amygdala is thought to modulate various aspects of fear expression via distinct targets. However, it has not yet been possible to test if specific diverging projections causally recruit distinct features to assemble a behavioral state.

"Optogenetics" refers to the combination of genetic and optical methods used to control specific events in targeted cells of living tissue, even within freely moving mammals and other animals, with the temporal precision (millisecond-timescale) needed to keep pace with functioning intact biological systems.

SUMMARY

The present disclosure provides methods of modulating a feature of a behavioral state. The methods involve inhibiting or activating the activity of a bed nucleus of stria terminalis (BNST) neuron, a BNST subnucleus, or a neuronal output to or from a BNST neuron.

The present disclosure features a method of modulating a feature of a behavioral disorder, the method comprising inhibiting or activating the activity of a bed nucleus of stria terminalis (BNST) neuron, a BNST subnucleus, or a neuronal output to or from a BNST neuron, wherein the feature is a behavioral feature or a physiological feature. In some cases, the behavioral state is anxiety. In some cases, the feature is respiratory rate, risk avoidance, or aversiveness. In some cases, modulating comprises inhibiting a BNST neuron, wherein said inhibiting is anxiolytic. In some cases, modulating comprises inhibiting the oval nucleus of a BNST, wherein said inhibiting is anxiolytic and reduces respiratory rate. In some cases, modulating comprises activating a basolateral amygdala (BLA) input to a BNST neuron by activating a BLA pyramidal neuron, wherein said activating reduces risk avoidance and reduces respiratory rate. In some cases, modulating comprises stimulating an anterodorsal BNST neuron projection to the lateral hypothalamus, wherein said stimulating reduces risk avoidance, and has substantially no effect on respiratory rate. In some cases, the modulating comprises activating an anterodorsal BNST neuron projection to the parabrachial nucleus, wherein said activating reduces respiratory rate, and has substantially no effect on risk avoidance behavior. In some cases, the modulating comprises activating an anterodorsal BNST neuron projection to the ventral tegmental area, wherein said activating results in normalized behavior. In some cases, the modulating comprises expressing an excitatory light-responsive protein or an inhibitory light-responsive protein in the BNST neuron, a BNST subnucleus, or the neuronal output to or from a BNST neuron; and exposing the BNST neuron, a BNST subnucleus, or the neuronal output to or from a BNST neuron to light of a wavelength to which the light-responsive protein responds. In some cases, the light responsive protein comprises an amino acid sequence having at least about 90% amino acid sequence identity to an amino acid sequence depicted in FIGS. 28A-D.

The present disclosure features a non-human animal model of a behavioral disorder, wherein a light-responsive protein is expressed in a bed nucleus of stria terminalis (BNST) neuron, a BNST subnucleus, or a neuronal output to or from a BNST neuron, and wherein exposure of the BNST neuron, BNST subnucleus, or neuronal output to or from a BNST neuron to light induces behavioral and/or physiological features of a behavioral disorder. In some cases, the light responsive protein comprises an amino acid sequence having at least about 90% amino acid sequence identity to an amino acid sequence depicted in FIGS. 28A-D. In some cases, an excitatory light-responsive protein is expressed in a BNST somata, and exposure of the BNST neuron to light of a wavelength to which the light-responsive protein responds results in increased anxiety. In some cases, the excitatory light-responsive protein comprises an amino acid sequence having at least about 90% amino acid sequence identity to a ChR2 polypeptide. In some cases, an excitatory light-responsive protein is expressed in an oval nucleus of a BNST, and exposure of the BNST neuron to light of a wavelength to which the light-responsive protein responds results in increased anxiety and increased respiratory rate. In some cases, the excitatory light-responsive protein comprises an amino acid sequence having at least about 90% amino acid sequence identity to a ChR2 polypeptide. In some cases, an inhibitory light-responsive protein is expressed in a basolateral amygdala (BLA) pyramidal neuron input to an anterodorsal BNST (adBNST) neuron; and exposure of the BLA pyramidal neuron input to an adBNST to light of a wavelength to which the light-responsive protein responds results in increased anxiety and increased respiratory rate. In some cases, the inhibitory light-responsive protein comprises an amino acid sequence having at least about 90% amino acid sequence identity to an NpHR polypeptide.

The present disclosure provides a method of identifying a candidate agent for ameliorating a behavioral or physiological feature of a behavioral disorder, the method comprising: a) administering a test agent to a non-human animal according to the present disclosure and b) determining the effect of the test agent on a behavioral or physiological feature of said behavioral disorder exhibited by said non-human animal when the light-responsive opsin polypeptide is activated by light, wherein a test agent that ameliorates a behavioral or physiological feature is considered a candidate agent for ameliorating a behavioral or physiological feature of a behavioral disorder. In some cases, the non-human animal model expresses an excitatory light-responsive polypeptide in a BNST somata, and exposure of the BNST neuron to light of a wavelength to which the light-responsive protein responds results in increased anxiety, and wherein a test agent is assessed for its effect on anxiety. In some cases, the non-human animal model expresses an excitatory light-responsive protein is expressed in an oval nucleus of a BNST, and exposure of the BNST neuron to light of a wavelength to which the light-responsive protein responds results in increased anxiety and increased respiratory rate, and wherein a test agent is assessed for its effect on anxiety and/or respiratory rate. In some cases, the non-human animal model expresses wherein an inhibitory light-responsive protein is expressed in a basolateral amygdala (BLA) pyramidal neuron input to an anterodorsal BNST (adBNST) neuron; and exposure of the BLA pyramidal neuron input to an adBNST to light of a wavelength to which the light-responsive protein responds results in increased anxiety and increased respiratory rate, and wherein a test agent is assessed for its effect on anxiety and/or respiratory rate.

BRIEF DESCRIPTION OF THE DRAWINGS

FIGS. 7A-F depict the effect of optogenetic stimulation of BNST somata on anxiety-related behavior.

FIGS. 28A-D provide amino acid sequences of various light-responsive proteins.

DEFINITIONS

Figure 1:
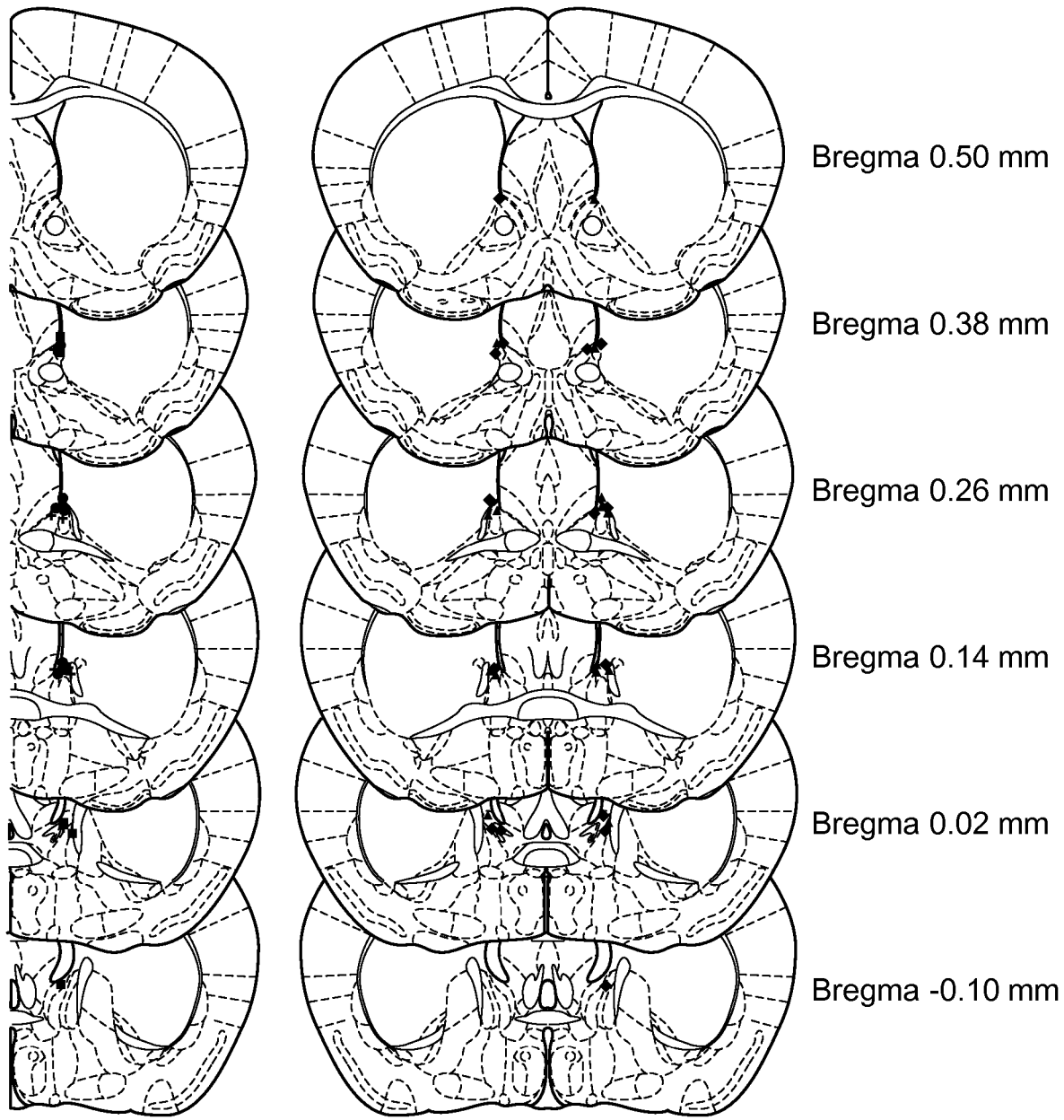
FIG. 1 depicts placement of fiberoptics and cannula guides targeting the BNST.

An "individual" can be a mammal, including a human. Mammals include, but are not limited to, ungulates, canines, felines, bovines, ovines, non-human primates, lagomorphs, and rodents (e.g., mice and rats). In one aspect, an individual is a human. In another aspect, an individual is a non-human mammal.

Amino acid substitutions in a native protein sequence may be "conservative" or "non-conservative" and such substituted amino acid residues may or may not be one encoded by the genetic code. A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which the amino acid residue is replaced with an amino acid residue having a chemically different side chain (i.e., replacing an amino acid having a basic side chain with an amino acid having an aromatic side chain). The standard twenty amino acid "alphabet" is divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and side chains having aromatic groups (e.g., tyrosine, phenylalanine, tryptophan, histidine).

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including clinical results. For purposes of this invention, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a light-activated polypeptide" includes a plurality of such light-activated polypeptides and reference to "the anxiety disorder" includes reference to one or more anxiety disorders and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a method of modulating a feature of a behavioral state, the method generally involving inhibiting or activating the activity of a bed nucleus of stria terminalis (BNST) neuron, a BNST subnucleus, or a neuronal output to or from a BNST neuron. In some cases, inhibiting or activating a BNST neuron, a BNST subnucleus, or a neuronal output to or from a BNST neuron involves expressing a light-responsive polypeptide in the BNST neuron, the BNST subnucleus, or the neuronal output to or from the BNST neuron; and exposing the neuron, subnucleus, or neuronal output to light.

Features of a behavioral state or be behavioral disorder include physiological features and behavioral features. Physiological features can include fear, anxiety, and the like. Physiological features can include respiratory rate (e.g., increased respiratory rate); heart rate (e.g., increased heart rate); appetite (e.g., loss of appetite); and the like. Behavioral states and disorders are well known in the art and include, e.g., depression, anxiety disorders, and other behavioral disorders and states.

In some cases, a light-responsive polypeptide is expressed in a BNST somata. In other cases, a light-responsive polypeptide is expressed in a BNST projection.

In some cases, an inhibitory light-responsive polypeptide is expressed in a BNST neuron; and exposure of the neuron to light in a wavelength range to which the inhibitory light-responsive polypeptide responds results in a reduction in one or more features of a pathological behavioral state. For example, in some cases, an inhibitory light-responsive polypeptide is expressed in a BNST neuron; and exposure of the neuron to light in a wavelength range to which the inhibitory light-responsive polypeptide responds results in one or more of a reduction of anxiety, a reduction in risk aversion, etc.

In some cases, an inhibitory light-responsive polypeptide is expressed in an oval nucleus of the BNST (ovBNST); and exposure of the neuron to light in a wavelength range to which the inhibitory light-responsive polypeptide responds results in a reduction in one or more features of a pathological behavioral state. For example, in some cases, an inhibitory light-responsive polypeptide is expressed in an ovBNST; and exposure of the neuron to light in a wavelength range to which the inhibitory light-responsive polypeptide responds results in one or more of a reduction of anxiety, a reduction in risk aversion, and a reduction in respiratory rate.

In some cases, an excitatory light-responsive polypeptide is expressed in a basolateral amygdala (BLA) pyramidal neuron input to an anterodorsal (ad) BNST (adBNST); and exposure of the BLA pyramidal neuron input to the adBNST to light in a wavelength range to which the excitatory light-responsive polypeptide responds results in a reduction in one or more features of a pathological behavioral state. For example, in some cases, an excitatory light-responsive polypeptide is expressed in a BLA pyramidal neuron input to an adBNST; and exposure of the BLA pyramidal neuron input to the adBNST to light in a wavelength range to which the excitatory light-responsive polypeptide responds results in one or more of a reduction of anxiety, a reduction in risk aversion, and a reduction in respiratory rate.

In some cases, an excitatory light-responsive polypeptide is expressed in an adBNST neuron projection to the lateral hypothalamus (LH); and exposure of the adBNST neuron projection to the LH to light in a wavelength range to which the excitatory light-responsive polypeptide responds results in a reduction in one or more adverse behavioral features of a pathological behavioral state, e.g., a reduction in risk avoidance.

In some cases, an excitatory light-responsive polypeptide is expressed in an adBNST neuron output to the parabrachial (PB) nucleus; and exposure of the adBNST neuron output to the PB to light in a wavelength range to which the excitatory light-responsive polypeptide responds results in a reduction in one or more physiological features of a pathological behavioral state, e.g., reduction in respiratory rate.

In some cases, an excitatory light-responsive polypeptide is expressed in an adBNST neuron output to the ventral tegmental area (VTA); and exposure of the adBNST neuron projection to the VTA to light in a wavelength range to which the excitatory light-responsive polypeptide responds results in an improvement in one or more behavioral features of a pathological behavioral state.

Light-Responsive Opsin Proteins

Provided herein are optogenetic-based methods for selectively hyperpolarizing or depolarizing the neurons involved in features of anxiety, using light-responsive opsin proteins to effectively modulate anxiety features in individuals afflicted with an anxiety disorder. Optogenetics refers to the combination of genetic and optical methods used to control specific events in targeted cells of living tissue, even within freely moving mammals and other animals, with the temporal precision (millisecond-timescale) needed to keep pace with functioning intact biological systems. Optogenetics requires the introduction of fast light-responsive channel or pump proteins to the plasma membranes of target neuronal cells that allow temporally precise manipulation of neuronal membrane potential while maintaining cell-type resolution through the use of specific targeting mechanisms. Any microbial opsin that can be used to promote neural cell membrane hyperpolarization or depolarization in response to light may be used.

For example, the Halorhodopsin family of light-responsive chloride pumps (e.g., NpHR, NpHR2.0, NpHR3.0, NpHR3.1) and the GtR3 proton pump can be used to promote neural cell membrane hyperpolarization in response to light. As another example, eArch (a proton pump) can be used to promote neural cell membrane hyperpolarization in response to light. As another example, an ArchT opsin protein or a Mac opsin protein can be used to promote neural cell membrane hyperpolarization in response to light.

Additionally, members of the Channelrhodopsin family of light-responsive cation channel proteins (e.g., ChR2, SFOs, SSFOs, C1V1s) can be used to promote neural cell membrane depolarization or depolarization-induced synaptic depletion in response to a light stimulus.

Enhanced Intracellular Transport Amino Acid Motifs

The present disclosure provides for the modification of light-responsive opsin proteins expressed in a cell by the addition of one or more amino acid sequence motifs which enhance transport to the plasma membranes of mammalian cells. Light-responsive opsin proteins having components derived from evolutionarily simpler organisms may not be expressed or tolerated by mammalian cells or may exhibit impaired subcellular localization when expressed at high levels in mammalian cells. Consequently, in some embodiments, the light-responsive opsin proteins expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive protein transport to the plasma membranes of mammalian cells can be fused to the N-terminus, the C-terminus, or to both the N- and C-terminal ends of the light-responsive protein. Optionally, the light-responsive protein and the one or more amino acid sequence motifs may be separated by a linker. In some embodiments, the light-responsive protein can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:16).

Trafficking sequences that are suitable for use can comprise an amino acid sequence having 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:16)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Signal sequences that are suitable for use can comprise an amino acid sequence having 90%, 91%, 92%, 93%, 94%, 95%, 96%, 97%, 98%, 99%, or 100%, amino acid sequence identity to an amino acid sequence such as one of the following:

1) the signal peptide of hChR2 (e.g., MDYGGALSAVGRELLFVTNPVVVNGS (SEQ ID NO:17))

2) the 132 subunit signal peptide of the neuronal nicotinic acetylcholine receptor (e.g., MAGHSNSMALFSFSLLWLCSGVLGTEF (SEQ ID NO:18));

3) a nicotinic acetylcholine receptor signal sequence (e.g., MGLRALMLWLLAAAGLVRESLQG (SEQ ID NO:19)); and 4) a nicotinic acetylcholine receptor signal sequence (e.g., MRGTPLLLVVSLFSLLQD (SEQ ID NO:20)).

A signal sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Endoplasmic reticulum (ER) export sequences that are suitable for use in a modified opsin of the present disclosure include, e.g., VXXSL (SEQ ID NO:21) (where X is any amino acid) (e.g., VKESL (SEQ ID NO:22); VLGSL (SEQ ID NO:23); etc.); NANSFCYENEVALTSK (SEQ ID NO:24); FXYENE (SEQ ID NO:25) (where X is any amino acid), e.g., FCYENEV (SEQ ID NO:26); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In some embodiments, the signal peptide sequence in the protein can be deleted or substituted with a signal peptide sequence from a different protein.

Inhibitory Light-Responsive Opsin Proteins

In some embodiments, a subject method for modulating a behavioral feature involves use of an inhibitory light-responsive opsin protein. Inhibitory light-responsive opsin proteins include polypeptides having sequence similarity (e.g., at least about 85%, 90%, 91%, 92%, 93%, 94%, 95%, 96%, 97%, 98%, 99%, or 100% amino acid sequence identity) to one of SEQ ID NOs:1, 2, 3, 4, 12, 13, 14, and 15 (FIG. 28).

Light-Responsive Chloride Pumps

In some aspects of the methods provided herein, one or more members of the Halorhodopsin family of light-responsive chloride pumps are expressed on the plasma membranes of neurons in the BNST, e.g., in a BNST subregion such as in the ov-BNST.

In some aspects, said one or more light-responsive chloride pump proteins expressed on the plasma membranes of the neurons described above can be derived from *Natronomonas pharaonis*. In some embodiments, the light-responsive chloride pump proteins can be responsive to amber light as well as red light and can mediate a hyperpolarizing current in the neuron when the light-responsive chloride pump proteins are illuminated with amber or red light. The wavelength of light which can activate the light-responsive chloride pumps can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the light-responsive chloride pump protein can hyperpolarize a neural membrane for at least about 90 minutes when exposed to a continuous pulse of light. In some embodiments, the light-responsive chloride pump protein can comprise an amino acid sequence at least about 85%, 90%, 91%, 92%, 93%, 94%, 95%, 96%, 97%, 98%, 99%, or 100% identical to the sequence shown in SEQ ID NO: 1. Additionally, the light-responsive chloride pump protein can comprise substitutions, deletions, and/or insertions introduced into a native amino acid sequence to increase or decrease sensitivity to light, increase or decrease sensitivity to particular wavelengths of light, and/or increase or decrease the ability of the light-responsive protein to regulate the polarization state of the plasma membrane of the cell. In some embodiments, the light-responsive chloride pump protein contains one or more conservative amino acid substitutions. In some embodiments, the light-responsive protein contains one or more non-conservative amino acid substitutions. The light-responsive protein comprising substitutions, deletions, and/or insertions introduced into the native amino acid sequence suitably retains the ability to hyperpolarize the plasma membrane of a neuronal cell in response to light.

Additionally, in other aspects, the light-responsive chloride pump protein can comprise a core amino acid sequence at least about 85%, 90%, 91%, 92%, 93%, 94%, 95%, 96%, 97%, 98%, 99%, or 100% identical to the sequence shown in SEQ ID NO: 1 and an endoplasmic reticulum (ER) export signal. This ER export signal can be fused to the C-terminus of the core amino acid sequence or can be fused to the N-terminus of the core amino acid sequence. In some embodiments, the ER export signal is linked to the core amino acid sequence by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal can comprise the amino acid sequence FXYENE (SEQ ID NO:25), where X can be any amino acid. In another embodiment, the ER export signal can comprise the amino acid sequence VXXSL (SEQ ID NO:21), where X can be any amino acid. In some embodiments, the ER export signal can comprise the amino acid sequence FCYENEV (SEQ ID NO:26).

Endoplasmic reticulum (ER) export sequences that are suitable for use in a modified opsin of the present disclosure include, e.g., VXXSL (SEQ ID NO:21) (where X is any amino acid) (e.g., VKESL (SEQ ID NO:22); VLGSL (SEQ ID NO:23); etc.); NANSFCYENEVALTSK (SEQ ID NO:24); FXYENE (where X is any amino acid) (SEQ ID NO:25), e.g., FCYENEV (SEQ ID NO:26); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In other aspects, the light-responsive chloride pump proteins described herein can comprise a light-responsive protein expressed on the cell membrane, wherein the protein comprises a core amino acid sequence at least about 90%, 91%, 92%, 93%, 94%, 95%, 96%, 97%, 98%, 99%, or 100% identical to the sequence shown in SEQ ID NO: 1 and a trafficking signal (e.g., which can enhance transport of the light-responsive chloride pump protein to the plasma membrane). The trafficking signal may be fused to the C-terminus of the core amino acid sequence or may be fused to the N-terminus of the core amino acid sequence. In some embodiments, the trafficking signal can be linked to the core amino acid sequence by a linker which can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:16).

In some aspects, the light-responsive chloride pump protein can comprise a core amino acid sequence at least about 90%, 91%, 92%, 93%, 94%, 95%, 96%, 97%, 98%, 99%, or 100% identical to the sequence shown in SEQ ID NO:1 and at least one (such as one, two, three, or more) amino acid sequence motifs which enhance transport to the plasma membranes of mammalian cells selected from the group consisting of an ER export signal, a signal peptide, and a membrane trafficking signal. In some embodiments, the light-responsive chloride pump protein comprises an N-terminal signal peptide, a C-terminal ER Export signal, and a C-terminal trafficking signal. In some embodiments, the C-terminal ER Export signal and the C-terminal trafficking signal can be linked by a linker. The linker can comprise any of about 5, 10, 20, 30, 40, 50, 75, 100, 125, 150, 175, 200, 225, 250, 275, 300, 400, or 500 amino acids in length. The linker can also further comprise a fluorescent protein, for example, but not limited to, a yellow fluorescent protein, a red fluorescent protein, a green fluorescent protein, or a cyan fluorescent protein. In some embodiments the ER Export signal can be more C-terminally located than the trafficking signal. In other embodiments the trafficking signal is more C-terminally located than the ER Export signal. In some embodiments, the signal peptide comprises the amino acid sequence MTETLPPVTESAVALQAE (SEQ ID NO:27). In another embodiment, the light-responsive chloride pump protein comprises an amino acid sequence at least 95% identical to SEQ ID NO:2.

Moreover, in other aspects, the light-responsive chloride pump proteins can comprise a core amino acid sequence at least about 90%, 91%, 92%, 93%, 94%, 95%, 96%, 97%, 98%, 99%, or 100% identical to the sequence shown in SEQ ID NO: 1, wherein the N-terminal signal peptide of SEQ ID NO:1 is deleted or substituted. In some embodiments, other signal peptides (such as signal peptides from other opsins) can be used. The light-responsive protein can further comprise an ER transport signal and/or a membrane trafficking signal described herein. In some embodiments, the light-responsive chloride pump protein comprises an amino acid sequence at least 95% identical to SEQ ID NO:3.

In some embodiments, the light-responsive opsin protein is a NpHR opsin protein comprising an amino acid sequence at least 95%, at least 96%, at least 97%, at least 98%, at least 99% or 100% identical to the sequence shown in SEQ ID NO:1. In some embodiments, the NpHR opsin protein further comprises an endoplasmic reticulum (ER) export signal and/or a membrane trafficking signal. For example, the NpHR opsin protein comprises an amino acid sequence at least 95% identical to the sequence shown in SEQ ID NO:1 and an endoplasmic reticulum (ER) export signal. In some embodiments, the amino acid sequence at least 95% identical to the sequence shown in SEQ ID NO:1 is linked to the ER export signal through a linker. In some embodiments, the ER export signal comprises the amino acid sequence FXYENE (SEQ ID NO:25), where X can be any amino acid. In another embodiment, the ER export signal comprises the amino acid sequence VXXSL, where X can be any amino acid. In some embodiments, the ER export signal comprises the amino acid sequence FCYENEV (SEQ ID NO:26). In some embodiments, the NpHR opsin protein comprises an amino acid sequence at least 95% identical to the sequence shown in SEQ ID NO:1, an ER export signal, and a membrane trafficking signal. In other embodiments, the NpHR opsin protein comprises, from the N-terminus to the C-terminus, the amino acid sequence at least 95% identical to the sequence shown in SEQ ID NO:1, the ER export signal, and the membrane trafficking signal. In other embodiments, the NpHR opsin protein comprises, from the N-terminus to the C-terminus, the amino acid sequence at least 95% identical to the sequence shown in SEQ ID NO:1, the membrane trafficking signal, and the ER export signal. In some embodiments, the membrane trafficking signal is derived from the amino acid sequence of the human inward rectifier potassium channel Kir2.1. In some embodiments, the membrane trafficking signal comprises the amino acid sequence K S R I T S E G E Y I P L D Q I D I N V (SEQ ID NO:16). In some embodiments, the membrane trafficking signal is linked to the amino acid sequence at least 95% identical to the sequence shown in SEQ ID NO:1 by a linker. In some embodiments, the membrane trafficking signal is linked to the ER export signal through a linker. The linker may comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the light-responsive opsin protein further comprises an N-terminal signal peptide. In some embodiments, the light-responsive opsin protein comprises the amino acid sequence of SEQ ID NO:2. In some embodiments, the light-responsive opsin protein comprises the amino acid sequence of SEQ ID NO:3.

Also provided herein are polynucleotides encoding any of the light-responsive chloride ion pump proteins described herein, such as a light-responsive protein comprising a core amino acid sequence at least about 90%, 91%, 92%, 93%, 94%, 95%, 96%, 97%, 98%, 99%, or 100% identical to the sequence shown in SEQ ID NO:1, an ER export signal, and a membrane trafficking signal. In another embodiment, the polynucleotides comprise a sequence which encodes an amino acid at least 95% identical to SEQ ID NO:2 and SEQ ID NO:3. The polynucleotides may be in an expression vector (such as, but not limited to, a viral vector described herein). The polynucleotides may be used for expression of the light-responsive chloride ion pump proteins.

Further disclosure related to light-responsive chloride pump proteins can be found in U.S. Patent Application Publication Nos: 2009/0093403 and 2010/0145418 as well as in International Patent Application No: PCT/US2011/028893, the disclosures of each of which are hereby incorporated by reference in their entireties.

Light-Responsive Proton Pumps

In some aspects of the methods provided herein, one or more light-responsive proton pumps are expressed on the plasma membranes of a BNST neuron, a BNST subnucleus, or a neuronal output to or from a BNST neuron. In some embodiments, the light-responsive proton pump protein can be responsive to blue light and can be derived from *Guillardia theta*, wherein the proton pump protein can be capable of mediating a hyperpolarizing current in the cell when the cell is illuminated with blue light. The light can have a wavelength between about 450 and about 495 nm or can have a wavelength of about 490 nm. In another embodiment, the light-responsive proton pump protein can comprise an amino acid sequence at least about 90%, 91%, 92%, 93%, 94%, 95%, 96%, 97%, 98%, 99%, or 100% identical to the sequence shown in SEQ ID NO:4. The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to hyperpolarize the plasma membrane of a neuronal cell in response to light.

In other aspects of the methods disclosed herein, the light-responsive proton pump protein can comprise a core amino acid sequence at least about 90%, 91%, 92%, 93%, 94%, 95%, 96%, 97%, 98%, 99%, or 100% identical to the sequence shown in SEQ ID NO:4 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive proton pump proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4. The polynucleotides may be used for expression of the light-responsive protein in a BNST neuron, a BNST subnucleus, or a neuronal output to or from a BNST neuron.

Further disclosure related to light-responsive proton pump proteins can be found in International Patent Application No. PCT/US2011/028893, the disclosure of which is hereby incorporated by reference in its entirety.

In some embodiments, the light-responsive proton pump protein can be responsive to green or yellow light and can be derived from *Halorubrum sodomense*, wherein the proton pump protein can be capable of mediating a hyperpolarizing current in the cell when the cell is illuminated with green or yellow light. The light can have a wavelength between about 560 and about 570 nm or can have a wavelength of about 566 nm. In another embodiment, the light-responsive proton pump protein can comprise an amino acid sequence at least about 90%, 91%, 92%, 93%, 94%, 95%, 96%, 97%, 98%, 99%, or 100% identical to the sequence shown in SEQ ID NO:12. The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to hyperpolarize the plasma membrane of a neuronal cell in response to light.

In other aspects of the methods disclosed herein, the light-responsive proton pump protein can comprise a core amino acid sequence at least about 90%, 91%, 92%, 93%, 94%, 95%, 96%, 97%, 98%, 99%, or 100% identical to the sequence shown in SEQ ID NO:12 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive proton pump proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:12. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:12. The polynucleotides may be used for expression of the light-responsive protein in neural cells (e.g. a BNST neuron, a BNST subnucleus, or a neuronal output to or from a BNST neuron).

Excitatory Light-Responsive Opsin Proteins

In some embodiments, a subject method for modulating a behavioral feature involves use of an excitatory light-responsive opsin protein. Excitatory light-responsive opsin proteins include polypeptides having sequence similarity (e.g., at least about 85%, 90%, 91%, 92%, 93%, 94%, 95%, 96%, 97%, 98%, 99%, or 100% amino acid sequence identity) to one of SEQ ID NOs:5, 6, 7, 8, 9, 10, and 11 (FIG. 28).

Light-Responsive Cation Channel Proteins

In some aspects of the methods provided herein, one or more light-responsive cation channels can be expressed on the plasma membranes of a BNST neuron, a BNST subnucleus, or a neuronal output to or from a BNST neuron.

In some aspects, the light-responsive cation channel protein can be derived from *Chlamydomonas reinhardtii*, wherein the cation channel protein can be capable of mediating a depolarizing current in the cell when the cell is illuminated with light. In another embodiment, the light-responsive cation channel protein can comprise an amino acid sequence at least about 90%, 91%, 92%, 93%, 94%, 95%, 96%, 97%, 98%, 99%, or 100% identical to the sequence shown in SEQ ID NO:5 (ChR2). The light used to activate the light-responsive cation channel protein derived from *Chlamydomonas reinhardtii* can have a wavelength between about 460 and about 495 nm or can have a wavelength of about 480 nm. Additionally, the light can have an intensity of at least about 100 Hz. In some embodiments, activation of the light-responsive cation channel derived from *Chlamydomonas reinhardtii* with light having an intensity of 100 Hz can cause depolarization-induced synaptic depletion of the neurons expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to depolarize the plasma membrane of a BNST neuron, a BNST subnucleus, or a neuronal output to or from a BNST neuron in response to light.

In some embodiments, the light-responsive cation channel comprises a T159C substitution of the amino acid sequence set forth in SEQ ID NO:5. In some embodiments, the light-responsive cation channel comprises a L132C substitution of the amino acid sequence set forth in SEQ ID NO:5. In some embodiments, the light-responsive cation channel comprises an E123T substitution of the amino acid sequence set forth in SEQ ID NO:5. In some embodiments, the light-responsive cation channel comprises an E123A substitution of the amino acid sequence set forth in SEQ ID NO:5. In some embodiments, the light-responsive cation channel comprises a T159C substitution and an E123T substitution of the amino acid sequence set forth in SEQ ID NO:5. In some embodiments, the light-responsive cation channel comprises a T159C substitution and an E123A substitution of the amino acid sequence set forth in SEQ ID NO:5. In some embodiments, the light-responsive cation channel comprises a T159C substitution, an L132C substitution, and an E123T substitution of the amino acid sequence set forth in SEQ ID NO:5. In some embodiments, the light-responsive cation channel comprises a T159C substitution, an L132C substitution, and an E123A substitution of the amino acid sequence set forth in SEQ ID NO:5. In some embodiments, the light-responsive cation channel comprises an L132C substitution and an E123T substitution of the amino acid sequence set forth in SEQ ID NO:5. In some embodiments, the light-responsive cation channel comprises an L132C substitution and an E123A substitution of the amino acid sequence set forth in SEQ ID NO:5.

Further disclosure related to light-responsive cation channel proteins can be found in U.S. Patent Application Publication No. 2007/0054319 and International Patent Application Publication Nos. WO 2009/131837 and WO 2007/024391, the disclosures of each of which are hereby incorporated by reference in their entireties.

Step Function Opsins and Stabilized Step Function Opsins

In other embodiments, the light-responsive cation channel protein can be a step function opsin (SFO) protein or a stabilized step function opsin (SSFO) protein that can have specific amino acid substitutions at key positions throughout the retinal binding pocket of the protein. In some embodiments, the SFO protein can have a mutation at amino acid residue C128 of SEQ ID NO:5. In other embodiments, the SFO protein has a C128A mutation in SEQ ID NO:5. In other embodiments, the SFO protein has a C128S mutation in SEQ ID NO:5. In another embodiment, the SFO protein has a C128T mutation in SEQ ID NO:5. In some embodiments, the SFO protein can comprise an amino acid sequence at least about 90%, 91%, 92%, 93%, 94%, 95%, 96%, 97%, 98%, 99%, or 100% identical to the sequence shown in SEQ ID NO:6.

In some embodiments, the SSFO protein can have a mutation at amino acid residue D156 of SEQ ID NO:5. In other embodiments, the SSFO protein can have a mutation at both amino acid residues C128 and D156 of SEQ ID NO:5. In one embodiment, the SSFO protein has an C128S and a D156A mutation in SEQ ID NO:5. In another embodiment, the SSFO protein can comprise an amino acid sequence at least about 90%, 91%, 92%, 93%, 94%, 95%, 96%, 97%, 98%, 99%, or 100% identical to the sequence shown in SEQ ID NO:7. In another embodiment, the SSFO protein can comprise a C128T mutation in SEQ ID NO:5. In some embodiments, the SSFO protein comprises C128T and D156A mutations in SEQ ID NO:5.

In some embodiments the SFO or SSFO proteins provided herein can be capable of mediating a depolarizing current in the cell when the cell is illuminated with blue light. In other embodiments, the light can have a wavelength of about 445 nm. Additionally, the light can have an intensity of about 100 Hz. In some embodiments, activation of the SFO or SSFO protein with light having an intensity of 100 Hz can cause depolarization-induced synaptic depletion of the neurons expressing the SFO or SSFO protein. In some embodiments, each of the disclosed step function opsin and stabilized step function opsin proteins can have specific properties and characteristics for use in depolarizing the membrane of a neuronal cell in response to light.

Further disclosure related to SFO or SSFO proteins can be found in International Patent Application Publication No. WO 2010/056970 and U.S. Provisional Patent Application Nos. 61/410,704 and 61/511,905, the disclosures of each of which are hereby incorporated by reference in their entireties.

C1V1 Chimeric Cation Channels

In other embodiments, the light-responsive cation channel protein can be a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments, the C1V1 protein can further comprise a replacement within the intracellular loop domain located between the second and third transmembrane helices of the chimeric light responsive protein, wherein at least a portion of the intracellular loop domain is replaced by the corresponding portion from ChR1. In another embodiment, the portion of the intracellular loop domain of the C1V1 chimeric protein can be replaced with the corresponding portion from ChR1 extending to amino acid residue A145 of the ChR1. In other embodiments, the C1V1 chimeric protein can further comprise a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1. In other embodiments, the C1V1 chimeric protein can comprise an amino acid sequence at least about 90%, 91%, 92%, 93%, 94%, 95%, 96%, 97%, 98%, 99%, or 100% identical to the sequence shown in SEQ ID NO:8.

In some embodiments, the C1V1 protein can mediate a depolarizing current in the cell when the cell is illuminated with green light. In other embodiments, the light can have a wavelength of between about 540 nm to about 560 nm. In some embodiments, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, the light can have an intensity of about 100 Hz. In some embodiments, activation of the C1V1 chimeric protein with light having an intensity of 100 Hz can cause depolarization-induced synaptic depletion of the neurons expressing the C1V1 chimeric protein. In some embodiments, the disclosed C1V1 chimeric protein can have specific properties and characteristics for use in depolarizing the membrane of a BNST neuron, a BNST subnucleus, or a neuronal output to or from a BNST neuron in response to light.

C1V1 Chimeric Mutant Variants

In some aspects, the present disclosure provides polypeptides comprising substituted or mutated amino acid sequences, wherein the mutant polypeptide retains the characteristic light-activatable nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells.

Accordingly, provided herein are C1V1 chimeric light-responsive opsin proteins that can have specific amino acid substitutions at key positions throughout the retinal binding pocket of the VChR1 portion of the chimeric polypeptide. In some embodiments, the C1V1 protein can have a mutation at amino acid residue E122 of SEQ ID NO:7. In some embodiments, the C1V1 protein can have a mutation at amino acid residue E162 of SEQ ID NO:7. In other embodiments, the C1V1 protein can have a mutation at both amino acid residues E162 and E122 of SEQ ID NO:7. In other embodiments, the C1V1 protein can comprise an amino acid sequence at least about 90%, 91%, 92%, 93%, 94%, 95%, 96%, 97%, 98%, 99%, or 100% identical to the sequence shown in SEQ ID NO:9, SEQ ID NO:10, or SEQ ID NO:11. In some embodiments, each of the disclosed mutant C1V1 chimeric proteins can have specific properties and characteristics for use in depolarizing the membrane of a BNST neuron, a BNST subnucleus, or a neuronal output to or from a BNST neuron in response to light.

In some aspects, the C1V1-E122 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In other embodiments, the C1V1-E122 mutant chimeric protein can mediate a depolarizing current in the cell when the cell is illuminated with red light. In some embodiments, the red light can have a wavelength of about 630 nm. In some embodiments, the C1V1-E122 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, the light can have an intensity of about 100 Hz. In some embodiments, activation of the C1V1-E122 mutant chimeric protein with light having an intensity of 100 Hz can cause depolarization-induced synaptic depletion of the neurons expressing the C1V1-E122 mutant chimeric protein. In some embodiments, the disclosed C1V1-E122 mutant chimeric protein can have specific properties and characteristics for use in depolarizing the membrane of a BNST neuron, a BNST subnucleus, or a neuronal output to or from a BNST neuron in response to light.

In other aspects, the C1V1-E162 mutant chimeric protein is capable of mediating a depolarizing current in the cell when the cell is illuminated with light. In some embodiments the light can be green light. In other embodiments, the light can have a wavelength of between about 535 nm to about 540 nm. In some embodiments, the light can have a wavelength of about 542 nm. In other embodiments, the light can have a wavelength of about 530 nm. In some embodiments, the C1V1-E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, the light can have an intensity of about 100 Hz. In some embodiments, activation of the C1V1-E162 mutant chimeric protein with light having an intensity of 100 Hz can cause depolarization-induced synaptic depletion of the neurons expressing the C1V1-E162 mutant chimeric protein. In some embodiments, the disclosed C1V1-E162 mutant chimeric protein can have specific properties and characteristics for use in depolarizing the membrane of a BNST neuron, a BNST subnucleus, or a neuronal output to or from a BNST neuron in response to light.

In yet other aspects, the C1V1-E122/E162 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In some embodiments, the C1V1-E122/E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. In some embodiments, the C1V1-E122/E162 mutant chimeric protein can exhibit less activation when exposed to violet light relative to C1V1 chimeric proteins lacking mutations at E122/E162 or relative to other light-responsive cation channel proteins. Additionally, the light can have an intensity of about 100 Hz. In some embodiments, activation of the C1V1-E122/E162 mutant chimeric protein with light having an intensity of 100 Hz can cause depolarization-induced synaptic depletion of the neurons expressing the C1V1-E122/E162 mutant chimeric protein. In some embodiments, the disclosed C1V1-E122/E162 mutant chimeric protein can have specific properties and characteristics for use in depolarizing the membrane of a BNST neuron, a BNST subnucleus, or a neuronal output to or from a BNST neuron in response to light.

Further disclosure related to C1V1 chimeric cation channels as well as mutant variants of the same can be found in U.S. Provisional Patent Application Nos. 61/410,736, 61/410,744, and 61/511,912, the disclosures of each of which are hereby incorporated by reference in their entireties.

Polynucleotides

The disclosure also provides polynucleotides comprising a nucleotide sequence encoding a light-responsive protein described herein. In some embodiments, the polynucleotide comprises an expression cassette. In some embodiments, the polynucleotide is a vector comprising the above-described nucleic acid. In some embodiments, the nucleic acid encoding a light-responsive protein of the disclosure is operably linked to a promoter. Promoters are well known in the art. Any promoter that functions in the host cell can be used for expression of the light-responsive opsin proteins and/or any variant thereof of the present disclosure. In one embodiment, the promoter used to drive expression of the light-responsive opsin proteins can be a promoter that is specific to a particular neuron. Initiation control regions or promoters, which are useful to drive expression of the light-responsive opsin proteins or variant thereof in a specific animal cell are numerous and familiar to those skilled in the art. Virtually any promoter capable of driving these nucleic acids can be used. In some embodiments, the promoter used to drive expression of the light-responsive protein can be the Thy1 promoter (See, e.g., Llewellyn, et al., 2010, *Nat. Med.,* 16(10):1161-1166). In other embodiments, the promoter used to drive expression of the light-responsive protein can be the EF1α promoter, a cytomegalovirus (CMV) promoter, the CAG promoter, a synapsin-I promoter (e.g., a human synapsin-I promoter), a human synuclein 1 promoter, a human Thy1 promoter, a calcium/calmodulin-dependent kinase II alpha (CAMKIIα) promoter, or any other promoter capable of driving expression of the light-responsive opsin proteins in a neuron of mammals.

Also provided herein are vectors comprising a nucleotide sequence encoding a light-responsive protein or any variant thereof described herein. The vectors that can be administered according to the present disclosure also include vectors comprising a nucleotide sequence which encodes an RNA (e.g., an mRNA) that when transcribed from the polynucleotides of the vector will result in the accumulation of light-responsive opsin proteins on the plasma membranes of target animal cells. Vectors which may be used, include, without limitation, lentiviral, HSV, adenoviral, and adeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, the vector is a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

AAV vectors may be prepared using standard methods in the art. Adeno-associated viruses of any serotype are suitable (see, e.g., Blacklow, pp. 165-174 of "*Parvoviruses and Human Disease*" J. R. Pattison, ed. (1988); Rose, *Comprehensive Virology* 3:1, 1974; P. Tattersall "The Evolution of Parvovirus Taxonomy" In *Parvoviruses* (JR Kerr, SF Cotmore. M E Bloom, R M Linden, CR Parrish, Eds.) p 5-14, Hudder Arnold, London, UK (2006); and DE Bowles, JE Rabinowitz, RJ Samulski "*The Genus Dependovirus*" (JR Kerr, SF Cotmore. M E Bloom, R M Linden, CR Parrish, Eds.) p 15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the present disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596,535, the disclosure of which is hereby incorporated by reference in its entirety.

Delivery of Light-Responsive Opsin Proteins

In some aspects, polynucleotides encoding the light-responsive opsin proteins disclosed herein (for example, an AAV vector) can be delivered directly to a BNST neuron, a BNST subnucleus, or a neuronal output to or from a BNST neuron with a needle, catheter, or related device, using neurosurgical techniques known in the art, such as by stereotactic injection (See, e.g., Stein et al., *J. Virol,* 73:34243429, 1999; Davidson et al., *PNAS,* 97:3428-3432, 2000; Davidson et al., *Nat. Genet.* 3:219-223, 1993; and Alisky & Davidson, *Hum. Gene Ther.* 11:2315-2329, 2000, the contents of each of which are hereby incorporated by reference herein in their entireties) or fluoroscopy.

Other methods to deliver the light-responsive opsin proteins to the neurons of interest can also be used, such as, but not limited to, transfection with ionic lipids or polymers, electroporation, optical transfection, impalefection, or via gene gun.

Light and Electrical Sources

In some aspects of the present disclosure, the light-responsive opsin proteins disclosed herein can be activated by an implantable light source (such as a light cuff) or an implantable electrode placed around or near neurons expressing the light-responsive opsin proteins. Electrode cuffs and electrodes surgically placed around or near neurons for use in electrical stimulation of those neurons are well known in the art (See, for example, U.S. Pat. Nos. 4,602,624, 7,142,925 and 6,600,956 as well as U.S. Patent Publication Nos. 2008/0172116 and 2010/0094372, the disclosures of each of which are hereby incorporated by reference in their entireties). The light sources (such as a light cuff) or electrodes of the present invention can be comprised of any useful composition or mixture of compositions, such as platinum or stainless steel, as are known in the art, and may be of any useful configuration for stimulating the light-responsive opsin proteins disclosed herein. The light source can be a fiberoptic light source.

The electrodes or implantable light source (such as a light cuff) may be placed around or near a neuron expressing a light-responsive protein.

In some embodiments, the implantable light source (such as a light cuff) does not completely surround the region containing a neuron expressing a light-responsive protein, but, rather, can have a U-shape. In another embodiment, the implantable light source can have an attachment arm that can be used to guide the implantable light source (such as a light cuff) to the neuronal region to be exposed to light. The attachment arm can be removed following implantation of the light source or can be left in place to fix the position of the light source in proximity to the neurons of interest.

The implantable light source (such as a light cuff) can comprise an inner body, the inner body having at least one means for generating light which is configured to a power source. In some embodiments, the power source can be an internal battery for powering the light-generating means. In another embodiment, the implantable light source can comprise an external antenna for receiving wirelessly transmitted electromagnetic energy from an external source for powering the light-generating means. The wirelessly transmitted electromagnetic energy can be a radio wave, a microwave, or any other electromagnetic energy source that can be transmitted from an external source to power the light-generating means of the implantable light source (such as a light cuff). In one embodiment, the light-generating means is controlled by an integrated circuit produced using semiconductor or other processes known in the art.

In some aspects, the light means can be a light emitting diode (LED). In some embodiments, the LED can generate blue and/or green light. In other embodiments, the LED can generate amber and/or yellow light. In some embodiments, several micro LEDs are embedded into the inner body of the implantable light source (such as a light cuff). In other embodiments, the light-generating means is a solid state laser diode or any other means capable of generating light. The light generating means can generate light having an intensity sufficient to activate the light-responsive opsin proteins expressed on the plasma membrane of the nerves in proximity to the light source (such as a light cuff). In some embodiments, the light-generating means produces light having an intensity of any of about 0.05 mW/mm$^2$, 0.1 mW/mm$^2$, 0.2 mW/mm$^2$, 0.3 mW/mm$^2$, 0.4 mW/mm$^2$, 0.5 mW/mm$^2$, about 0.6 mW/mm$^2$, about 0.7 mW/mm$^2$, about 0.8 mW/mm$^2$, about 0.9 mW/mm$^2$, about 1.0 mW/mm$^2$, about 1.1 mW/mm$^2$, about 1.2 mW/mm$^2$, about 1.3 mW/mm$^2$, about 1.4 mW/mm$^2$, about 1.5 mW/mm$^2$, about 1.6 mW/mm$^2$, about 1.7 mW/mm$^2$, about 1.8 mW/mm$^2$, about 1.9 mW/mm$^2$, about 2.0 mW/mm$^2$, about 2.1 mW/mm$^2$, about 2.2 mW/mm$^2$, about 2.3 mW/mm$^2$, about 2.4 mW/mm$^2$, about 2.5 mW/mm$^2$, about 3 mW/mm$^2$, about 3.5 mW/mm$^2$, about 4 mW/mm$^2$, about 4.5 mW/mm$^2$, about 5 mW/mm$^2$, about 5.5 mW/mm$^2$, about 6 mW/mm$^2$, about 7 mW/mm$^2$, about 8 mW/mm$^2$, about 9 mW/mm$^2$, or about 10 mW/mm$^2$, inclusive, including values in between these numbers. In other embodiments, the light-generating means produces light having an intensity of at least about 100 Hz.

In some aspects, the light-generating means can be externally activated by an external controller. The external controller can comprise a power generator which can be mounted to a transmitting coil. In some embodiments of the external controller, a battery can be connected to the power generator, for providing power thereto. A switch can be connected to the power generator, allowing an individual to manually activate or deactivate the power generator. In some embodiments, upon activation of the switch, the power generator can provide power to the light-generating means on the light source through electromagnetic coupling between the transmitting coil on the external controller and the external antenna of the implantable light source (such as a light cuff). The transmitting coil can establish an electromagnetic coupling with the external antenna of the implantable light source when in proximity thereof, for supplying power to the light-generating means and for transmitting one or more control signals to the implantable light source. In some embodiments, the electromagnetic coupling between the transmitting coil of the external controller and the external antenna of the implantable light source (such as a light cuff) can be radio-frequency magnetic inductance coupling. When radio-frequency magnetic inductance coupling is used, the operational frequency of the radio wave can be between about 1 and 20 MHz, inclusive, including any values in between these numbers (for example, about 1 MHz, about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, about 15 MHz, about 16 MHz, about 17 MHz, about 18 MHz, about 19 MHz, or about 20 MHz). However, other coupling techniques may be used, such as an optical receiver, infrared, or a biomedical telemetry system (See, e.g., Kiourti, "Biomedical Telemetry: Communication between Implanted Devices and the External World, Opticon 1826, (8): Spring, 2010).

Non-Human Animal Models of Behavior

The present disclosure provides non-human animal models of behavioral disorders, where a light-responsive protein as described above is expressed in a BNST neuron, a BNST subnucleus, or a neuronal output to or from a BNST neuron; and where exposure of the BNST neuron, BNST subnucleus, or neuronal output to or from a BNST neuron to light induces behavioral and/or physiological features of a behavioral disorder. Suitable non-human animals include rodents (e.g., rats; mice). In some cases, the non-human animal model is a rat. In some cases, the non-human animal model is a mouse. In some cases, the non-human animal is a non-human primate.

For example, an excitatory light-responsive protein (e.g., ChR2, and other excitatory light-responsive proteins, as described above) can be expressed in a BNST somata; and exposure of the BNST neuron to light of a wavelength to which the light-responsive protein responds results in increased anxiety. As another example, an excitatory light-responsive protein can be expressed in an ovBNST; and exposure of the BNST neuron to light of a wavelength to which the light-responsive protein responds results in increased anxiety and increased respiratory rate.

For example, in some embodiments, a subject non-human animal model comprises an excitatory light-responsive polypeptide comprising an amino acid sequence having at least about 80%, at least about 85%, at least about 90%, at least about 95%, at least about 98%, or 100%, amino acid sequence identity to one of SEQ ID NOs:5, 6, 7, 8, 9, 10, and 11, where the polypeptide is expressed in a BNST somata, and wherein, exposure of the BNST neuron to light of a wavelength to which the light-responsive protein responds results in increased anxiety. In some cases, the excitatory light-responsive polypeptide comprises both ER export and membrane trafficking signals. For example, in some cases, the excitatory light-responsive polypeptide comprises, from the N-terminus to the C-terminus, the amino acid sequence at least 95% identical to the sequence shown in SEQ ID NO:5, an ER export signal, and a membrane trafficking signal. In other cases, the excitatory light-responsive polypeptide comprises, from the N-terminus to the C-terminus, the amino acid sequence at least 95% identical to the sequence shown in SEQ ID NO:5, a membrane trafficking signal, and a ER export signal. In some cases, the membrane trafficking signal is derived from the amino acid sequence of the human inward rectifier potassium channel Kir2.1. In some cases, the membrane trafficking signal comprises the amino acid sequence KSRITSEGEYIPLDQIDINV (SEQ ID NO:16). In some cases, the ER export signal comprises the sequence FCYENEV (SEQ ID NO:26).

For example, in some embodiments, a subject non-human animal model comprises an excitatory light-responsive polypeptide comprising an amino acid sequence having at least about 80%, at least about 85%, at least about 90%, at least about 95%, at least about 98%, or 100%, amino acid sequence identity to one of SEQ ID NOs:5, 6, 7, 8, 9, 10, and 11, where the polypeptide is expressed in an ovBNST neuron, and wherein, exposure of the ovBNST neuron to light of a wavelength to which the light-responsive protein responds results in increased anxiety and increased respiratory rate. In some cases, the excitatory light-responsive polypeptide comprises both ER export and membrane trafficking signals. For example, in some cases, the excitatory light-responsive polypeptide comprises, from the N-terminus to the C-terminus, the amino acid sequence at least 95% identical to the sequence shown in SEQ ID NO:5, an ER export signal, and a membrane trafficking signal. In other cases, the excitatory light-responsive polypeptide comprises, from the N-terminus to the C-terminus, the amino acid sequence at least 95% identical to the sequence shown in SEQ ID NO:5, a membrane trafficking signal, and a ER export signal. In some cases, the membrane trafficking signal is derived from the amino acid sequence of the human inward rectifier potassium channel Kir2.1. In some cases, the membrane trafficking signal comprises the amino acid sequence KSRITSEGEYIPLDQIDINV (SEQ ID NO:16). In some cases, the ER export signal comprises the sequence FCYENEV (SEQ ID NO:26).

For example, in some embodiments, a subject non-human animal model comprises an inhibitory light-responsive polypeptide comprising an amino acid sequence having at least about 80%, at least about 85%, at least about 90%, at least about 95%, at least about 98%, or 100%, amino acid sequence identity to one of SEQ ID NOs:1, 2, 3, 4, 12, 13, 14, and 15, where the polypeptide is expressed in a BLA pyramidal neuron input to an adBNST neuron, and wherein, exposure of the BLA pyramidal neuron input to light of a wavelength to which the light-responsive protein responds results in increased anxiety and increased respiratory rate. In some cases, the inhibitory light-responsive polypeptide comprises both ER export and membrane trafficking signals. For example, in some cases, the inhibitory light-responsive polypeptide comprises, from the N-terminus to the C-terminus, the amino acid sequence at least 95% identical to the sequence shown in SEQ ID NO:1, an ER export signal, and a membrane trafficking signal. In other cases, the inhibitory light-responsive polypeptide comprises, from the N-terminus to the C-terminus, the amino acid sequence at least 95% identical to the sequence shown in SEQ ID NO:1, a membrane trafficking signal, and a ER export signal. In some cases, the membrane trafficking signal is derived from the amino acid sequence of the human inward rectifier potassium channel Kir2.1. In some cases, the membrane trafficking signal comprises the amino acid sequence KSRITSEGEYIPLDQIDINV (SEQ ID NO:16). In some cases, the ER export signal comprises the sequence FCYENEV (SEQ ID NO:26).

As another example, an inhibitory light-responsive protein (e.g., NpHR, and other inhibitory light-responsive proteins, as described above) can be expressed in a BLA pyramidal neuron input to an adBNST; and exposure of the BLA pyramidal neuron input to an adBNST to light of a wavelength to which the light-responsive protein responds results in increased anxiety and increased respiratory rate.

A nucleic acid (e.g., an expression vector) comprising a nucleotide sequence encoding a light-responsive protein can be introduced into a non-human animal (e.g., a rodent such as a rat or a mouse; or a non-human primate) by any convenient means. For example, a nucleic acid (e.g., an expression vector) comprising a nucleotide sequence encoding a light-responsive protein can be injected stereotactically into the BLA, BNST, LH, PB or VTA.

Suitable expression vectors include, but are not limited to, lentiviral, HSV, adenoviral, and adeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art. Suitable expression vectors are described above, and in the Examples.

A subject non-human animal model of a behavioral disorder is useful for screening for agents that ameliorate one or more behavioral and/or physiological features of a behavioral disorder.

Screening Methods

The present disclosure provides screening methods to identify agents that modulate one or more behavioral and/or physiological features of a behavioral disorder.

A subject screening method generally involves: a) administering a test agent to a non-human animal model of the present disclosure; and b) determining the effect of the test agent on a behavioral or physiological feature of a behavioral disorder exhibited by the non-human animal when the light-responsive opsin polypeptide is activated by light. A test agent that ameliorates a behavioral or physiological feature is considered a candidate agent for ameliorating a behavioral or physiological feature of a behavioral disorder.

For example, a test agent that ameliorates behavioral or physiological feature of a behavioral disorder, exhibited by a subject non-human animal model, by at least about 5%, at least about 10%, at least about 15%, at least about 20%, at least about 25%, or more than 25% (e.g., 25% to 50%; 50% to 75%; etc.) can be considered a candidate agent for ameliorating (treating) a behavioral or physiological feature of a behavioral disorder. Test agents identified using a subject method can be considered candidate agents for treating any of a variety of behavioral disorders and other adverse psychological and physiological states.

In some cases, a test agent is assessed for its effect on respiratory rate. In other cases, a test agent is assessed for its effect on anxiety.

A light-responsive protein expressed in a subject non-human animal model can be activated by an implantable light source, where suitable light sources are described above and in the Examples. Suitable wavelengths for activating an inhibitory or an excitatory opsin protein are described above.

Whether a test agent treats (e.g., ameliorates) a behavioral or physiological feature of a behavioral disorder exhibited by a subject non-human animal model can be determined using any appropriate method, including those described in the Examples. For example, elevated plus maze (EPM), the open field test (OFT), and the real-time place preference (RTPP) test can be used. Respiratory rate can be measured using any convenient method, including the method described in the Examples.

For example, in some embodiments, a subject screening method comprises: a) administering a test agent to a subject non-human animal model, where the non-human animal model comprises an excitatory light-responsive polypeptide comprising an amino acid sequence having at least about 80%, at least about 85%, at least about 90%, at least about 95%, at least about 98%, or 100%, amino acid sequence identity to one of SEQ ID NOs:5, 6, 7, 8, 9, 10, and 11, where the polypeptide is expressed in a BNST somata, and wherein, exposure of the BNST neuron to light of a wavelength to which the light-responsive protein responds results in increased anxiety. In some cases, the excitatory light-responsive polypeptide comprises both ER export and membrane trafficking signals; and b) determining the effect of a test agent on anxiety when the light-responsive protein is activated by light. In some cases, the excitatory light-responsive polypeptide comprises, from the N-terminus to the C-terminus, the amino acid sequence at least 95% identical to the sequence shown in SEQ ID NO:5, an ER export signal, and a membrane trafficking signal. In other cases, the excitatory light-responsive polypeptide comprises, from the N-terminus to the C-terminus, the amino acid sequence at least 95% identical to the sequence shown in SEQ ID NO:5, a membrane trafficking signal, and a ER export signal. In some cases, the membrane trafficking signal is derived from the amino acid sequence of the human inward rectifier potassium channel Kir2.1. In some cases, the membrane trafficking signal comprises the amino acid sequence KSRITSEGEYIPLDQIDINV (SEQ ID NO:16). In some cases, the ER export signal comprises the sequence FCYENEV (SEQ ID NO:26).

As another example, in some embodiments, a subject screening method comprises: a) administering a test agent to a subject non-human animal model, where the non-human animal model comprises an excitatory light-responsive polypeptide comprising an amino acid sequence having at least about 80%, at least about 85%, at least about 90%, at least about 95%, at least about 98%, or 100%, amino acid sequence identity to one of SEQ ID NOs:5, 6, 7, 8, 9, 10, and 11, where the polypeptide is expressed in an ovBNST neuron, and wherein, exposure of the ovBNST neuron to light of a wavelength to which the light-responsive protein responds results in increased anxiety and increased respiratory rate; and b) determining the effect of a test agent on anxiety and/or respiratory rate when the light-responsive protein is activated by light. In some cases, the excitatory light-responsive polypeptide comprises both ER export and membrane trafficking signals. For example, in some cases, the excitatory light-responsive polypeptide comprises, from the N-terminus to the C-terminus, the amino acid sequence at least 95% identical to the sequence shown in SEQ ID NO:5, an ER export signal, and a membrane trafficking signal. In other cases, the excitatory light-responsive polypeptide comprises, from the N-terminus to the C-terminus, the amino acid sequence at least 95% identical to the sequence shown in SEQ ID NO:5, a membrane trafficking signal, and a ER export signal. In some cases, the membrane trafficking signal is derived from the amino acid sequence of the human inward rectifier potassium channel Kir2.1. In some cases, the membrane trafficking signal comprises the amino acid sequence KSRITSEGEYIPLDQIDINV (SEQ ID NO:16). In some cases, the ER export signal comprises the sequence FCYENEV (SEQ ID NO:26).

As another example, in some embodiments, a subject screening method comprises: a) administering a test agent to a subject non-human animal model, where the non-human animal model comprises an inhibitory light-responsive polypeptide comprising an amino acid sequence having at least about 80%, at least about 85%, at least about 90%, at least about 95%, at least about 98%, or 100%, amino acid sequence identity to one of SEQ ID NOs:1, 2, 3, 4, 12, 13, 14, and 15, where the polypeptide is expressed in a BLA pyramidal neuron input to an adBNST neuron, and wherein, exposure of the BLA pyramidal neuron input to light of a wavelength to which the light-responsive protein responds results in increased anxiety and increased respiratory rate; and b) determining the effect of a test agent on anxiety and/or respiratory rate when the light-responsive protein is activated by light. In some cases, the inhibitory light-responsive polypeptide comprises both ER export and membrane trafficking signals. For example, in some cases, the inhibitory light-responsive polypeptide comprises, from the N-terminus to the C-terminus, the amino acid sequence at least 95% identical to the sequence shown in SEQ ID NO:1, an ER export signal, and a membrane trafficking signal. In other cases, the inhibitory light-responsive polypeptide comprises, from the N-terminus to the C-terminus, the amino acid sequence at least 95% identical to the sequence shown in SEQ ID NO:1, a membrane trafficking signal, and a ER export signal. In some cases, the membrane trafficking signal is derived from the amino acid sequence of the human inward rectifier potassium channel Kir2.1. In some cases, the membrane trafficking signal comprises the amino acid sequence KSRITSEGEYIPLDQIDINV (SEQ ID NO:16). In some cases, the ER export signal comprises the sequence FCYENEV (SEQ ID NO:26).

Symptoms that can be analyzed in a subject non-human animal model include, e.g., reduced escape-related behavior, anxiety, and stress. Tests for depression and/or anxiety and/or stress include the forced swim test (FST) (see, e.g., Porsolt et al. (1977) *Nature* 266:730; and Petit-Demouliere, et al. (2005) *Psychopharmacology* 177: 245); the tail suspension test (see, e.g., Cryan et al. (2005) *Neurosci. Behav. Rev.* 29:571; and Li et al. (2001) *Neuropharmacol.* 40:1028); conditioned place aversion (see, e.g., Bechtholt-Gompf et al. (2010) *Neuropsychopharmacol.* 35:2049); the novelty hypophagia test (Dulawa, et al. (2005) *Neurosci. Biobehav. Rev.* 29:771); the social defeat stress test (see, e.g., Blanchard et al. (2001) *Physiol Behav.* 73:261-271; and Kudryavtseva et al. (1991) *Pharmacol. Biochem. Behav.* 38: 315); the sucrose preference test (see, e.g., Kurre Nielsen, et al. (2000) *Behavioural Brain Research* 107:21-33); the open field test (see, e.g., Holmes (2001) *Neurosci. Biobehav. Rev.* 25:261-273); the elevated plus maze test (see, e.g., Holmes (2001) supra); and the like. Any such test can be used in a subject screening method.

As used herein, the term "determining" refers to both quantitative and qualitative determinations and as such, the term "determining" is used interchangeably herein with "assaying," "measuring," and the like.

The terms "candidate agent," "test agent," "agent", "substance" and "compound" are used interchangeably herein. Candidate agents encompass numerous chemical classes, typically synthetic, semi-synthetic, or naturally occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.) and can also be used. Alternatively, libraries of natural compounds in the form of bacterial, fungal, plant and animal extracts are available from Pan Labs (Bothell, Wash.) or are readily producible.

Candidate agents can be small organic or inorganic compounds having a molecular weight of more than 50 daltons and less than about 2,500 daltons. Candidate agents can comprise functional groups necessary for structural interaction with proteins, e.g., hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, and derivatives, structural analogs or combinations thereof.

Assays of the present disclosure include controls, where suitable controls include a subject non-human animal model that has been exposed to activating light, but has not been administered the test agent.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Materials and Methods

Methods Summary

Virus-mediated gene expression. AAV5 viruses were packaged by the University of North Carolina Vector Core (Chapel Hill, N.C., USA). Maps for the AAV constructs are available at http://www(dot)optogenetics(dot)org. 0.5 pl of viral stock was injected stereotactically into the BLA, BNST, LH, PB or VTA.

Anxiety Assays and Respiratory Rate Measurement.

Mice injected with viruses and implanted with guide cannulae or fiberoptics were subsequently tested in the elevated plus maze (EPM), the open field test (OFT), and the real-time place preference (RTPP) test. An EPM test session was 15-min long, consisting of 5-min light off-on-off epochs; the OFT was 20-min long, consisting of 5-min light off-on-off-on epochs. In the RTPP test, the subject could freely explore two chambers, and entry-to or exit-from one of the chambers turned optogenetic stimulation on or off, respectively. Behavioral data were automatically collected and analyzed by BIOBSERVE software. Respiratory rate was measured with a pulse oximeter from awake, behaving mice for 3 min. Yellow light was delivered as constant illumination, whereas blue light was delivered as a train of 10-Hz, 5-ms pulses.

In Vivo Physiology.

Custom-made microdrives containing 8 stereotrodes surrounding a fiberoptic were implanted in the BNST, allowing for light delivery and recording of BNST neurons in awake behaving animals. Further details of analysis and computation of EPM scores are provided below.

Ex Vivo Electrophysiology.

Acute slices were prepared for slice patch-clamp recordings. Whole-cell recordings were conducted from BNST neurons and blue light pulses at 10 Hz were delivered onto coronal sections via the microscope objective.

Statistics. All graphs and numerical values in the figures are presented as mean±s.e.m. Further details of statistical analyses are provided below.

Subjects

Figure 10:
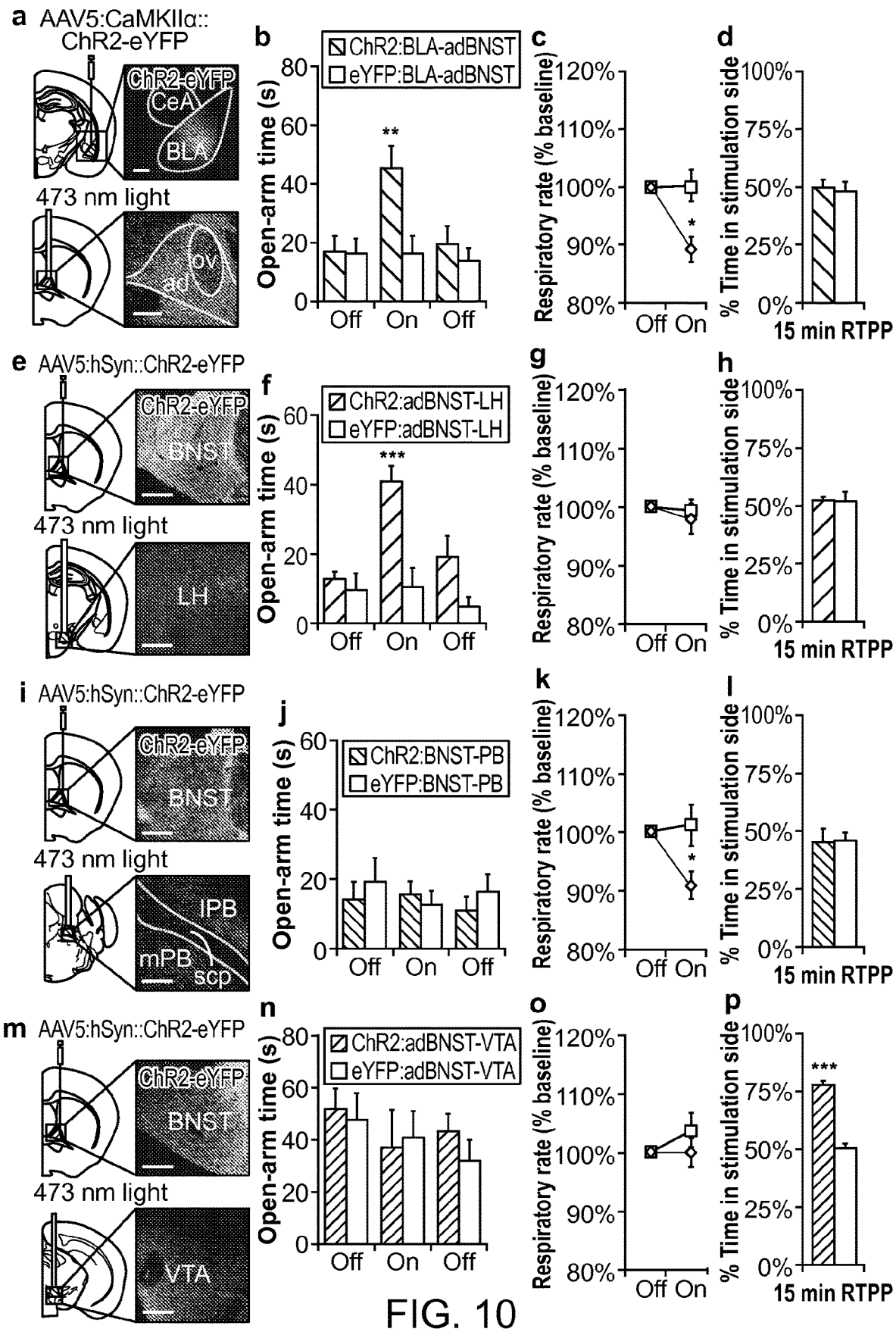
FIGS. 10A-P depict distinct adBNST outputs modulate different features related to anxiolyis.

Male C57BL/6 mice, aged 6-8 weeks at the start of experiments, were housed in a reverse 12-hr light/dark cycle. Food and water were given ad libitum. Dopamine receptor D1a (Drd1a)-Cre transgenic mice (founder line: EY266) were obtained from GENSAT. All mice used for behavioral experiments were single-housed to reduce baseline behavioral variability, except for eNpHR3.0:BLA-adBNST and ChR2:BNST somata mice, which were group-housed to decrease baseline anxiety levels'. In addition, a cohort of ChR2:BLA-adBNST mice (used to produce data presented in FIG. 10d and FIG. 12) was group housed to demonstrate that stimulation of the BLA-adBNST projection is anxiolytic in group-housed, low-anxiety-baseline animals. All experimental protocols were approved by the Stanford University Institutional Animal Care and Use Committee and were in accordance with the guidelines from the National Institute of Health.

Virus Production

The adeno-associated virus (AAV) vectors were serotyped with AAV5 coat proteins and packaged by the University of North Carolina Vector Core (Chapel Hill, N.C., USA). Viral titers were:

$4 \times 10^{12}$ particles/ml for AAV5:CaMKIIa::hChR2 (H134R)-eYFP $3 \times 10^{12}$ particles/ml for AAV5:CaMKIIa::eYFP $4 \times 10^{12}$ particles/ml for AAV5:CaMKIIa::eNpHR3.0-eYFP $4 \times 10^{12}$ particles/ml for AAV5:hSyn::hChR2(H134R)-eYFP $4 \times 10^{12}$ particles/ml for AAV5:hSyn::eYFP $4 \times 10^{12}$ particles/ml for AAV5:hSyn::eNpHR3.0-eYFP $2 \times 10^{12}$ particles/ml for AAV5:EF1a::DIO-eNpHR3.0-eYFP $2 \times 10^{12}$ particles/ml for AAV5:EF1a::DIO-ChR2(H134R)-eYFP The maps for these constructs are available at www(dot)optogenetics(dot)org. The herpes simplex virus (HSV) was derived by R.N. from HSV strain 17+ and was replication-incompetent. The functional titer of this HSV amplicon virus, which enables persistent expression in vivo, was $3 \times 10^8$ infectious units (i.u.)/ml. Rabies virus (RV) was produced as previously described[2]. Rabies virus glycoprotein (RVG) was replaced by eGFP or tdTomato to generate virus expressing eGFP (RV:eGFP) or tdTomato (RV:tdTomato).

Stereotactic Viral Injection and Guide Cannula/Fiberoptic Cannula Implantation

All surgical procedures were performed aseptically. Mice were anaesthetized with 1.5-3.0% isoflurane, and were placed in a stereotaxic apparatus (Kopf Instruments, Tujunga, Calif., USA) while resting on a heating pad. For mice used in drug injection experiments, a small craniotomy was performed, and a guide cannula (22 gauge C313G/SPC GUIDE 38172; PlasticsOne, Roanoke, Va., USA) was unilaterally placed on top of the BNST (AP +0.2 mm, ML1.0 mm, DV-3.9 mm). All coordinates are relative to bregma in mm[3]. Adhesive cement (C&B metabond; Parkell, Edgewood, N.Y., USA) was first applied and dental cement (Stoelting, Wood Dale, Ill., USA) was added to secure the cannula to the skull. The incision was closed using tissue adhesive (Vetbond; Fisher, Pittsburgh, Pa., USA). A dummy cap (C313DC/1/SPC DUMMY 0.014/0.36MM; PlasticsOne) was inserted to maintain the cannula guide free of obstructions.

For all mice used in behavioral optogenetic manipulations, 0.5 μl of virus was injected per site. ChR2 mice received unilateral viral infusion and fiberoptic cannula implantation (0.22 NA, 200 μm diameter; Doric Lenses, Quebec, Canada), whereas all eNpHR3.0 mice were bilaterally injected and implanted since unilateral loss-of-function may be compensated by the other hemisphere. All unilateral manipulations including drug injection, viral injection and cannula implantation were counter-balanced across hemispheres. For optogenetic manipulations of BNST somata, after a small craniotomy, AAV5:hSyn::eNpHR3.0-eYFP or AAV5:hSyn::ChR2-eYFP was injected in the center of the dorsal BNST (AP +0.2 mm, ML±1.0 mm, DV -4.3 mm) using a 10 pl syringe and a 33 gauge beveled metal needle (Nanofil, WPI, Sarasota, Fla., USA), with the bevel facing anteriorly. hSyn (human synapsin) is a pan-neuronal promoter[4] which enables expression of transgenes in all neurons in the BNST. Injections were via syringe pump (UMP3; WPI) and rate was set to 0.1 μl/min by the controller (Micro4; WPI). After injection the needle was slowly lifted 100 μm, and then left in place for 5 additional minutes before slow withdrawal to avoid upward flow of the liquid along the needle. Control groups were injected with AAV5:hSyn::eYFP. Two fiberoptic cannulae were then placed on top of the bilateral BNST (AP +0.2 mm, ML 1.0 mm, DV -4.0 mm) and secured to the skull as described above. Mice recovered from anesthesia in a warm cage. Behavioral and electrophysiological experiments were conducted within a window of 4-6 weeks (for all cell body manipulations) or 8-12 weeks (for all terminal manipulations) after injection, to allow for opsin expression.

For optogenetic stimulations of BNST terminals in the LH, PB or VTA, all procedures were the same, except that AAV5:hSyn::ChR2-eYFP was delivered into the BNST and fiberoptic cannulae were placed above the LH (AP -1.0 mm, ML 1.3 mm, DV -5.0 mm), PB (AP -5.2 mm, ML 1.5 mm, DV -3.2 mm) or VTA (AP -3.4 mm, ML 0.3 mm, DV -3.9 mm). For optogenetic manipulations of BLA terminals in the BNST, AAV:CaMKIIa::hChR2(H134R)-eYFP, AAV:CaMKIIa::eNpHR3.0-eYFP or (for control) AAV:CaMKIIa::eYFP was delivered into the BLA (AP -1.6 mm, ML±3.1 mm, DV -4.9 mm) and fiberoptic cannulae were placed on top of the BNST. As CaMKIIa is a marker of glutamatergic pyramidal neurons in the BLA[5], the use of the CaMKIIa promoter enables transgene expression favoring BLA pyramidal neurons. To stimulate BLA fibers in the anterior commissure, AAV:CaMKIIa::hChR2(H134R)-eYFP was injected to the BLA and the fiberoptic cannula was implanted right above the anterior commissure (AP +0.14 mm, ML 1.5 mm, DV -4.4 mm). For optogenetic inhibition of the ovBNST, Drd1aCre mice were injected with AAV:EF1a::D10-eNpHR3.0-eYFP on top of the BNST and fiberoptic cannulae were placed on top of the BNST.

For probing the regions projecting to the ovBNST, 0.3 μl of RV:eGFP was injected in the ovBNST (AP +0.2 mm, ML 1.0 mm, DV -4.1 mm). For dual rabies virus injections, 0.5 μl of RV:eGFP, 0.5 μl of RV:tdTomato or 0.5 μl of the mixture of two viruses were injected in the LH (AP -1.5 mm, ML 1.0 mm, DV -5.6 mm), PB (AP -5.2 mm, ML 1.0 mm, DV -3.8 mm) or VTA (AP -3.5 mm, ML 0.35 mm, DV -4.5 mm).

Drug Delivery

For the glutamate receptor antagonist infusion in the BNST, a glutamate antagonist solution consisting of 10 mM 2,3-dihydroxy-6-nitro-7-sulfamoyl-benzo[f]quinoxaline-2,3-dione (NBQX; Tocris, Ellisville Mo., USA) and 50 mM 2-amino-5-phosphonopentanoic acid (D-APV; Tocris) was dissolved in saline (0.9% NaCl). Thirty minutes before the anxiety assays, 0.3 µl of the glutamate antagonist solution was infused in the BNST via an internal infusion needle (28 gauge C313I/SPC INTERNAL38799; PlasticsOne), inserted into the same guide cannula used to introduce fiberoptic cannulae for light delivery. The internal needle was connected to a 10-µl Hamilton syringe (Nanofil; WPI). The flow rate (0.1 µl/min) was regulated by a syringe pump (Harvard Apparatus, Holliston, Mass., USA). The internal infusion needle protruded beyond the cannula guide by about 500 µm, to penetrate potential blood-clotting at the tip of the cannula guide and reach the center of the dorsal BNST. The infusion needle was removed 2 min following the termination of the injection to avoid spillage from the guide cannula.

Light Delivery

For all optogenetic inhibition experiments using eNpHR3.0, 5 mW (159 mW/mm$^2$ at the tip of the fiberoptic) of yellow light was generated by a 593.5 nm DPSS laser (MGLF593.5; OEM Laser Systems, East Lansing, Mich., USA), and bilaterally delivered to mice through two fiberoptic patch cords (0.22 NA, 200 µm diameter; Doric Lenses) that were attached to the implanted fiberoptic cannulae, using a connecting plastic sleeve. For all optogenetic stimulation experiments using ChR2, 3-5 mW of blue light (95-159 mW/mm$^2$ at the tip of the fiberoptic) was generated by 473 nm DPSS laser (MBL-111473; OEM Laser Systems) and unilaterally delivered. Constant yellow laser was used for yellow light delivery to all eNpHR3.0 mice, while blue laser output was controlled using a pulse generator (Master-8; AMPI, Jerusalem, Israel) to deliver 5-ms light pulse trains at 10 Hz (for all ChR2 mice except for ChR2:adBNST-VTA mice) or at 20 Hz (for ChR2:adBNST-VTA mice).

Behavioral Assays

All mice were handled for three days before behavioral assays for 5 min per day to reduce stress introduced by contact with experimenter. 1-5 minutes were allowed for recovery in the home cage from handling for connecting the fiberoptic cannula and patchcord, before the session was initiated. The elevated plus maze was made of plastic and consisted of two gray open arms (30×5 cm) and two grey enclosed arms (30×5×30 cm) extending from a central platform (5×5×5 cm) at 90 degrees in the form of a plus. Arms of the same type faced each other. The maze was placed 30 cm above the floor. Mice were individually placed in the center, with the head facing a closed arm. The elevated plus maze test consisted of a 15-min session divided into three 5-min epochs: the pre-stimulation light-off epoch, the light-on epoch and the post-stimulation light-off epoch, in order (off-on-off epochs). The open-field chamber (50×50 cm) was made of plastic and was divided into a central field (center, 25×25 cm) and an outer field (periphery). Individual mice were placed in the periphery of the field at the start of the test. The open field test consisted of a 20 min session in which there were four 5 min epochs (off-on-off-on epochs). The epochs alternated between no light and light stimulation periods, beginning with the baseline light-off epoch. For all analyses and plots where only light-off and -on conditions are displayed, both off epochs were pooled and both on epochs were pooled. Real-time place preference test was performed in a custom-made black plastic arena (50×50×25 cm) consisting of two indistinguishable chambers for 15 min. One chamber was paired with light stimulation. The choice of paired chamber was counterbalanced across mice Animals were placed in the unstimulated chamber at the start of the session and received light stimulation initiated upon every entry into the paired chamber. Light-dark box test was performed in a custom-made grey plastic arena (50×25 cm) consisting of light and dark compartments for 15 min. The mouse was placed in the dark compartment at the beginning of the experiment. For all behavior assays, video tracking software (Viewer$^2$; BIOBSERVE, St. Augustin, Germany) was used to automatically track location and velocity.

Respiratory Rate and Heart Rate Measurement

Respiratory rate and heart rate were measured with a pulse oximeter (MouseOx Plus; Starr Life Sciences, Allison Park, Pa., USA) connected to a computer equipped with MouseOx Plus software. For recordings from awake mice, a collar sensor was used. Mice were shaved around the neck and acclimated to the collar sensor (Starr Life Sciences, Allison Park, Pa., USA) overnight. Additionally, mice were habituated to handling by the experimenter for three days prior to the measurements. All recordings were made on top of the cage, unless otherwise stated. Mice were given 5 min for acclimation on the cage and were recorded for 3 min as the baseline measurement, and light was delivered for the next 3 min. Respiratory rate as a moving average of 10 measurements was obtained every 1.7 seconds. Heart rate was recorded as a moving average over 5 heart beats. Recording was often discontinued due to signal loss or motion artifacts; therefore, all parameters were carefully monitored in real time and recordings were discarded when physiologically unrealistic values were observed due to insufficient sampling (e.g. respiratory rate of <100 brpm or heart rate of <600 bpm). To ensure the quality of the recording, at least two recordings per mouse were made and averaged, and recordings that failed to monitor heart and respiration rates for more than 30% of time were discarded. All respiratory rate data were obtained with the protocol described above, except for data shown in FIGS. 9 and 15. The procedure used in these figures is detailed below.

Figure 29A:
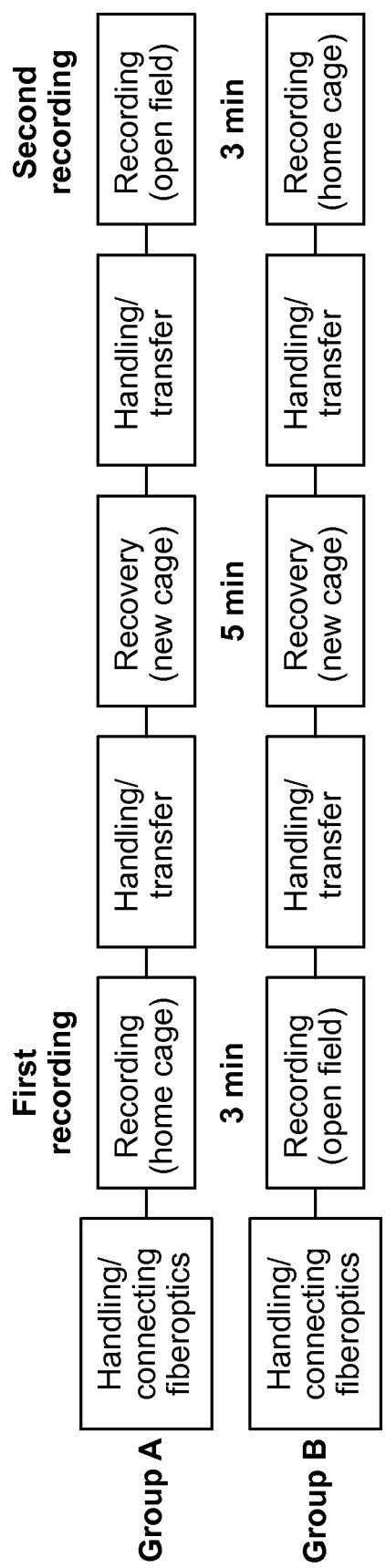
FIGS. 29A-B provide the recording schemes for the data presented in FIG. 8 and FIG. 15.

To compare respiratory rates between the home cage and the open field, respiration rates were measured in these two environments in the same mice. Mice were recorded in the home cage or the open field for 3 min, given 5 min for recovery in a new clean cage and then recorded in the other environment for 3 min. Recordings were started immediately after placing the mice in each environment. To counterbalance the order of recording, in half of the mice, the recording was performed in the home cage first and then in the open field (Group A, in the figure below). For the other half, the order of recording was switched (Group B). Between two recordings, each mouse was allowed to recover in a new, clean cage. The data shown in FIG. 8 was recorded according to the scheme provided in FIG. 29A.

Figure 29B:
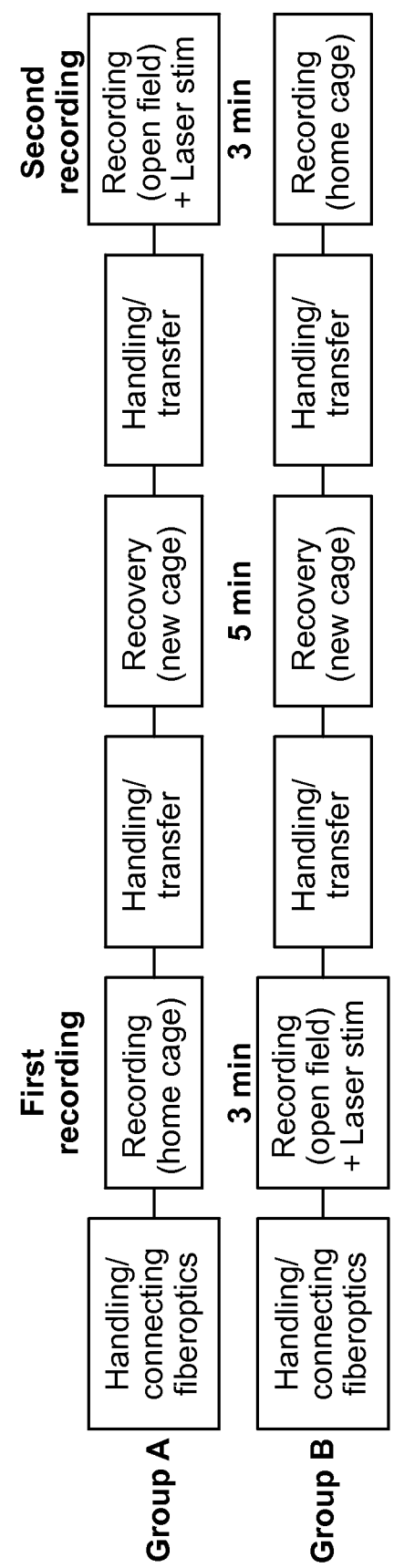

Respiratory rates from the open field were divided by respiratory rates from the home cage and the resulting value was compared between the ChR2 and eYFP groups. Thus, respiratory rates in the home cage were used as the baseline for all mice, both in group A and B. Handling and transporting mice across environments was done both before recording in the home cage and before recording in the open field. Therefore, handling itself could not underlie differences in respiratory rate between environments (moreover, all animals were extensively handled three days prior to the recordings to habituate animals both to handling and to moving with the collar sensor clipped on). To further demonstrate that handling and transferring mice across environments cannot be responsible for the observed effect, we compared respiratory rates of Group A in the open field with Group B in the home cage. Even though both groups of mice were equally handled/transported prior to the recording, mice placed in the open field exhibited statistically significant higher respiratory rates than the ones in the home cage (233.1±12.8 brpm, n=3 for the open field; 170.3±7.4 brpm, n=4 for the home cage; p<0.05), showing that increased respiratory rate is caused by the open field and cannot be attributed to prior transportation and handling. For the experiment shown in FIG. 15, light was delivered when mice were placed in the open field. The protocol used to obtain the data shown on FIG. 15 was identical to that used in FIG. 8, with the difference that blue light was delivered during exploration of the open field, as shown in the scheme provided in FIG. 29B.

Ex Vivo Electrophysiological Recording

For slice physiology in combination with optogenetics, 3-4 week old male wild-type mice were injected with AAV-CaMKIIa::ChR2-eYFP into the BLA, or male Drd1a-Cre mice were injected with AAV-EF1a::DIO-ChR2 (H134R)-eYFP into the ovBNST. After a month, acute 300 μm coronal slices were obtained by transcardially perfusing ice-cold sucrose cutting solution (in mM; 11 D-glucose, 234 sucrose, 2.5 KCl, 1.25 $NaH_2PO_4$, 10 $MgSO_4$, 0.5 $CaCl_2$, 26 $NaHCO_3$) and slicing in the same solution using a vibratome (VT1000S; Leica, Buffalo Grove, Ill., USA). Slices were recovered in oxygenated artificial cerebrospinal fluid (aCSF; in mM, 123 NaCl, 26 $NaHCO_3$, 3 KCl, 1.25 $NaH_2PO_4$, 1 $MgCl_2$, 2 $CaCl_2$, and 11 glucose) at 32° C. for one hour. All electrophysiological recordings were made under the constant perfusion of aCSF bubbled with 95% $O_2$/5% $CO_2$ and heated to 32° C. Neurons were visualized with an upright microscope (DMLFSA; Leica) equipped with both DIC optics and a filter set for visualizing eYFP, using a 40× water-immersion objective and a charge-coupled device (CCD) camera (RetigaExi FAST; QImaging, Surrey, Canada). Slices containing the BLA were used to verify the expression of ChR2 in the BLA, and only the slices from the mice with ChR2 expression restricted to the BLA were used. Whole-cell recordings were made from adBNST neurons (see further discussion below), using patch electrodes (3-6 MΩ) filled with either potassium-based internal solution (in mM; 10 HEPES, 4 Mg-ATP, 0.5 $MgCl_2$, 0.4 $Na_3$-GTP, 10 NaCl, 0.5 EGTA and 140 potassium gluconate) or cesium-based internal solution (in mM; 10 HEPES, 4 Mg-ATP, 0.3 $Na_3$-GTP, 2 NaCl, 8 CsCl, 4 EGTA, 1 QX314 and 130 cesium gluconate). Most voltage-clamp experiments and all current-clamp experiments were conducted with potassium-based internal solution, and some voltage-clamp experiments were done with cesium-based internal solution to improve spatial clamp. Series resistances were typically 10-20 MΩ.

For the blue light delivery, light was emitted from a 300 W broad-wavelength xenon lamp source (DG-4, Sutter Instruments, Novato, Calif., USA), band-pass filtered at 470±20 nm (Semrock; Rochester, N.Y., USA), passed through additional neutral density filters (ThorLabs; Newton, N.J., USA) and coupled to the fluorescence port of the microscope. For all experiments, 5-15 mW/mm² of light was delivered to slices through 40×, 0.8 NA objectives. Pulsed input signals were generated from pClamp (Molecular Devices; Sunnyvale, Calif., USA) and were delivered to the DG-4 via BNC.

Voltage-clamp recordings were made at both −70 mV to isolate EPSCs, and at 0 mV to isolate IPSCs. Light-evoked EPSCs and IPSCs were abolished by bath application of glutamate receptor antagonists (10 μM NBQX and 50 μM APV; n=4; FIG. 19e). IPSCs were confirmed via bath application of 100 μM picrotoxin (10 μM; n=4; FIG. 19f), respectively. We also performed current-clamp recordings when the cell was resting at approximately −60 mV. Currents were filtered at 2 kHz, digitized at 50 kHz, and recorded to disk using pClamp10 software (Molecular Devices).

Figure 4:
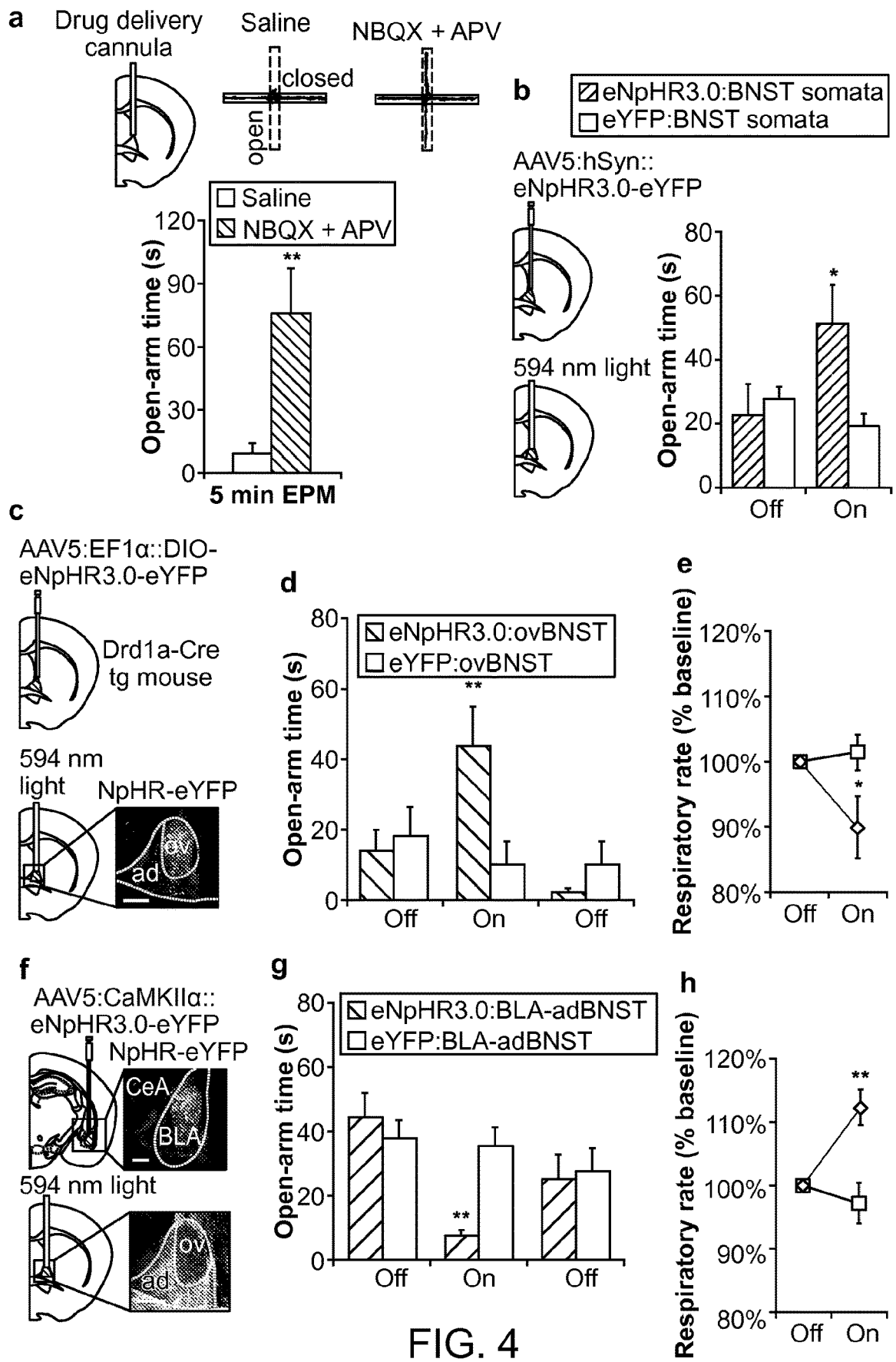
FIGS. 4A-H depict functional heterogeneity within the dorsal BNST.

For the experiments stimulating BLA axon fibers, patch-clamp recordings were from the adBNST. Although there is no clear anatomical boundary between the ovBNST and the adBNST seen with DIC optics, we conducted recordings in the region where eYFP-expressing fibers were present as the ovBNST does not receive projections from the BLA (FIGS. 4f and 10a). In agreement with this, putative ovBNST neurons in the dorsal region of the BNST did not exhibit any light-evoked responses. For the experiments recording from adBNST neurons projecting to the LH, HSV:EF1a::GFP was injected into the LH (AP −1.5 mm, ML 1.2 mm, DV −6.0 mm) 3-4 days before slice physiology experiments to label adBNST neurons projecting to the LH. Patch-clamp recordings were performed in GFP-expressing BNST neurons after visually identifying GFP expression in individual cells.

Microdrive Construction and Implantation

Custom microdrives containing eight stereotrodes surrounding a fiberoptic cannula (0.22 NA, 200 μm diameter; Doric Lenses) were constructed based on interface boards (EIB-16; Neuralynx; Bozeman, Mont., USA) attached to a Teflon platform (modified from Adhikari et al., 2011[7]). Stereotrodes were constructed of 25 mM Formvar-coated tungsten microwires (M165260; California Fine Wire; Grover Beach, Calif., USA) and were secured to a cannula attached to the interface board. A fiberoptic cannula was attached to the interface board and glued to the microwires in such a way that microwires protruded beyond the tip of the optic fiber by about 0.5 mm. The whole platform was fastened to Teflon cuffs via three fine machine screws (SHCX-080-6; Small Parts; Miramar, Fla., USA), allowing the platform to advance by turning the screws into the cuffs. For implantation, additional screws were implanted on the posterior and anterior portions of the skull to serve as ground and physical support, respectively. After carefully placing the microdrive in the BNST, the Teflon cuffs were cemented to the skull (Grip Dental Cement; Dentsply, York, Pa., USA), and the ground screw was connected to the interface board.

In Vivo Single-Unit Recordings

Animals were permitted to recover for at least one week, and then food-restricted to 85% body weight. During food-restriction, animals were familiarized to the recording setup and handling by being tethered to the head stage in their home cages. The EPM was chosen for the in vivo recording over the OFT, because it has well-defined boundaries between the more anxiogenic (open arms) and the safe areas (closed arms). Furthermore, typically mice explore the entire EPM, while most of the area of the center of the OFT is not visited. This increases the accuracy in the estimation of firing rates in each arm of the EPM. As an independent assay of anxiety, the light-dark box test was performed in a custom-made grey plastic arena (50×25 cm) consisting of light and dark compartments for 15 min. Mice were placed in the dark compartment at the beginning of the experiment.

Figure 2:
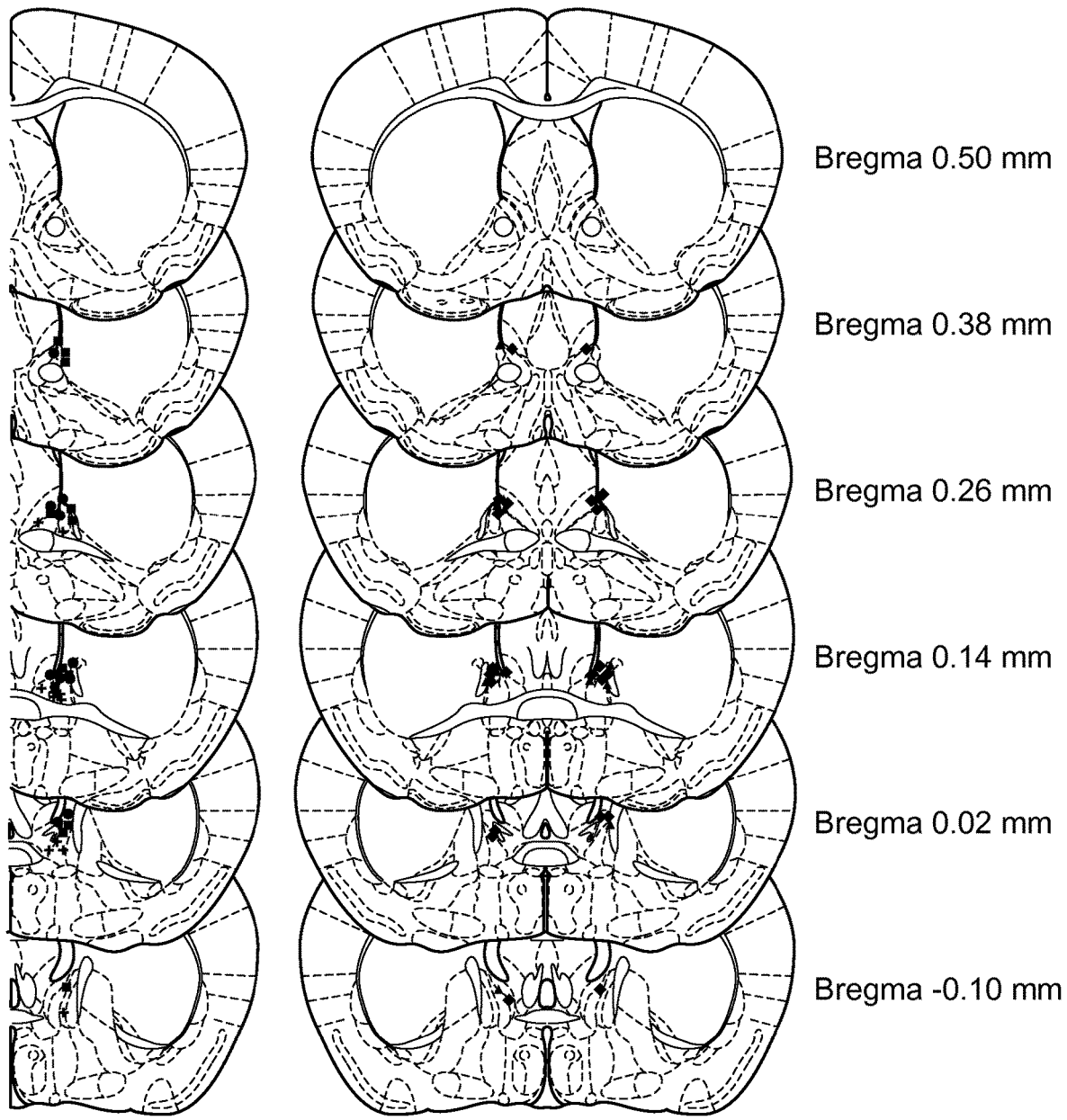
FIG. 2 depicts placement of fiberoptics and stereotrode arrays targeting the adBNST.

Stereotrodes were advanced until at least four well-isolated single units could be recorded in the BNST. Activation or inhibition of the ChR2- or eNpHR3.0-expressing BLA fibers respectively increased or decreased activity in the recorded area. This indicates that recording was in the adBNST, as light delivery would not be expected to change activity in the ovBNST which lacks BLA fibers. Furthermore, electrical lesions made to mark the tip of the electrodes were only observed in the adBNST (FIG. 2). Recordings were obtained via a unitary gain head-stage preamplifier (HS-16; Neuralynx; Bozeman, Mont., USA) attached to a fine wire cable. Spikes exceeding 40 μV were band-pass filtered (600-6,000 Hz) and recorded at 32 kHz. Spike data were acquired with Cheetah data acquisition software (Neuralynx). Animal position was obtained by overhead video tracking (30 Hz) of two light-emitting diodes affixed to the headstage.

Single-Unit Spike Sorting and Analysis

Data were imported into Matlab for analysis using custom-written software. Clustering of spikes was performed offline manually with SpikeSort 3D (Neuralynx). To classify the in vivo response of adBNST single units to stimulation of ChR2-expressing BLA terminals, we recorded responses across 400 presentations of a 5-ms blue light pulse. Firing rates were analyzed in a 100 ms epoch centered at the laser pulse onset (−50 to 50 ms, with the pulse occurring at 0 ms). If z-scored firing rates were significantly different between baseline (−50 to 0 ms) and after the pulse (0 to 35 ms), units were classified as "responsive" to the pulse. Among "responsive units", if the z-scored mean firing rate was higher after the pulse, units were classified as "significantly excited". Otherwise, they were classified as inhibited. Excited units were further divided into units exhibiting "only transient responses" (firing rates from 0 to 10 ms significantly higher than baseline and rates from 10 to 35 ms not significantly different from baseline) or units exhibiting "transient and sustained responses" (rates from 0 to 35 ms after onset are significantly higher than baseline rates). Persistent multiunit activity was defined as firing rates (measured as z-scores) significantly higher in the seconds 30 to 40 compared to baseline (seconds −30 to 0). Wilcoxon rank-sum test was used to compare responses to the laser pulse.

EPM Score Calculation

Only data from mice that explored all arms of the maze were used. EPM scores were computed to quantify the extent to which single units can consistently differentiate the open arm vs. closed arm structure of the maze. EPM scores were calculated through the following formula:

Score=$(A-B)/(A+B)$, where $A=0.25\times(|FL-FU|+|FL-FD|+|FR-FU|+|FR-FD|)$ and $B=0.5\times(|FL-FR|+|FU-FD|)$.

FL, FR, Fu, and Fp are the % difference from mean firing rate in left, right, up and down arms, respectively. "A" is the mean difference in normalized firing rate between arms of different types, while "B" is the mean difference for arms of the same type. Although we used rates in each location as "% change from mean firing rate", one could also use "fold-increase from mean firing rate", as this choice does not affect the final EPM score. Cells with firing patterns related to the task have similar firing rates in arms of the same type (resulting in a small B) and large differences in rates between arms of different types (resulting in a large value for A). Importantly, a positive score would be assigned both to a cell that fires selectively in both open arms, as well as to a cell that fires selectively in both closed arms. The maximum score of 1.0 indicates no difference in firing rates across arms of the same type (B=0). On the other hand, a score of zero would be assigned to the cell that has the same firing rate in all arms of the maze. Lastly, negative scores indicate that firing rates are more similar across arms of different types than across arms of the same type (e.g. the cell that has high firing rates selectively in only one closed arm and one open arm).

To calculate EPM scores during the light OFF epoch, all spikes from a given single unit during the 10 OFF epochs were pooled together. Each epoch has 60 seconds (see FIG. 22e). The total number of spikes in the OFF epoch divided by the total number of seconds in the OFF epoch (60 sec/epochs×10 epochs=600 sec) yielded the mean firing rate in the OFF epoch. Firing rates in each arm were calculated as % change from this mean OFF firing rate. These firing rates were used to calculate the OFF EPM scores, as shown in the formula above.

Analogously, to calculate EPM scores during the light ON epoch, all the spikes from a given single unit that occurred in the ON epoch were pooled together to calculate the mean ON firing rate. Note that spiking activity in the OFF epoch has no influence on the calculation of mean firing rate or firing rate in a specific arm in the ON epoch. The schemes shown in Tables 1 and 2 illustrates step-by-step how to calculate EPM scores during the light ON and OFF epochs from unprocessed data.

TABLE 1

Light OFF epoch

| Location | #spikes | #seconds | Rate (Hz) | Rate (% change from mean) |
|---|---|---|---|---|
| Up arm (Open arm 1) | 40 | 70 | 40/70 = 0.57 | $F_U = 100 \times ((0.57-0.687/0.87)$ $F_U = -34$ |
| Down arm (Open arm 2) | 30 | 76 | 0.39 | $F_D = -55$ |
| Left arm (closed arm 1) | 209 | 191 | 1.09 | $F_L = +25$ |
| Right arm (closed arm 2) | 215 | 217 | 0.99 | $F_R = +13$ |
| Center | 30 | 46 | 0.65 | $F_C = -25$ |

Total # of spikes = 40 + 30 + 209 + 215 + 30
Total # spikes = 524
Total # of seconds = 70 + 76 + 191 + 217 + 46
Total # of seconds = 600
Mean rate = 524/600 = 0.87 Hz
EPM score = $(A - B)/(A + B)$, where $A = 0.25 \times (|F_L - F_U| + |F_L - F_D| + |F_R - F_U| + |F_R - F_D|)$ and $B = 0.5 \times (|F_L - F_R| + |F_U - F_D|)$.
A = 64 and B = 16
EPM score (Light OFF) = 0.60

TABLE 2

Light ON epoch

| Location | #spikes | #seconds | Rate (Hz) | Rate (% change from mean) |
|---|---|---|---|---|
| Up arm (Open arm 1) | 20 | 50 | 20/50 = 0.4 | $F_U = 11 \times ((0.4-0.62)/0.62)$ $F_U = -35$ |
| Down arm (Open arm 2) | 36 | 80 | 0.45 | $F_D = -27$ |
| Left arm (closed arm 1) | 157 | 219 | 0.72 | $F_L = +15$ |

TABLE 2-continued

Light ON epoch

| Location | #spikes | #seconds | Rate (Hz) | Rate (% change from mean) |
|---|---|---|---|---|
| Right arm (closed arm 2) | 112 | 197 | 0.56 | $F_R = -8$ |
| Center | 48 | 54 | 0.88 | $F_C = 42$ |

Total # of spikes = 373
Total # of seconds = 600
Mean rate = 373/600 = 0.62
EPM score = (A − B)/(A + B), where A = 0.25 × (|$F_L - F_U$| + |$F_L - F_D$| + |$F_R - F_U$| + |$F_R - F_D$|) and B = 0.5 × (|$F_L - F_R$| + |$F_U - F_D$|).
A = 35 and B = 16
EPM score (Light ON) = 0.37

Calculation of EPM Scores with Simulated Data

To calculate if the population of experimentally observed EPM scores was significantly different than expected by chance, a simulated distribution of scores was generated. For each unit with n spikes, 500 simulated scores were generated by calculating the EPM score of n randomly chosen timestamps 500 times. This generated a distribution with 500×38 simulated EPM scores. Among these 19000 simulated EPM scores, 12730 (67%) values were negative. The population of positive simulated scores (33%) was almost perfectly evenly divided among close and open-arm preferring cells (3129 and 3141 values, respectively). The significance of the population of experimentally observed EPM scores of all cells was calculated by comparison to the simulated distribution of scores using the Wilcoxon rank-sum test.

Histological Verification and Confocal Microscopy

Figure 3:
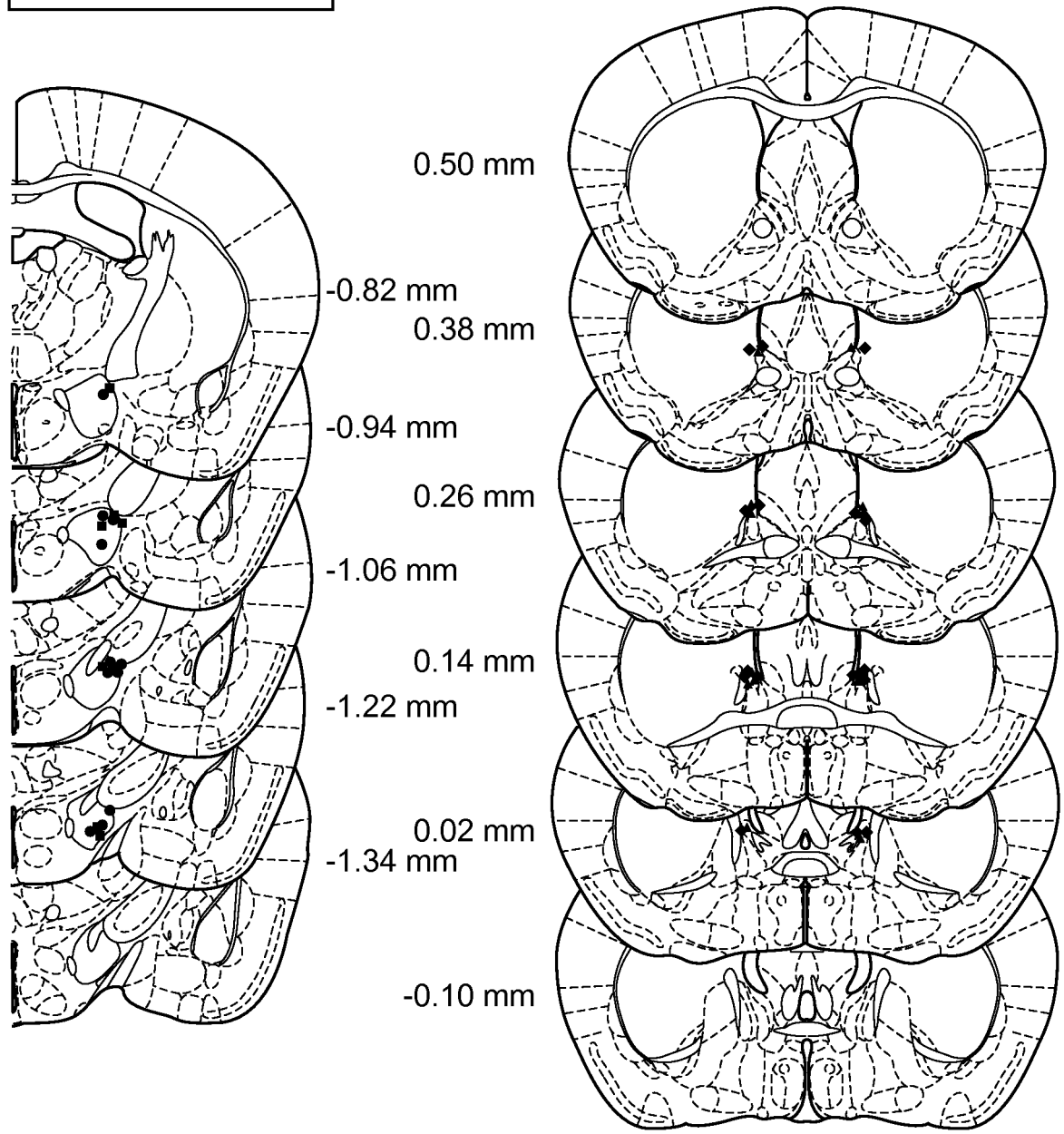
FIG. 3 depicts placement of fiberoptics targeting the ovBNST and the LH.

Mice were deeply anesthetized and transcardially perfused with ice-cold 4% paraformaldehyde (PFA) in PBS (pH 7.4). Brains were fixed overnight in 4% PFA solution and then equilibrated in 30% sucrose in PBS. After the brains were sunken in the sucrose solution, 40 μm-thick coronal slices were cut on a freezing microtome. Placement of the guide cannula, fiberoptics and stereotrode arrays were easily visible after slicing (FIGS. 1-3). Slices were stored in a cryoprotectant solution (a 5:6:9 mixture of glycerol, ethylene glycol and PBS) at 4° C. until further processed. Free-floating sections were washed in PBS, incubated for 25 min in 1:50,000 DAPI solution, washed again in PBS and mounted on microscope slides with PVD-DABCO. Confocal images were obtained on a Leica TCS SP5 scanning laser microscope using a 20×/0.70 NA or 40×/1.25 NA oil immersion objective. Images were analyzed using Leica Microsystems LAS AF software.

Calcium Imaging and Analysis

Coronal brain slices including the BNST were prepared from young mice (n=4 slices, P8-P10, 300 μm thick) and stained with Oregon Green Bapta-1 AM (OGB). Briefly, slices were cut on a vibratome in ice cold aCSF (in mM: 110 choline chloride, 25 NaHCO$_3$, 10 D-glucose, 7 MgCl$_2$ 3.1 sodium pyruvate, 2.5 KCl, 1.25 NaH$_2$PO$_4$, 0.5 CaCl$_2$), and were immediately transferred to recovery aCSF solution (in mM: 125 NaCl, 26 NaHCO$_3$, 10 D-glucose, 3 KCl, 2.5 MgCl$_2$, 1.6 CaCl$_2$, 1.25 NaH$_2$PO$_4$) at room temperature for one hour. Then, the slices were moved to an incubation chamber at 32° C. containing 2.5 ml recovery ACSF. 10 μl of OGB solution (50 μg OGB dissolved in 9 μl DMSO and 1 μl 20% pluronic acid in DMSO) was directly applied to the slices. After 20-25 min incubation in OGB solution, the slices were moved to experimental aCSF (in mM: 125 NaCl, 26 NaHCO$_3$, 10 D-glucose, 3 KCl, 1.5 MgCl$_2$, 1.6 CaCl$_2$, 1.25 NaH$_2$PO$_4$) at room temperature. After one hour, the imaging session began. Images were acquired using an epifluorescence microscope and a CCD camera (50 ms integration time, ~400 frames per trial at ~4 Hz). On a stimulation trial, a 0.2 ms current pulse was applied to a bipolar electrode positioned in the adBNST slice, and within the field of view of the microscope. For a set of stimulation conditions, the amplitude of the current pulse was varied between trials in either increasing or decreasing order in 10 μA steps between 10 and 50 μA. Then, 100 μM APV was applied to the perfusion bath, and the stimulation experiment was repeated. Then, 10 μM NBQX was applied to the bath (while maintaining the concentration of APV) and the stimulation was repeated again. For analysis of OGB fluorescence movies regions of interest (ROI) were drawn around each cell and around the neuropil using a semi-automated procedure. Pixels within each ROI were averaged for each frame, and a time series was generated for each cell. To correct for photobleaching of the fluorophore a bi-exponential was fit to each cell's baseline time series (before stimulation), assuming decay to the cell's minimum fluorescence value, and the fitted curve was subtracted from the cell's time series. A scaled time series of the neuropil was subtracted from each cell's time series to remove global events (the scaling was determined by the least squares difference between the neuropil's and each cell's time series). The change in fluorescence over baseline was computed for each cell for each trial ($\Delta F/F=(F_1-F)/F$, where Fi is the instantaneous fluorescence and F is the mean fluorescence during the baseline). A z-score was computed for each time series based on the standard deviation and mean of the baseline (~40 to 0 s relative to stimulation). Statistically significant activity in a neuron was defined as any modulation that occurred at least 5 seconds after electrical stimulation (because the neuropil responses decayed back to the baseline for about 5 seconds) and that exceeded z-score of 3.43 (p<0.05; Bonferroni correction).

Statistics

All statistical analysis was performed using GraphPad Prism (GraphPad Software; La Jolla, Calif., USA). For EPM and OFT data, two-way repeated measures ANOVA was used, followed by Bonferroni corrected post-hoc tests. P values in the main text indicate the p values for the interaction between the opsin treatment and the epochs, and asterisks (*) in the figures indicate the p values for the post-hoc test at the given epoch. For two-sample comparisons of a single variable (such as % change of respiratory rate of experimental groups and controls or onset latencies of EPSCs and IPSCs), the non-parametric Wilcoxon rank-sum test was used. All tests were two-tailed and had an alpha level of 0.05. Spearman's correlations were used instead of Pearson's correlation because Spearman's correlation is non-parametric, less sensitive to outliers and capable of detecting any monotonic relationship between two variables. Standard errors of means (s.e.m.) were plotted in graphs to show accuracy of estimation of the mean of the population.

YFP

The amino acid sequence of YFP in constructs was:

(SEQ ID NO: 28)
VSKGEELFTGVVPILVELDGDVNGHKFSVSGEGEGDATYGKLTLKFICTT

GKLPVPWPTLVTTFGYGLQCFARYPDHMKQHDFFKSAMPEGYVQERTIFF

KDDGNYKTRAEVKFEGDTLVNRIELKGIDFKEDGNILGHKLEYNYNSHNV

-continued

YIMADKQKNGIKVNFKIRHNIEDGSVQLADHYQQNTPIGDPVLLPDNHY

LSYQSALSKDPNEKRDHMVLLEFVTAAGITLGMDELYK

Results

Figure 5:
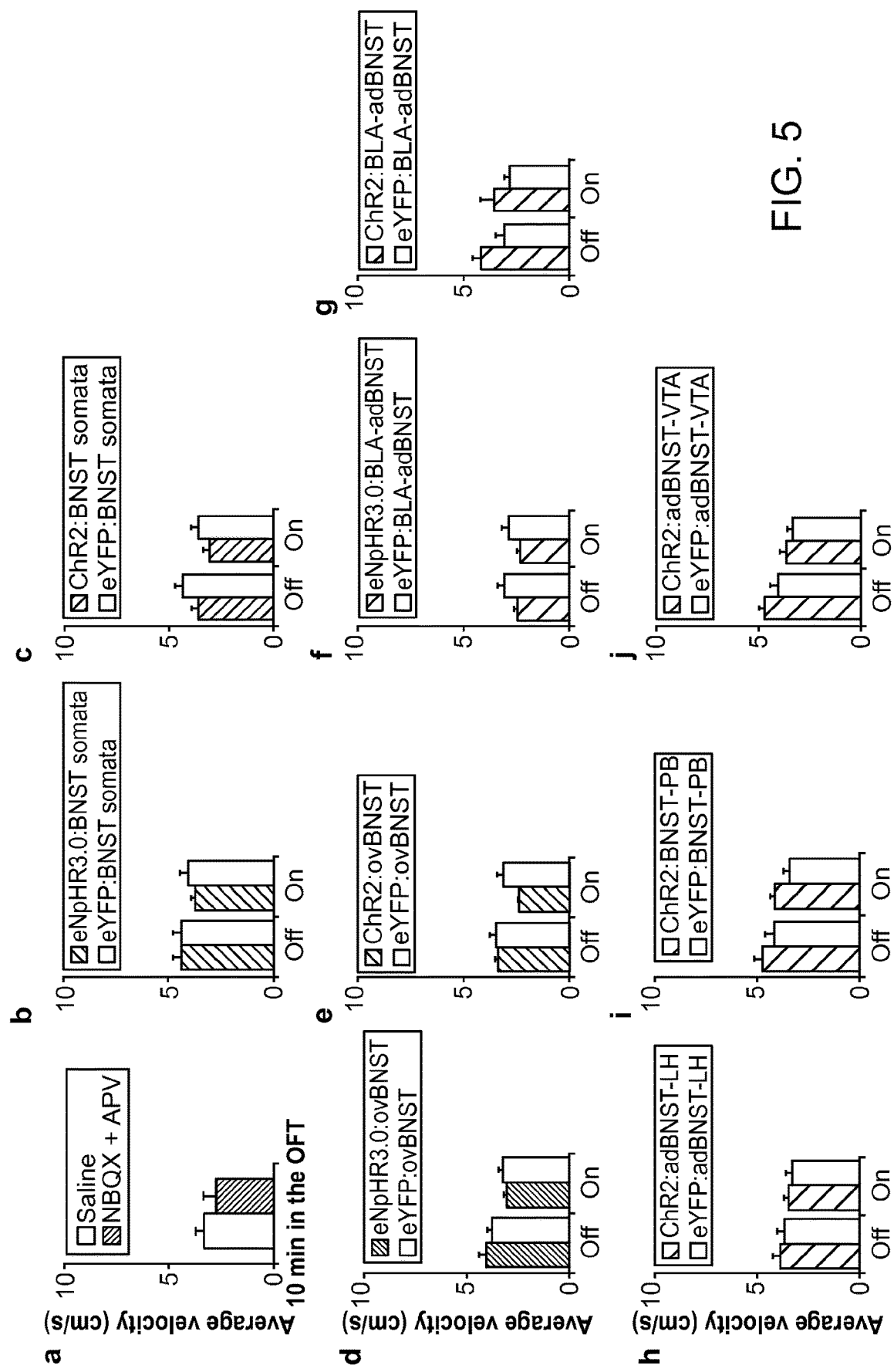
FIGS. 5A-J depict the effect of the various manipulations on locomotor activity.

Evidence from anatomical, behavioral and neuroimaging studies has implicated the BNST in pathological and adaptive anxiety; for example, lesions of the dorsal BNST, henceforth referred to as BNST, have been reported to decrease anxiety-like behavior. To further test this finding, we infused glutamate receptor antagonists into the BNST before the elevated-plus maze (EPM) test (FIG. 4a; histology in FIGS. 1-3). This intervention increased open-arm exploration ($p<0.01$, see statistical analysis; FIG. 4a) without altering locomotion (FIG. 5; such increased exploration of open spaces, to which mice exhibit innate aversion, is thought to represent reduced anxiety-like behavior). We next optogenetically inhibited the BNST using the inhibitory halorhodopsin eNpHR3.0 and delivery of yellow light to the BNST (eNpHR3.0:BNST somata; FIG. 4b); increased exploration of open spaces in the EPM and OFT was observed (FIG. 4b; FIGS. 6a and 6b), indicating anxiolysis. Conversely, stimulation of BNST somata with the excitatory channelrhodopsin ChR2 increased behavioral measures of anxiety in both assays (ChR2:BNST somata; FIG. 7). To test if this manipulation modulated physiological manifestations of anxiety, we stimulated BNST somata while monitoring respiratory rate; hyperventilation is linked to increased anxiety in humans and rodents (FIG. 8), and the BNST is known to project to respiratory centers Indeed, increased respiratory rate was observed (FIG. 7d). Together these results suggest that activity in the BNST drives an anxiety-like state, consistent with most previous studies.

FIG. 1. (Left) Unilateral placement of fiberoptic tips for ChR2:BNST somata mice and eYFP controls are indicated (cyan and gray, respectively). Guide cannula tip locations are indicated in red. All unilateral surgeries were counter-balanced for hemisphere. (Right) Bilateral placements of the fiberoptic tips for eNpHR3.0:BNST somata mice and controls are indicated (orange and black, respectively). Numbers indicate antero-posterior coordinates from bregma.

FIG. 2. (Left) Unilateral placements of fiberoptic tips for ChR2:BLA-adBNST mice and eYFP controls are indicated (cyan and gray, respectively). Tips of stereotrode arrays for in vivo recording are indicated in red. All unilateral surgeries were counter-balanced for hemisphere. (Right) Bilateral placements of the fiberoptic tips for eNpHR3.0:BLA-adBNST mice and controls are indicated (yellow and black, respectively). Numbers indicate antero-posterior coordinates from bregma.

FIG. 3. (Left) Unilateral placements of the tip of the fiberoptics for ChR2:adBNST-LH mice and eYFP controls are indicated (blue and gray, respectively). All unilateral surgeries were counter-balanced for hemisphere. (Right) Bilateral placements of fiberoptic tips for eNpHR3.0:ovBNST mice and controls are indicated (yellow and black symbols, respectively). Numbers indicate antero-posterior coordinates from bregma.

FIGS. 4a-h. Functional heterogeneity within the dorsal BNST. (a) Cannula for drug infusion; NBQX+D-APV increased open-arm time in EPM (n=5 for each). (b) eNpHR3.0:BNST somata mice were bilaterally implanted with fiberoptics above BNST. Light increased open-arm time in EPM (n=8 eNpHR3.0, n=7 eYFP). (c) eNpHR3.0:ovBNST mice received bilateral light. ovBNST-restricted expression was obtained with Cre-dependent eNpHR3.0-AAV in D1R-Cre mice. (d) Light delivery to ovBNST of eNpHR3.0:ovBNST mice increased open-arm time in EPM (n=7 eNpHR3.0, n=8 eYFP) and (e) decreased respiratory rate (n=7 eNpHR3.0, n=8 eYFP). (f) eNpHR3.0:BLA-adBNST mice expressing eNpHR3.0 in BLA received bilateral illumination of BLA fibers in adBNST. (g) Light in eNpHR3.0:BLA-adBNST mice reduced open-arm time (n=11 eNpHR3.0, n=15 eYFP) and (h) increased respiratory rate (n=8 eNpHR3.0, n=8 eYFP). Scale: 200 pm. Meant-s.e.m. shown; *=$p<0.05$; **=$p<0.01$.

Statistics. FIG. 4a. n=5 for each group. $p<0.01$. Wilcoxon rank-sum test. FIG. 4b. n=8 for eNpHR3.0:BNST somata group, n=8 for eYFP:BNST somata group. Two-way repeated-measures ANOVA detected significant interaction of group x light-epoch: $F_{2,28}=10.74$, $p<0.001$. Two groups showed significant difference at light-on epoch: $p<0.05$, post-hoc Bonferroni t-test. FIG. 4d. n=7 for eNpHR3.0:ovBNST group, n=8 for eYFP:ovBNST group. Two-way repeated-measures ANOVA detected significant interaction of group x light-epoch: $F_{2,26}=14.66$, $p<0.0001$. Two groups showed significant difference at light-on epoch: $p<0.01$, post-hoc Bonferroni t-test. FIG. 4e. n=7 for eNpHR3.0:ovBNST group, n=8 for eYFP:ovBNST group. $p<0.05$. Wilcoxon rank-sum test. FIG. 4g. n=11 for eNpHR3.0:BLA-adBNST group, n=15 for eYFP:BLA-adBNST group. Two-way repeated-measures ANOVA detected significant interaction of group x light epoch: $F_{2,48}=5.58$, $p<0.01$. Two groups showed significant difference at light-on epoch: $p<0.01$, post-hoc Bonferroni t-test. FIG. 4h. n=8 for eNpHR3.0:BLA-adBNST group, n=8 for eYFP:BLA-adBNST group. $p<0.01$. Wilcoxon rank-sum test.

FIGS. 5a-j. Locomotor activity was not altered by any of the manipulations performed. (a) Locally infusing NBQX and APV into the BNST (n=5 for exp, n=5 for controls; $p>0.05$), (b) inhibiting BNST somata (n=10 for exp; n=11 for controls; $p>0.05$), (c) stimulating BNST somata (n=6 for exp; n=6 for controls; $p>0.05$), (d) inhibiting the ovBNST (n=8 for exp; n=8 for controls; $p>0.05$), (e) stimulating ovBNST (n=7 for exp; n=7 for controls; $p>0.05$), (f) inhibiting BLA fibers in the adBNST (n=11 for exp; n=11 for controls; $p>0.05$), (g) stimulating BLA fibers in the adBNST (n=8 for exp; n=8 for controls; $p>0.05$), (h) stimulating adBNST fibers in the LH (n=11 for exp; n=8 for controls; $p>0.05$), (i) stimulating BNST fibers in the PB (n=8 for exp; n=7 for controls; $p>0.05$) or a) stimulating adBNST fibers in the VTA (n=8 for exp; n=7 for controls; $p>0.05$) had no detectable effect on mean locomotion speed. Values are mean±s.e.m.

FIGS. 6a-f. Functional heterogeneity in the BNST in anxiety paradigms. Yellow light in eNpHR3.0:BNST somata mice increased center time in the OFT (a) and open-arm entry probability in the EPM (b). Yellow light in eNpHR3.0:ovBNST mice increased center time in the OFT (c) and open-arm entry probability in the EPM (d). Yellow light in eNpHR3.0:BLA-adBNST mice reduced center time in the OFT (e) and open-arm entry probability in the EPM (f). Values are mean±s.e.nn.*,  and * indicate $p<0.05$, 0.01 and 0.001, respectively. Data in this figure represent additional behavioral results from the same cohorts shown in FIG. 4.

Figure 6:
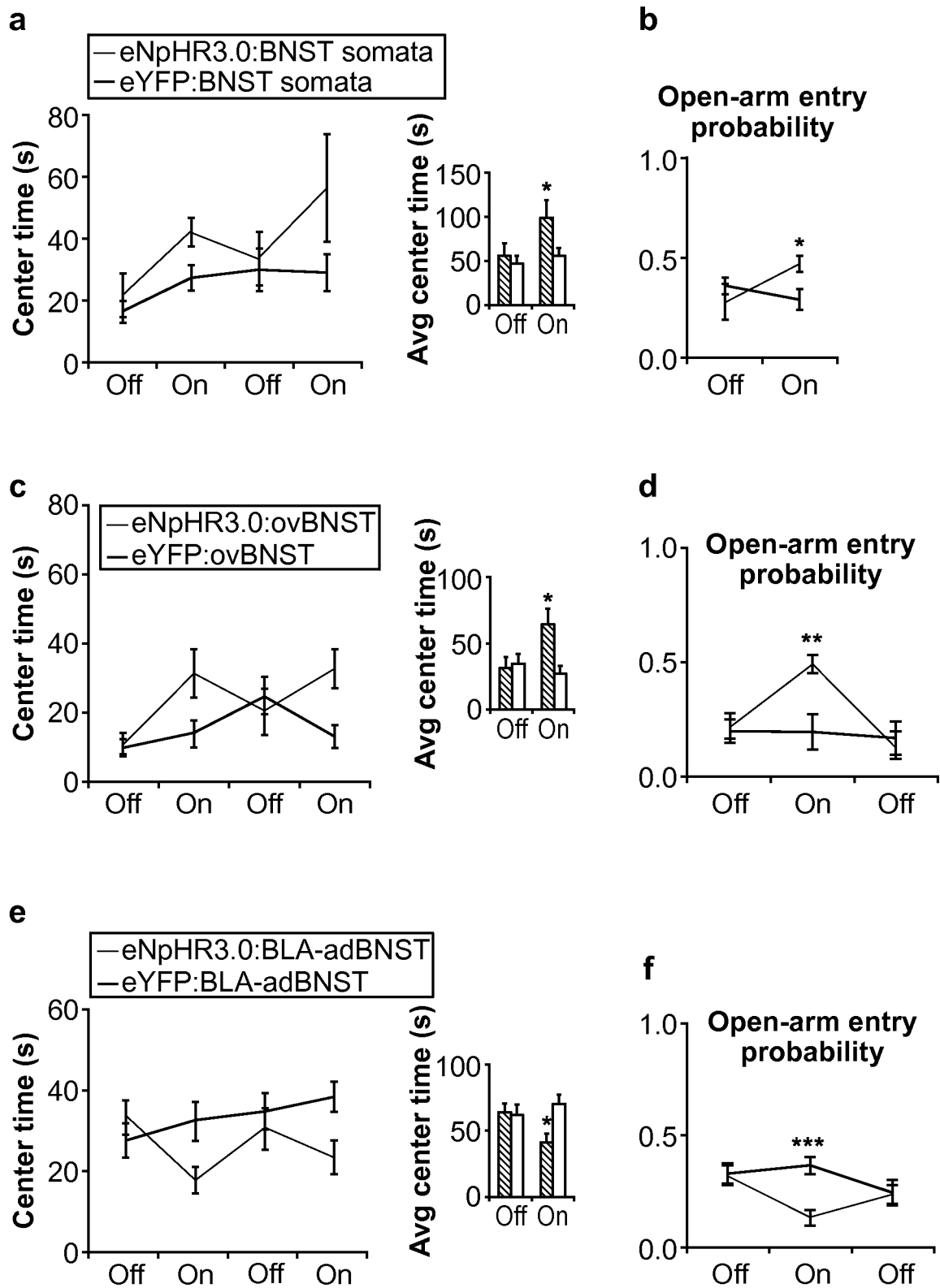
FIGS. 6A-F depict functional heterogeneity in the BNST in anxiety paradigms.

FIG. 6 Statistics. FIG. 6a. n=10 for eNpHR3.0:BNST somata group, n=11 for eYFP:BNST somata group. Two-way repeated-measures ANOVA did not detect significant interaction of group x light epoch. (Inset) Two-way repeated-measures ANOVA detected significant interaction of group x light epoch: $F_{1,13}=8.34$, $p<0.05$. Two groups showed a significant difference in the light-on epoch:

p<0.05, post-hoc Bonferroni t-test. FIG. 6b. n=10 for eNpHR3.0:BNST somata group, n=11 for eYFP:BNST somata group. Two-way repeated-measures ANOVA detected significant interaction of group x light epoch: F2,26=4.70, p<0.05. Two groups showed a significant difference in the light-on epoch: p<0.05, post-hoc Bonferroni t-test. FIG. 6c. n=7 for eNpHR3.0:ovBNST group, n=8 for eYFP:ovBNST group. Two-way repeated-measures ANOVA detected significant interaction of group x light epoch: F3,42=7.93, p<0.001. (Inset) Two-way repeated-measures ANOVA detected significant interaction of group× light epoch: F1,14=31.03, p<0.05. Two groups showed a significant difference in the light-on epoch: p<0.05, post-hoc Bonferroni t-test. FIG. 6d. n=7 for eNpHR3.0:ovBNST group, n=8 for eYFP:ovBNST group. Two-way repeated-measures ANOVA detected significant interaction of group x light epoch: F2,26=6.67, p<0.01. Two groups showed a significant difference in the light-on epoch: p<0.01, post-hoc Bonferroni t-test. FIG. 6e. n=13 for eNpHR3.0:BLA-adBNST group, n=15 for eYFP:BLA-adBNST group. Two-way repeated-measures ANOVA detected significant interaction of group x light epoch: F3,78=4.35, p<0.01. (Inset) Two-way repeated-measures ANOVA detected significant interaction of group x light epoch: F1,26=12.56, p<0.01. Two groups showed a significant difference in the light-on epoch: p<0.05, post-hoc Bonferroni t-test. FIG. 6f. n=13 for eNpHR3.0:BLA-adBNST group, n=15 for eYFP:BLA-adBNST group. Two-way repeated measures ANOVA detected significant interaction of group×light epoch: F2,48=6.24, p<0.01. Two groups showed a significant difference in the light-on epoch: p<0.001, post-hoc Bonferroni t-test.

FIGS. 7a-f. Optogenetic stimulation of BNST somata increases anxiety-related behavior. (a) 6-8 week old mice received a unilateral injection of 0.5 μl AAV5:hSyn::ChR2-eYFP (ChR2:BNST somata; n=6) or AAV5:hSyn::eYFP (eYFP:BNST somata; n=6) in the BNST and were implanted with fiberoptics directly above the BNST. Behavioral assays were performed 4 weeks after injection. Confocal image shows expression of ChR2-eYFP in BNST cell bodies (40× objective, 3× optical zoom, single plane). (b) Mice were run on the elevated plus maze for a 15-min session, consisting of 5-min light OFF/ON/OFF epochs. Blue light stimulation delivery during the ON epoch (5 ms pulse width, 10 Hz) in the ChR2:BNST somata group decreased open-arm time and open-arm entry probability (inset) relative to eYFP controls (F2,18=5.04, p<0.05; inset: F2,18=3.94, p<0.05). (c) A week later, mice were run on the open field for a 20-min session, consisting of 5-min light OFF/ON/OFF/ON epochs. Blue light stimulation decreased center time in the OFT during light on epochs compared to eYFP controls (left, F3,30=3.89, p<0.05; right, F1,10=16.02, p<0.01). (d) A week later, respiratory rate was measured from the same mice for 6 min, and light stimulation was given for the last 3 minutes. Light stimulation increased respiratory rate (p<0.05, Wilcoxon signed-rank test). (e-f) For comparison with (a), high-resolution images of BLA fibers expressing ChR2-eYFP in the adBNST (e) and adBNST fibers expressing ChR2-eYFP in the LH (f) are shown. For statistical analysis, two-way repeated measures ANOVA was used unless otherwise indicated. Values are mean±s.e.m. * and ** indicate p<0.05 and <0.01, respectively.

Figure 8:
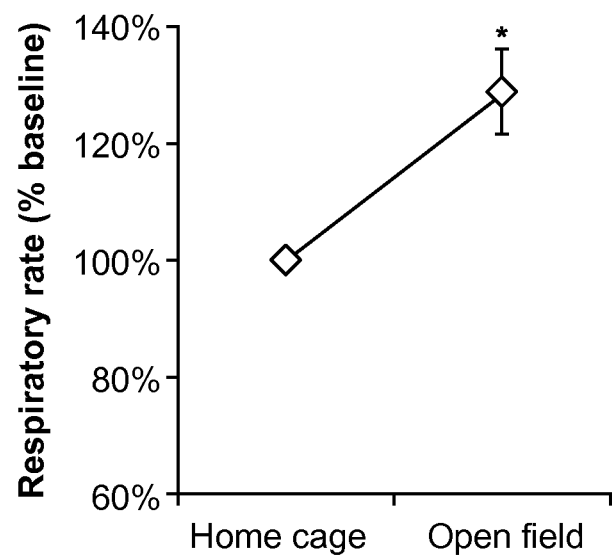
FIG. 8 depicts respiratory rate increases in an anxiogenic environment.

FIG. 8. Respiratory rate increases in an anxiogenic environment. 12-16 week old naïve mice (n=7) were handled for 3 days and acclimated to the collar clip used for the respiratory rate measurement. Respiratory rate was first recorded in the home cage or the open field for 3 minutes (min). Mice were given 5 min of resting in a new clean cage and then recorded in the other environment for 3 min. The order of recordings was counterbalanced across animals. Note that respiratory rate was significantly increased by placing the animals into an open field apparatus, an anxiogenic environment, compared to the values measured in the home cage (p<0.05, Wilcoxon signed-rank test0>*, p<0.05.

Figure 9:
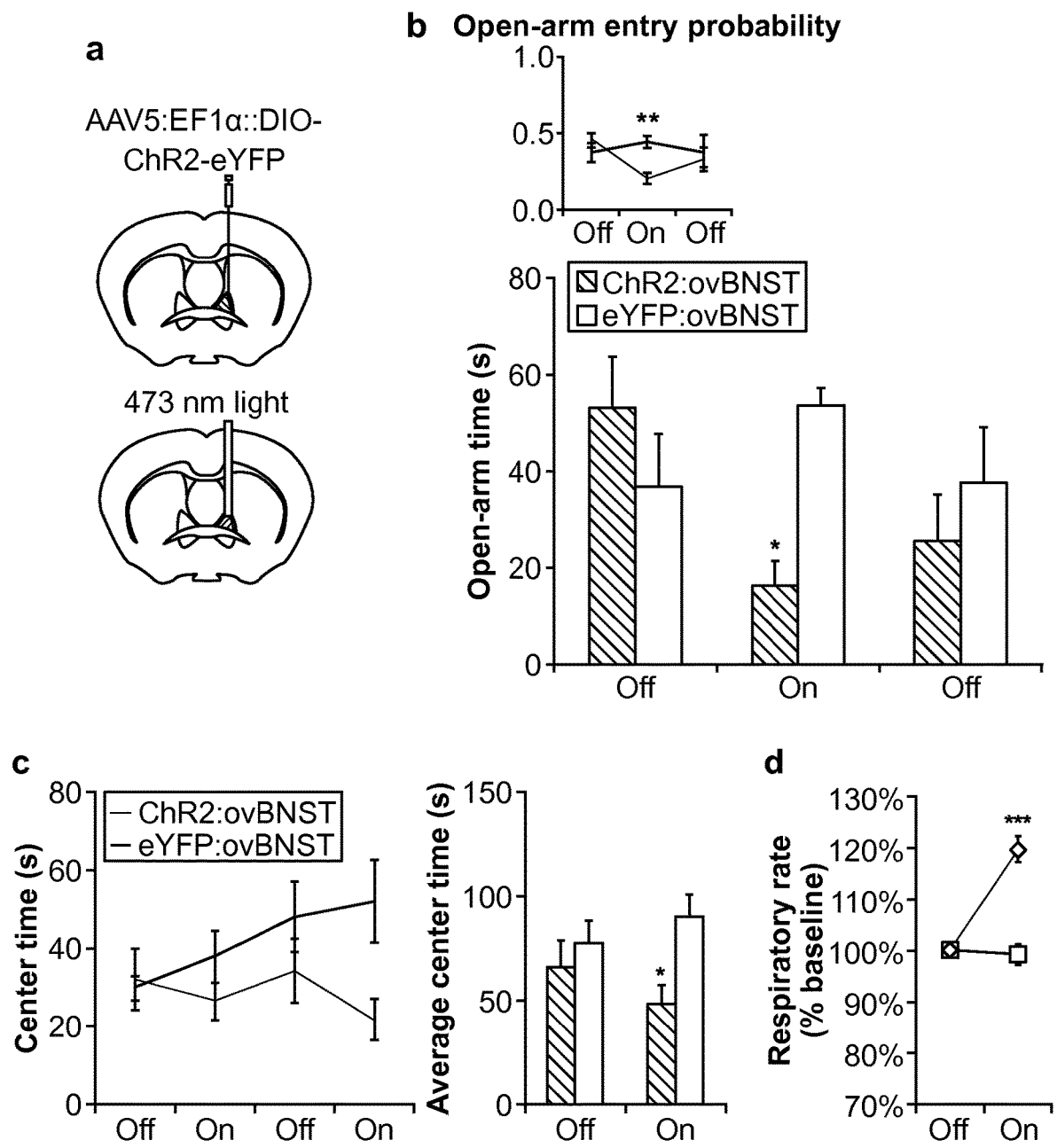
FIGS. 9A-D depict the effect of optogenetic stimulation of the ovBNST on anxiety-related behavior.

However, these results may not provide a complete picture of the BNST, which contains multiple subregions. The oval nucleus of the BNST (ovBNST) was targeted, by introducing a Cre-dependent eNpHR3.0 virus into the BNST of dopamine receptor 1a::Cre (Drd1 a::Cre) mice that show restricted Cre expression in the ovBNST (eNpHR3.0: ovBNST; FIG. 4c). Yellow light delivery in eNpHR3.0: ovBNST mice decreased avoidance of EPM open arms (p<0.0001; FIG. 4d) and the OFT center (p<0.001; FIG. 6c). The same manipulation also decreased respiratory rate (p<0.05; FIG. 4e). Conversely, stimulating the ovBNST with ChR2 increased both behavioral and physiological measures of anxiety (ChR2:ovBNST; FIG. 9). These results suggested an anxiogenic role for the ovBNST, and were consistent with the results obtained by modulating the entire BNST (FIGS. 4a-c).

We next investigated the function of basolateral amygdala (BLA) inputs to the BNST, since the BLA is a region implicated in anxiety that projects to the BNST. Mice expressing eNpHR3.0– eYFP in BLA pyramidal neurons displayed eYFP+ fibers projecting to the region of the BNST surrounding the ovBNST, which will be referred to as anterodorsal BNST, or adBNST (eNpHR3.0:BLA-adBNST; FIG. 4f)'. Surprisingly, inhibiting the BLA-adBNST projection increased avoidance of EPM open arms (p<0.01; FIG. 4g) and the OFT center (p<0.01; FIG. 6e), and also increased respiratory rate (p<0.01; FIG. 4h). Conversely, stimulating BLA inputs with ChR2 (ChR2:BLA-adBNST; FIG. 10a) decreased both behavioral anxiety measures (FIG. 10b, FIGS. 11a, 11b, and 12) and respiratory rate (p<0.05; FIG. 10c). Since the BLA projection is thought to be excitatory, as confirmed below, these data suggest that adBNST recruitment is anxiolytic, in contrast to the anxiogenic nature of ovBNST activity. Importantly, these effects were not attributable to excitation of BLA fibers in the anterior commissure (FIG. 13). As an additional test, considering that a clinically relevant feature of anxiolysis can be positive subjective valence, we asked if stimulating BLA-adBNST projections could elicit positive conditioning valence (using the real-time place preference task; RTPP, see Methods), but we did not observe elicited place preference (FIG. 10d).

Having found that adBNST activity decreases avoidance of open spaces and respiratory rate, we next investigated which adBNST outputs might mediate these distinct effects. The adBNST projection to lateral hypothalamus (LH) was a candidate for mediating decreases in behavioral expression of anxiety, as the LH receives projections from the adBNST, but not from the ovBNST (FIG. 14a), and is required for normal EPM behavior. In agreement with this hypothesis, we found that adBNST neurons projecting to the LH receive BLA input (FIGS. 14b-d), and that stimulating the adBNST-LH projection decreased avoidance of open spaces in both the EPM (p<0.01; FIG. 10f) and OFT (p<0.05; FIG. 11c). However, no effects were seen on respiratory rate (FIG. 10g) or RTPP (FIG. 10h), suggesting that the adBNST-LH pathway selectively modulates behavioral, but not physiological or appetitive, features of anxiolysis.

We hypothesized that the adBNST output to the parabrachial nucleus (PB) could mediate the decrease in respiratory rate seen in ChR2:BLA-adBNST mice (FIG. 10c), as the PB modulates respiration[2,17,26]. Indeed, in ChR2:BNST-PB mice (FIG. 10*i*), blue light decreased respiratory rate (p<0.05; FIG. 10*k*). Furthermore, stimulating the adBNST-PB projection attenuated respiratory rate increases in an anxiogenic environment (FIG. 15), but did not change behavior in the EPM or in the RTPP (FIGS. 10*j* and 10*l*). While both the adBNST and the ovBNST project to the PB, the decreased respiratory rate in ChR2:BNST-PB mice was likely driven by adBNST-PB fibers, as ovBNST activity increased respiratory rate (FIG. 4*e*, FIG. 9). Finally, we tested the adBNST output to the ventral tegmental area (VTA). Remarkably, ChR2:adBNST-VTA mice (FIG. 10*m*) exhibited RTPP in the stimulated chamber (p<0.001; FIG. 10*p*), without affecting anxiety-related risk-avoidance (FIG. 10*n*) or respiratory rate (FIG. 10*o*). These data showing complementary roles of different adBNST projections support a model wherein populations of adBNST neurons project to distinct downstream structures (LH, PB and VTA; FIG. 16), modulating different features of anxiolysis.

FIGS. 9*a-d*. Optogenetic stimulation of the ovBNST increases anxiety-related behavior. FIG. 9*a*) 6-8 week old Drd1a-Cre mice received unilateral injection of 0.5 μl AAV5:EF1α::DIO-ChR2-eYFP (ChR2:ovBNST; n=7) or AAV5:EF::DIO-eYFP (eYFP:ovBNST; n=7) in the ovBNST and were implanted with fiberoptics directly above the ovBNST. Behavioral assays were performed 4 weeks after injection. (b) Mice were run on the elevated plus maze for a 15-min session, consisting of three 5-min light OFF/ON/OF epochs. Blue light stimulation delivery during the ON epoch (5 ms pulse width, 10 Hz) in the ChR2:BNST somata group decreased open-arm time and open-arm entry probability (inset) relative to eYFP controls ($F_{2,24}=6.208$, p<0.05; inset: $F_{224}=4.078$, p<0.05). (c) A week later, mice were run on the open field for a 20-min session, consisting of 5-min light OFF/ON/OFF/ON epochs. Blue light stimulation decreased center time in the OFT during light ON epochs compared to eYFP controls (left, $F_{3,36}=2.311$, p=0.927; right, $F_{1,12}=6.206$, p<0.05). (d) A week later, respiratory rate was measured from the same mice for 6 min, and the light stimulation was given for the last 3 minutes. Light stimulation increased respiratory rate (p<0.001, Wilcoxon signed-rank test). Values are ±s.e.m. *, , and * indicate p<0.05, 0.01, and 0.001, respectively.

FIGS. 10*a-p*. Distinct adBNST outputs modulate different features related to anxiolysis. (a-d) ChR2:BLA-adBNST mice were transduced in BLA, and unilateral fiberoptics implanted above BLA fibers in adBNST. (a) Light to adBNST increased open-arm time in EPM (n=11 ChR2, n=12 eYFP) (b) and decreased respiratory rate (n=7 ChR2, n=8 eYFP) (c), but did not elicit place preference (n=8 ChR2, n=6 eYFP) (d). (e-h) ChR2:adBNST-LH mice were transduced in BNST, and unilateral fiberoptics implanted above LH (e). In ChR2:adBNST-LH mice, light increased open-arm time in EPM (n=11 ChR2, n=8 eYFP) (f) but did not affect respiratory rate (n=9 ChR2, n=10 eYFP) (g) or place preference (n=7 ChR2, n=7 eYFP) (h). (i-I) ChR2:BNST-PB mice were transduced in BNST, and unilateral fiberoptics implanted in PB (i). Light in ChR2:BNST-PB mice did not influence EPM (n=7 ChR2, n=7 eYFP) (j) but decreased respiratory rate (n=8 ChR2, n=7 eYFP) (k); no effect was seen on place preference (n=7 ChR2, n=5 eYFP) (I). (m-p) ChR2:adBNST-VTA mice were transduced in BNST, and unilateral fiberoptics implanted directly above VTA (m). Light did not affect EPM (n=7 ChR2, n=7 eYFP) (n) or respiratory rate (n=8 ChR2, n=7 eYFP) (o), but induced robust place preference (n=8 ChR2, n=7eYFP) (p). Scale: 200 pm. Meants.e.m.; *=p<0.05; **=p<0.01; '=p<0.001.

Statistics. FIG. 10*b*. n=11 for ChR2:BLA-adBNST group, n=12 for eYFP:BLA-adBNST group. Two-way repeated-measures ANOVA detected significant interaction of group x light epochs: F2,42=5.58, p<0.01. Two groups showed significant difference at light-on epoch: p<0.01, post-hoc Bonferroni t-test. FIG. 10*c*. n=7 for ChR2:BLA-adBNST group, n=8 for eYFP:BLA-adBNST group. p<0.05. Wilcoxon rank-sum test. FIG. 10*d*. n=8 for ChR2:BLA-adBNST group, n=6 for eYFP:BLA-adBNST group. p>0.05. Wilcoxon rank-sum test. FIG. 10*f*. n=11 for ChR2:adBNST-LH group, n=8 for eYFP:adBNST-LH group. Two-way repeated-measures ANOVA detected significant interaction of group x light epochs: F2,34=8.51, p=0.0010. Two groups showed significant difference at light-on epoch: p<0.001, post-hoc Bonferroni t-test. FIG. 10*g*. n=9 for ChR2:adBNST-LH group, n=10 for eYFP:adBNST-LH group. p>0.05. Wilcoxon rank-sum test. FIG. 10*h*. n=7 for ChR2:adBNST-LH group, n=7 for eYFP:adBNST-LH group. p>0.05. Wilcoxon rank-sum test. FIG. 10*j*. n=7 for ChR2:BNST-PB group, n=7 for eYFP:BNST-PB group. Two-way repeated-measures ANOVA failed to detect a significant interaction of group x light epoch: p>0.05. FIG. 10*k*. n=8 for ChR2:BNST-PB group, n=7 for eYFP:BNST-PB group. p<0.05. Wilcoxon rank-sum test. FIG. 10*l*. n=7 for ChR2:BNST-PB group, n=5 for eYFP:BNST-PB group. p>0.05. Wilcoxon rank-sum test. FIG. 10*m*. n=7 for ChR2:adBNST-VTA group, n=7 for eYFP:adBNST-VTA group. Two-way repeated-measures ANOVA failed to detect a significant interaction of group x light epoch: p>0.05. FIG. 10*o*. n=8 for ChR2:adBNST-VTA group, n=7 for eYFP:adBNST-VTA group. p>0.05. Wilcoxon rank-sum test. FIG. 10*p*. n=8 for ChR2:adBNST-VTA group, n=7 for eYFP:adBNST-VTA group. p<0.001. Wilcoxon rank-sum test.

Figure 11:
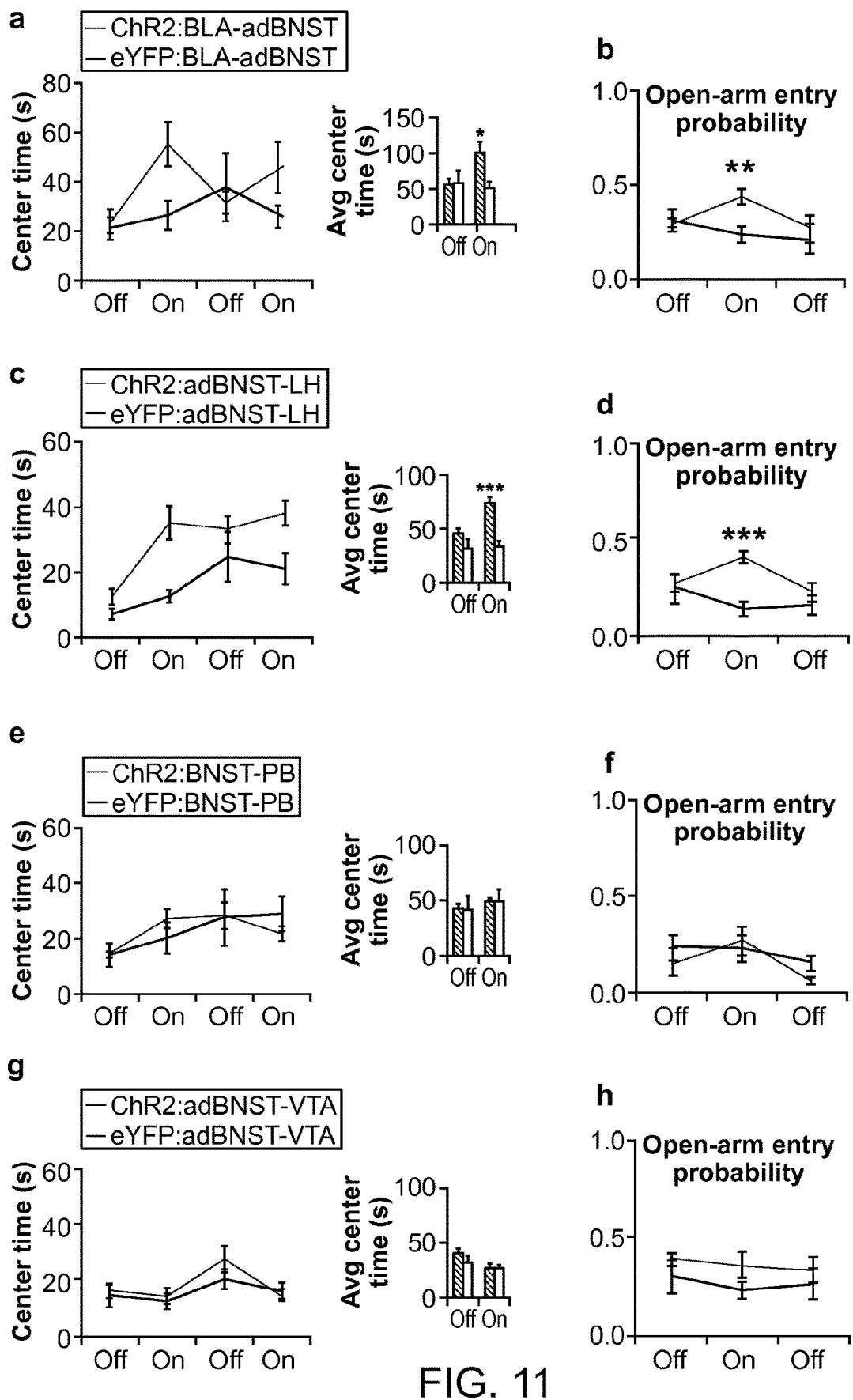
FIGS. 11A-H depict data showing that stimulation of adBNST projection to the LH, but not to the PB or VTA, is anxiolytic.

FIG. 11. Stimulation of adBNST projection to the LDH, but not to the PB or VTA, is anxiolytic.

Blue light in ChR2:BLA-adBNST mice increased center time in the OFT (a) and open-arm entry probability in the EPM (b). Blue light in ChR2:adBNST-LH mice increased center time in the OFT (c) and open-arm entry probability in the EPM (d). Blue light in ChR2:BNST-PB mice had no effect in center time in the OFT (e) and open-arm entry probability in the EPM (f). Blue light in ChR2:adBNST-VTA mice had no effect in center time in the OFT (g) and open-arm entry probability in the EPM (h). Values are mean±s.e.m. *,  and *, indicate p<0.05, 0.01 and 0.001, respectively. Statistical analysis below. Data in this figure are additional behavioral results from the same cohorts shown in FIG. 10.

Statistics. FIG. 11*a*. n=11 for ChR2:BLA-adBNST group, n=11 for eYFP:BLA-adBNST group. Two-way repeated measures ANOVA detected significant interaction of group x light epoch: F3,60=2.89, p<0.05. Two groups showed significant difference at the first light-on epoch: p<0.05, post-hoc Bonferroni t-test. (Inset) Two-way repeated-measures ANOVA detected significant interaction of group x light epoch: F1,20=9.72, p<0.01. Two groups showed significant a difference in the light-on epoch: p<0.05, post-hoc Bonferroni t-test. FIG. 11*b*. n=11 for ChR2:BLA-adBNST group, n=11 for eYFP:BLAadBNST group. Two-way repeated-measures ANOVA detected significant interaction of group x light epoch: F2,42=4.21, p<0.05. Two groups showed a significant difference in the light-on epoch: p<0.01, post-hoc Bonferroni t-test. FIG. 11*c*. n=11 for ChR2:adBNST-LH group, n=8 for eYFP:adBNSTLH group.

Two-way repeated-measures ANOVA did not detect a significant interaction of group x light epoch. (Inset) However, when light-off and light-on epochs were averaged, two-way repeated measures ANOVA detected significant interaction of group x light epoch: $F_{1,17}=5.59$, $p<0.05$. Two groups showed a significant difference in the light-on epoch: $p<0.001$, post-hoc Bonferroni t-test. FIG. 11d. n=11 for ChR2:adBNST-LH group, n=8 for eYFP:adBNSTLH group. Two-way repeated-measures ANOVA detected a significant interaction of group x light epoch: $F_{2,34}=4.41$, $p<0.05$. Two groups showed a significant difference in the light-on epoch: $p<0.001$, post-hoc Bonferroni t-test. FIG. 11e. n=7 for ChR2:BNST-PB group, n=7 for eYFP:BNST-PB group. Two-way repeated-measures ANOVA failed to detect a significant interaction of group x light epoch: $p>0.05$. (Inset) Two-way repeated-measures ANOVA failed to detect significant interaction of group x light epoch: $p>0.05$. FIG. 11f. n=7 for ChR2:BNST-PB group, n=7 for eYFP:BNST-PB group. Two-way repeated-measures ANOVA failed to detect a significant interaction of group x light epoch: $p>0.05$. FIG. 11g. n=8 for ChR2:adBNST-VTA group, n=7 for eYFP: adBNSTVTA group. Two-way repeated-measures ANOVA failed to detect a significant interaction of group x light epoch: $p>0.05$. (Inset) Two-way repeated-measures ANOVA failed to detect a significant interaction of group x light epoch: $p>0.05$. FIG. 11h. n=8 for ChR2:adBNST-VTA group, n=7 for eYFP:adBNSTVTA group. Two-way repeated-measures ANOVA failed to detect a significant interaction of group x light epoch: $p>0.05$.

Figure 12:
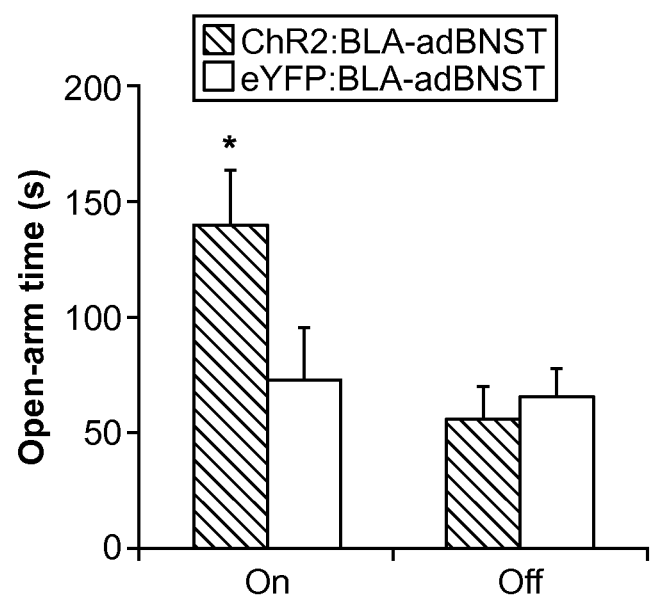
FIG. 12 depicts the effect of optogenetic stimulation of the BLA-adBNST projection on anxiety-related behavior in the EPM in the first 5 minutes of EPM exposure.
Figure 13:
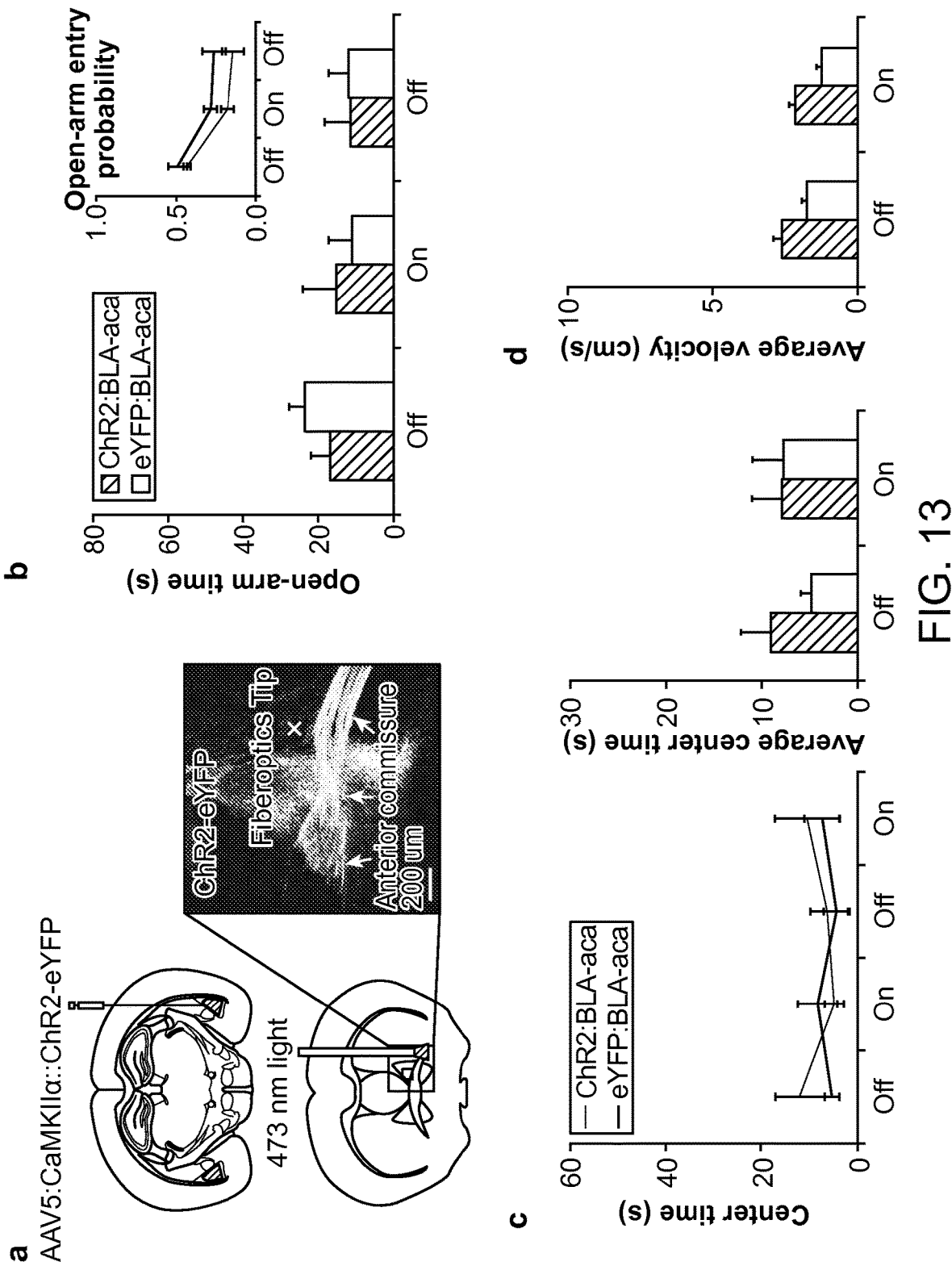
FIGS. 13A-D depict data showing that stimulation of BLA fibers in the anterior commissure (aca) does not affect anxiety-related behavior.

FIG. 12. Optogenetic stimulation of the BLA-adBNST projection reduces anxiety-related behavior in the EPM in the first 5 minutes of EPM exposure. To demonstrate that optogenetic stimulation of the BLA-adBNST projection reduces anxiety-like behavior in the more commonly used 5-minute elevated plus maze test, a separate cohort of group-housed ChR2:BLA-adBNST mice was generated. 6-8 week old mice received a unilateral injection of 0.5 µl AAV5:CaMKIIa::ChR2-eYFP (ChR2:BLA-adBNST; n=8) or AAV5: CaMKIIa::eYFP (eYFP:BLA-adBNST; n=6) in the BLA and were implanted with fiberoptics directly above the BNST. Behavioral assays were performed 8 weeks after injection. Mice were run on the elevated plus maze for a 10-min session, consisting of 5-min light ON/OFF epochs. Blue light stimulation delivery during the ON epoch (5 ms pulse width, 10 Hz) in the ChR2:BLA-adBNST group decreased open-arm time relative to eYFP controls (two-way repeated measures ANOVA, $F_{1,12}=8.347$, $p<0.05$; post-hoc Bonferroni t-test, $p<0.05$ at light ON epoch). Note the presence of an anxiolytic effect in the first 5 minutes (ON epoch). Values are mean±s.e.m.

FIG. 13. Stimulating BLA fibers in the anterior commissure (aca) does not affect anxiety-related behavior. (a) 6-8 week old mice received an unilateral injection of 0.5 µl AAV5:CaMKIIα::hChR2(H134R)-eYFP (ChR2:BLA-aca; n=5) or AAV5:CaMKIIa::eYFP (eYFP:BLA-aca; n=5) in the BLA and were implanted with fiberoptics directly above the BNST. Behavioral experiments were conducted 8 weeks after the injection. Confocal image shows robust expression of ChR2-eYFP in BLA fibers passing through the anterior commissure. Blue light stimulation (5 ms pulse width, 10 Hz) in the ChR2:BLA-aca group (n=5) did not affect open-arm time and probability of open-arm entry in the elevated plus maze test (15-min session divided into 5-min OFF/ON/OFF epochs) (b), center time (c) and locomotor activity in the open field test (20-min session consisting of 5-min OFF/ON/OFF/ON epochs) (d) during light-ON epochs. All $p>0.05$, two-way repeated measures ANOVA. Values are mean±s.e.m.

Figure 14:
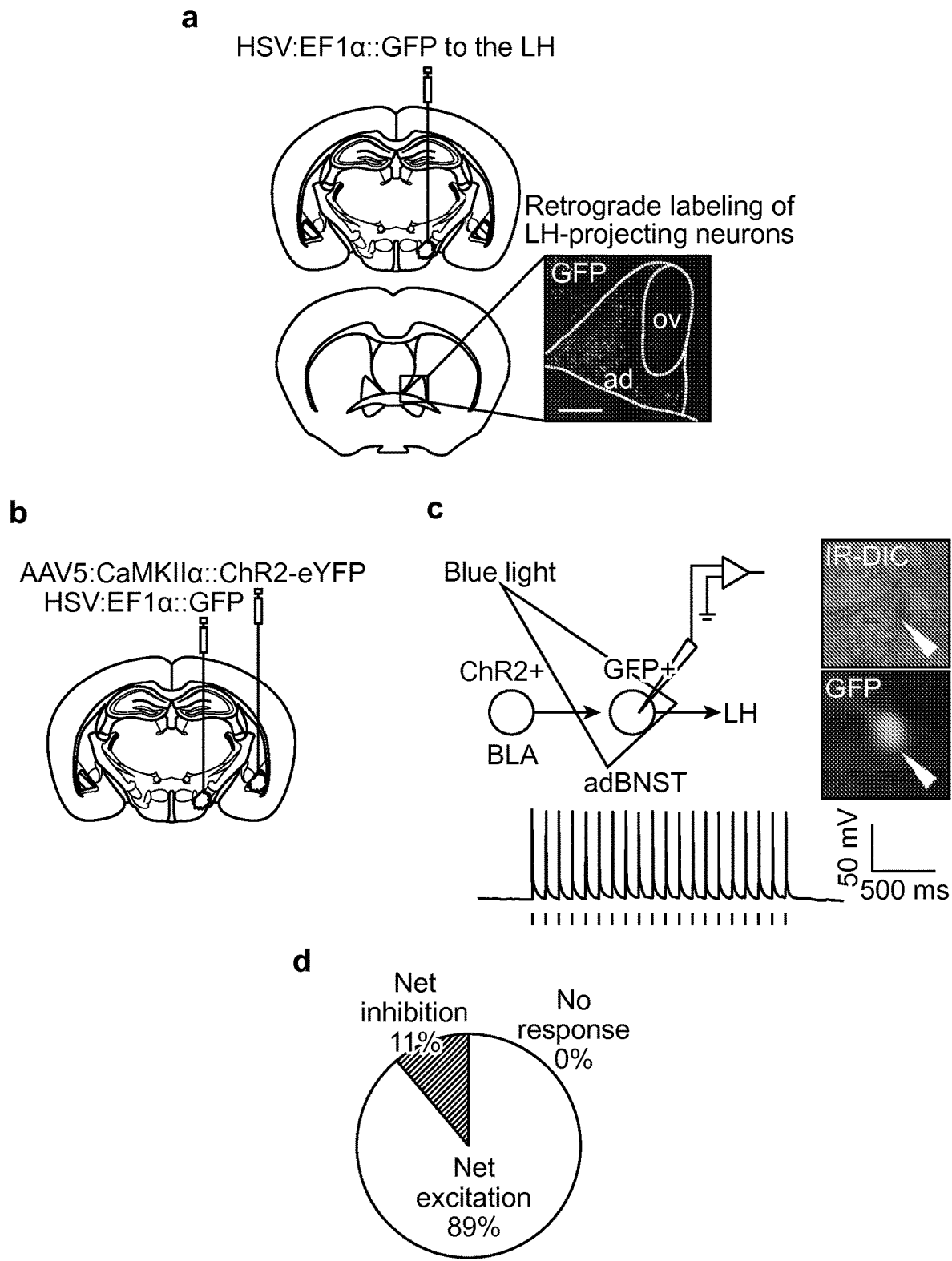
FIGS. 14A-D show that adBNST neurons projecting to the LH are innervated by BLA axon terminals.

FIG. 14. adBNST neurons projecting to the LH are innervated by BLA axon terminals. (a) Three 6 week old mice were injected in the LH with 0.5 µl of herpes simplex virus (HSV), a retrogradely propagating virus, encoding GFP under the EF1α promoter (HSV:EF1α::GFP). 5 days after the injection, mice were perfused and 40 µm coronal sections containing the BNST were prepared for confocal microscopy. GFP-positive retrogradely-labeled neurons were observed only in the adBNST, but not in the ovBNST, in all mice. Representative confocal image shows zmax projection of a 12 µm section. Scale bar, 200 µm. (b) Three 6 week old mice were injected with 0.5 µl HSV:EF1α::GFP in the LH and with 0.5 µl AAV5:CaMKIIa::ChR2-eYFP in the BLA. 3-5 days after the injection, acute slices containing the BNST were prepared for slice patch-clamp recording. (c) GFP-expressing neurons in the adBNST were recorded during optical stimulation of BLA terminals in the BNST. Representative current-clamp trace from a GFP(+) adBNST neuron (Vm=~−60 mV) is shown at the bottom. (d) Most neurons were excited at resting potential in current clamp mode (8/9 neurons). Remarkably, every labeled neuron showed light-evoked responses (n=9 adBNST neurons).

Figure 15:
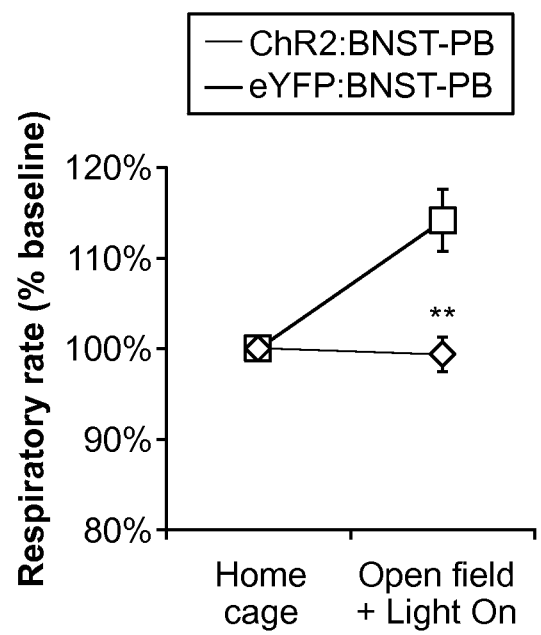
FIG. 15 depicts data showing that respiratory rate increase in an anxiogenic environment is attenuated by stimulating the BNST-PB projection.
Figure 16:
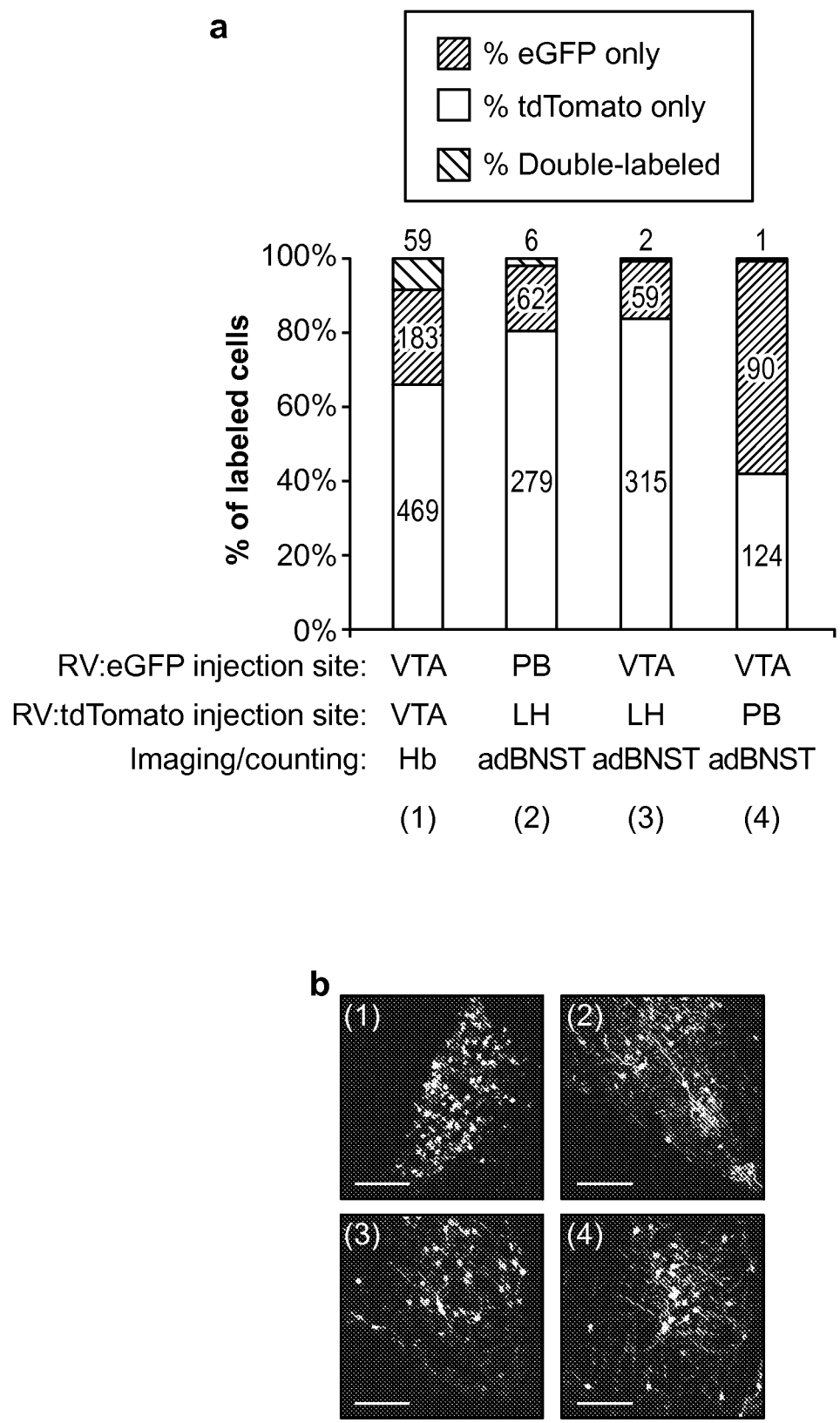
FIGS. 16A and 16B depict data showing that subpopulations of adBNST neurons project to the LH, PB, and VTA.

FIG. 15. Respiratory rate increase in an anxiogenic environment is attenuated by stimulating the BNST-PB projection. 10 week old mice received unilateral injection of 0.5 µl AAV5:hSyn::ChR2-eYFP (ChR2:BNST-PB; n=7) or AAV5: hSyn::eYFP (eYFP:BNST-PB; n=5) in the BNST and were implanted with fiberoptics directly above the PB. The experiment began 16 weeks after the injection. Mice were handled for 3 days and acclimated to the collar clip for the respiratory rate measurement. Respiratory rate was first recorded in the home cage or the open field for 3 min. Mice were allowed to rest in a new clean cage for 5 min, and were then recorded in the other environment for 3 min. Blue laser stimulation was delivered (5 ms pulse width, 10 Hz) in the open field. The order of recording environments was counterbalanced across animals. Respiratory rate was significantly increased by placing the animals into an open field paired with light stimulation in eYFP:BNST-PB mice compared to the values measured in the home cage. This increase was significantly attenuated in ChR2:BNST-PB mice ($p<0.01$, Wilcoxon rank-sum test), indicating that stimulating the BNST-PB projection is sufficient to reduce an anxiogenic stimulus-elicited increase in respiratory rate.

FIG. 16. Subpopulations of adBNST neurons project to the LH, PB and VTA. (a-b) To examine the degree of overlap between subpopulations of BNST neurons that project to LH, PB and VTA, 0.5 µl of rabies virus encoding eGFP (RV:eGFP) and tdTomato (RV:tdTomato) were injected in the indicated regions of 6 week old mice. Four days after the injection, mice were perfused and 40 µm coronal sections were prepared for confocal microscopy. (a) Summary plot of % labeled adBNST neurons. Injecting a mixture of RV-eGFP and RV-tdTomato viruses in the VTA yielded 8.3% double-labeled neurons in the habenula (Hb). However, injecting RV:eGFP and RV:tdTomato into any two of LH, PB or VTA co-labeled very few BNST neurons (1.7% for PB/LH, 0.5% for VTA/LH, 0.0% for VTA/PB). All groups displayed a significantly smaller fraction of co-labeled cells than the positive control VTA-VTA group ($p<0.0001$), suggesting that subpopulations of adBNST neurons projecting to the LH, PB and VTA are not completely overlapping. Numbers indicate cell counts. (b) Representative images showing fluorophore expression in the indicated regions (green:

eGFP, red, tdTomato, yellow: double-labeled). (1), single plane; (2-4) z-max projections of 20-μm sections. Scale bar, 100 μm. Note that another positive control showing that neurons can get infected twice by these same rabies virus preparations can be found in Lammel et al. *Nature*, 2012 Nov. 8; 491(7423):212-7 (2012). Statistical analysis below.

FIG. 16 Statistics: Chi-square test detected significant differences between: (1)(2) ($X^2(^1$, n=347)=19.132, p<0.0001), $(^1)$-$(^3)$ ($X^2(^1$, n=376)=29.567, p<0.0001) and (1)(4)$_{(X2(1,}$ n=215)=17.287, p<0.0001).

Figure 17:
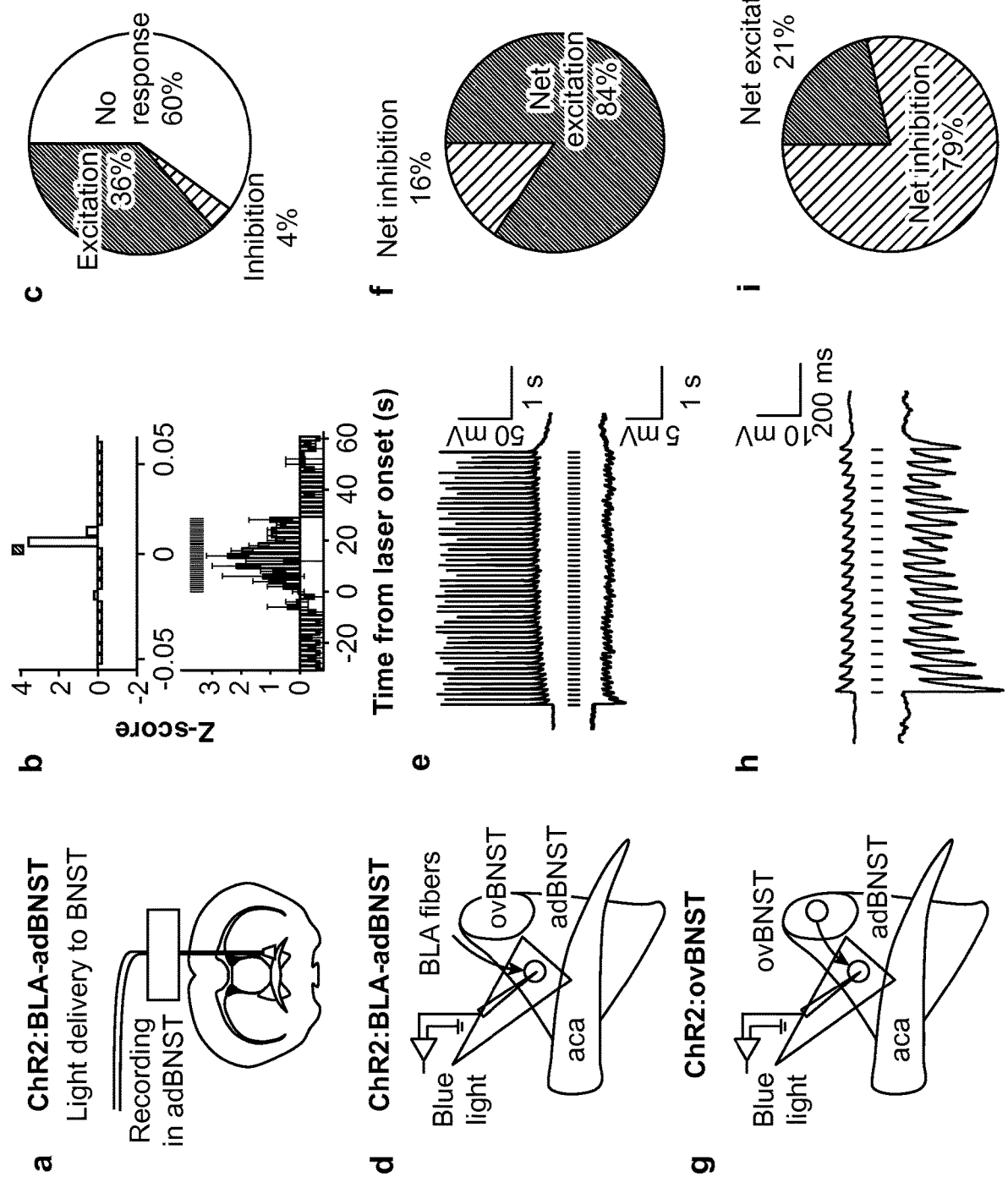
FIGS. 17A-I depict in vivo and in vitro electrophysiological assessment of adBNST afferents.
Figure 19:
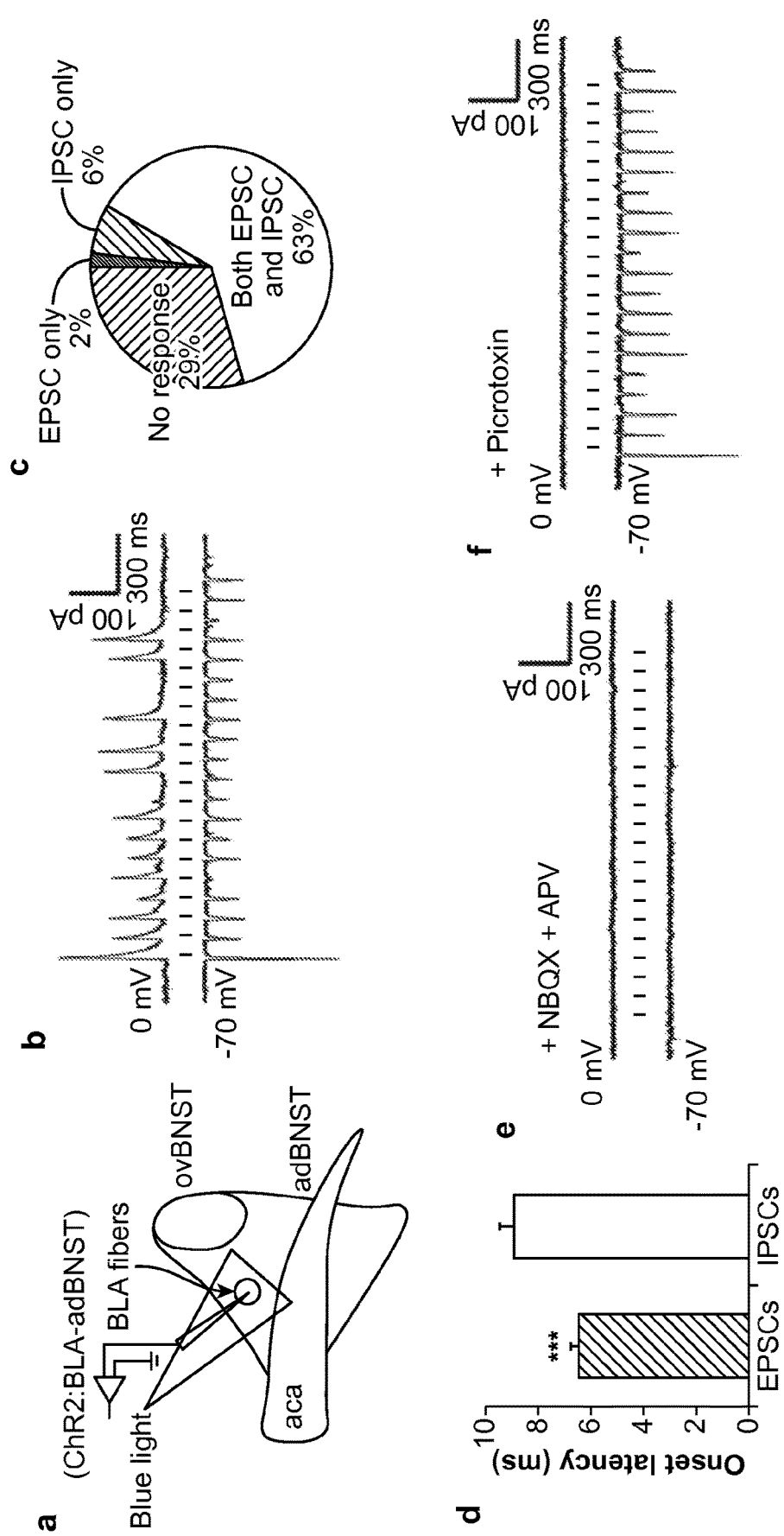
FIGS. 19A-L depict evidence for feed-forward inhibitory and excitatory circuitry in the adBNST.
Figure 19:
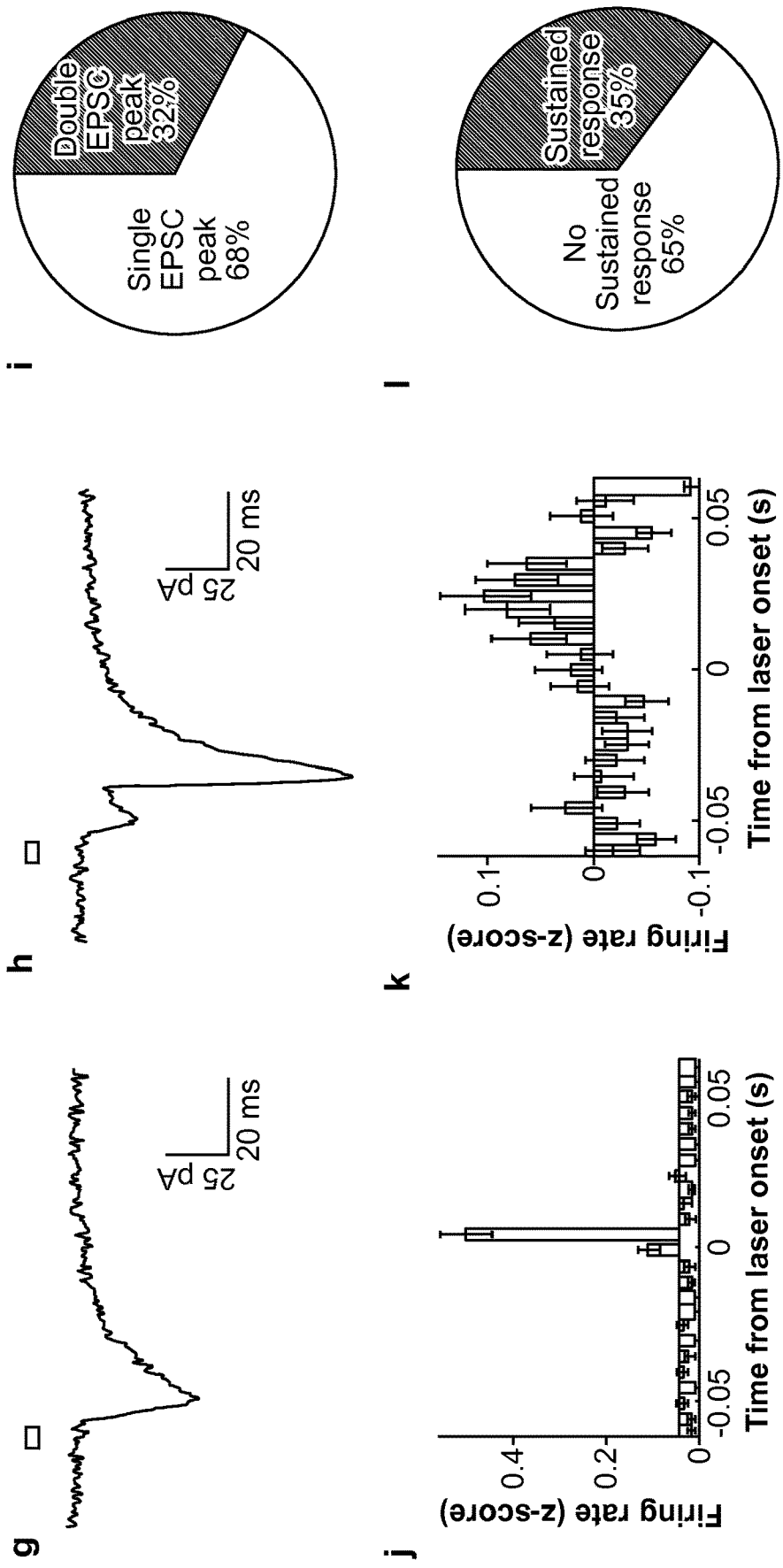
Figure 20:
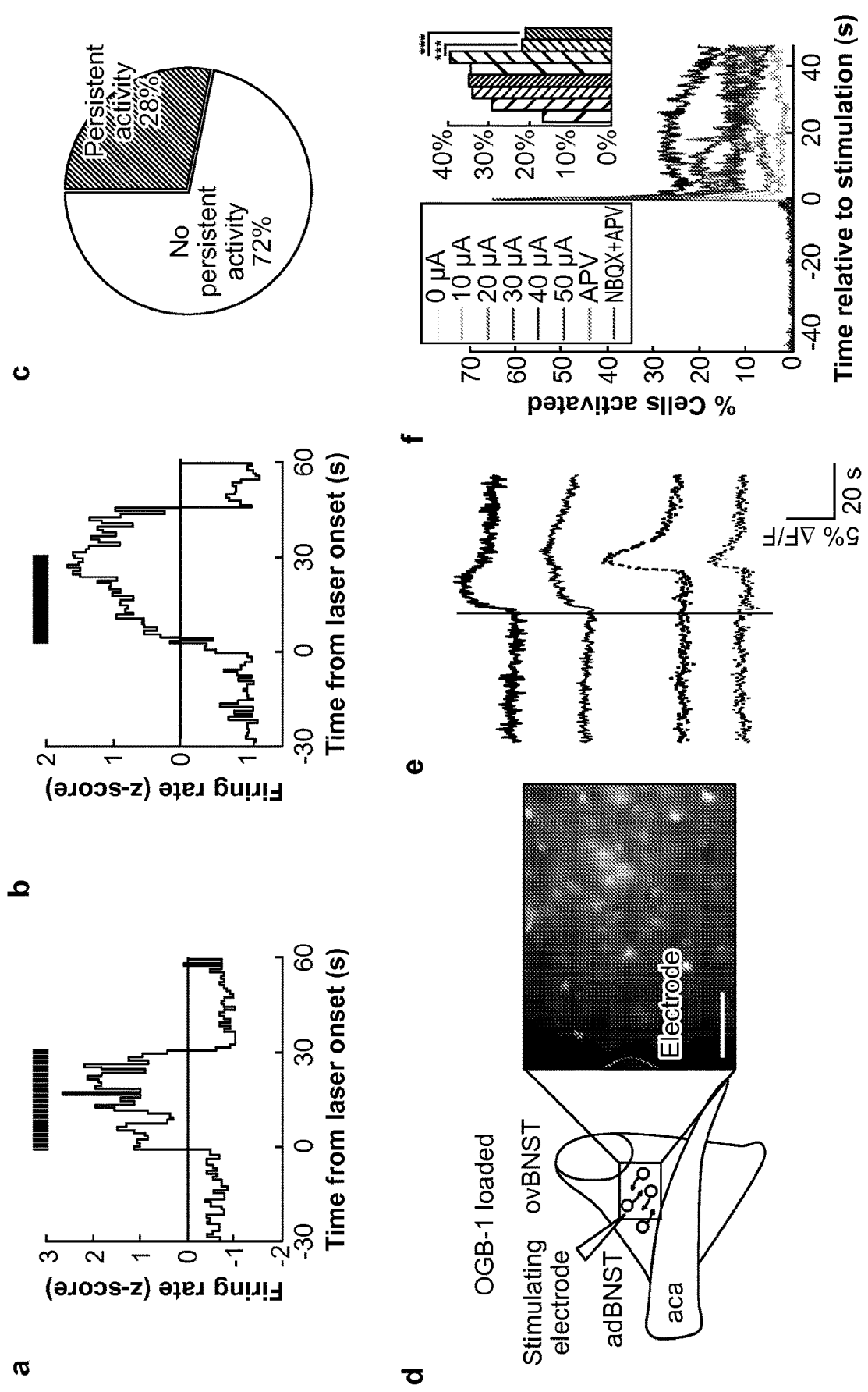
FIGS. 20A-I depict data showing that recurrent excitation may enable coordinated recruitment of BNST downstream projections.
Figure 20:
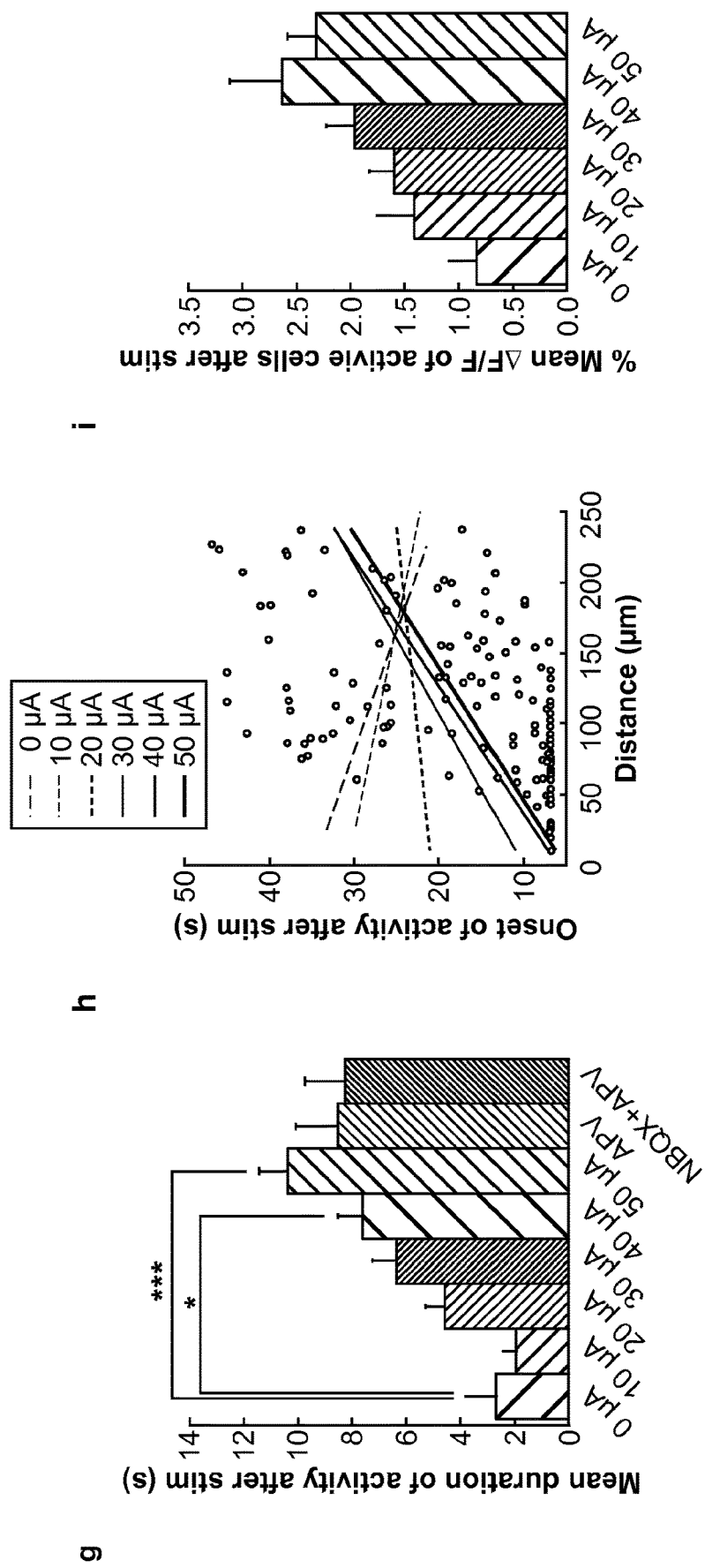
Figure 21:
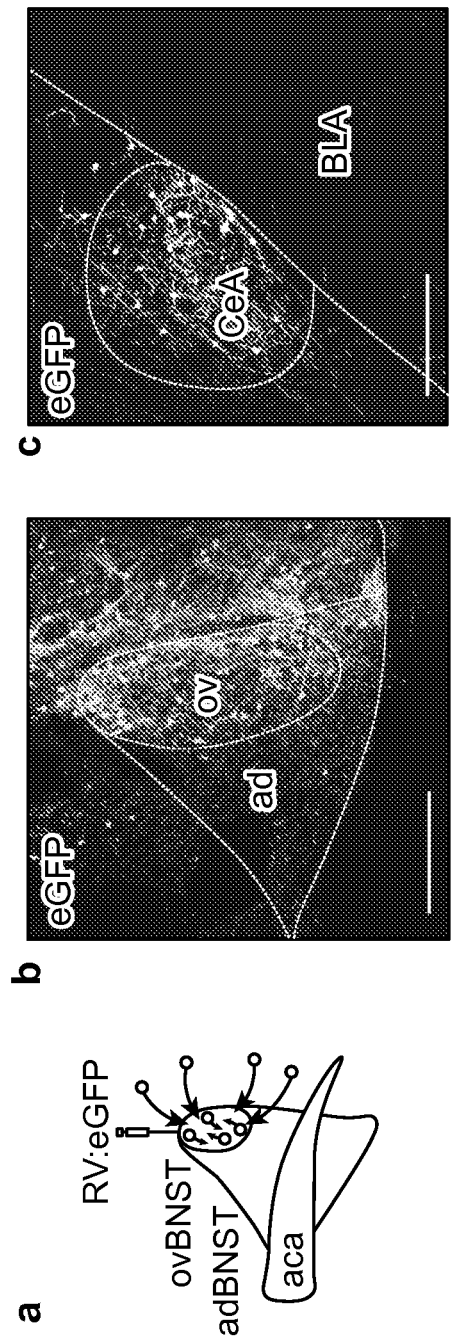
FIGS. 21A-C depict adBNST projecting weakly to the ovBNST.

We next investigated the intrinsic microcircuitry of the adBNST. To examine connectivity between the BLA and the adBNST, mice expressing ChR2 in the BLA were implanted with a microdrive containing stereotrodes surrounding a fiberoptic in the adBNST (FIG. 17a, FIG. 18), allowing simultaneous excitation and recording in awake animals. As expected, excitation of the glutamatergic BLA terminals increased spiking of adBNST single units (FIGS. 17b and 17c), and corresponding whole-cell patch recordings from acute slices revealed that 84% of the adBNST neurons exhibiting both evoked EPSCs and IPSCs in voltage clamp (Methods; FIG. 19) displayed net excitation in response to BLA input stimulation in current clamp (FIGS. 17d-f). Thus, in vivo and in vitro electrophysiology were concordant in showing that stimulating the BLA-adBNST projection increases adBNST activity, which may be enhanced by local adBNST recurrent excitation (FIGS. 19 and 20). We also characterized local inputs to the adBNST, by recording from adBNST neurons while optically stimulating ovBNST inputs (FIG. 17g). Interestingly, 79% of neurons displayed net inhibition (FIGS. 17h and 17i), consistent with the fact that ovBNST neurons are mostly GABAergic; in contrast, retrograde tracing experiments showed that the adBNST only weakly projects to the ovBNST (FIG. 21). Together these data support the conclusion that the ovBNST and adBNST exhibit opposing roles in modulating anxiety.

FIGS. 17a-i. In vivo and in vitro electrophysiological assessment of adBNST afferents. (a-f) Assessment of BLA afferents to adBNST. (a) ChR2:BLA-adBNST mice were implanted with a microdrive containing 8 stereotrodes and a fiberoptic in adBNST to allow simultaneous optogenetic stimulation/recording of adBNST neurons. (b) Representative PSTHs of adBNST single units in behaving mice, showing typical response to 5 ms light-pulse (top), and to a 10 Hz light-pulse train for 20s (bottom). Excitation was most commonly observed (n=55). (d) ChR2 was expressed in the BLA; acute slices were prepared from BNST, and BNST neurons were recorded in current-clamp while optically stimulating BLA afferents. (e) Representative traces from adBNST neurons ($V_m$=−60 mV), displaying excitatory (top) and inhibitory (bottom) responses. (f) Among adBNST neurons that showed both EPSCs and IPSCs, most were excited at resting potential (n=16/19 neurons; see FIG. 19 for voltage-clamp). (g-i) Electrophysiologically-assessed functional connectivity from ovBNST to adBNST (FIG. 21) illustrates minimal connectivity in the reverse direction). (g) ChR2 was expressed in ovBNST using Drd1a-Cre line mice; adBNST neurons were recorded while stimulating ovBNST fibers. (h) Representative current-clamp traces from adBNST neurons ($V_m$=−60 mV), exhibiting excitatory (top) and inhibitory (bottom) responses. (i) Among adBNST neurons that showed both EPSCs and IPSCs, most were inhibited at resting potential (n=11/14 neurons). Meant-s.e.m.; Statistics. FIG. 3c. n=55 adBNST single units. FIG. 3f. n=19 adBNST neurons. FIG. 17I. n=14 adBNST neurons.

Figure 18:
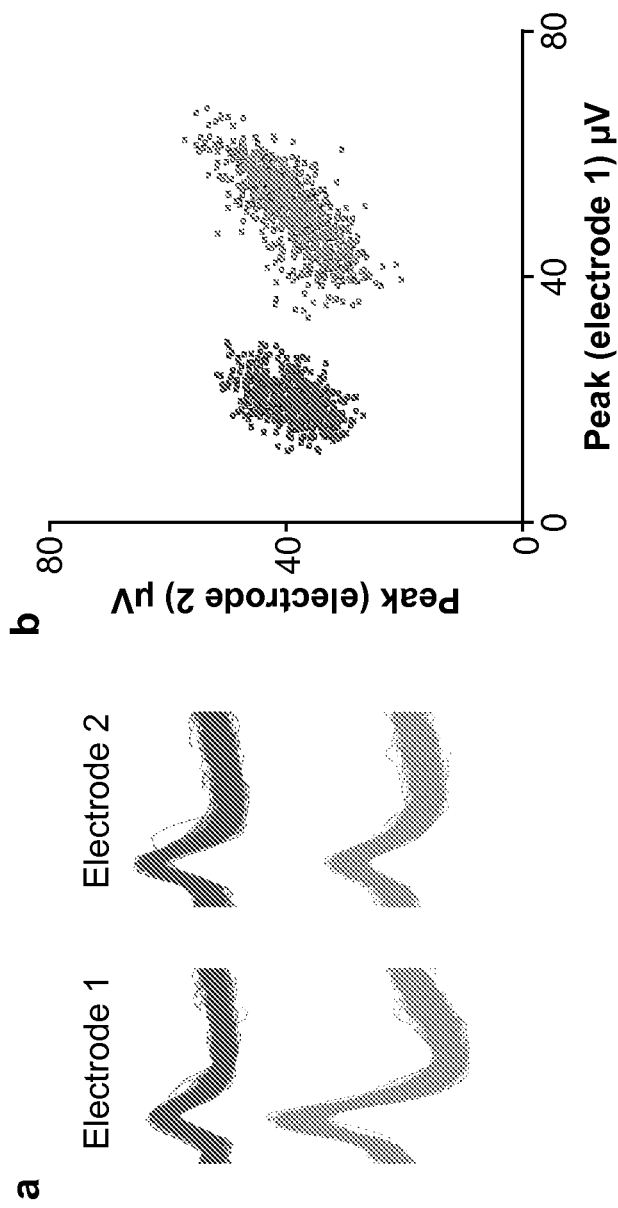
FIGS. 18A and 18B depict isolation of single units via stereotrodes.

FIG. 18. Isolation of single units via stereotrodes. Mice were implanted with microdrives containing 8 tungsten stereotrodes. (a) Examples of spikes from two adBNST single units simultaneously recorded by the same stereotrode. (b) Scatterplot of peak on electrode 1 against peak on electrode 2. The spikes from these two single units form well-isolated clusters. Spikes were sorted offline using SpikeSort3D software (Neuralynx).

FIG. 19. Evidence for feed-forward inhibitory and excitatory circuitry in the adBNST. To examine the connectivity between the BLA and BNST, (a) eight 4-week old mice were injected with 0.5 μl AAV5:CaMKIIa::ChR2-eYFP in the BLA. 4 weeks after injection, acute slices containing the BNST and BLA axon fibers were prepared for slice patch-clamp recording. See FIG. 3 for related current-clamp and in vivo recording experiments. (b) Representative voltage-clamp traces from an adBNST neuron held at 0 mV (top) and −70 mV (bottom), displaying IPSCs and EPSCs in response to 10 Hz, 5-ms blue light pulses. (c) Most light-responsive neurons exhibited both EPSCs and IPSCs (n=48 adBNST neurons). These IPSCs are likely not monosynaptic, but indirectly driven by local adBNST neurons, since: 1) we optogenetically stimulated an excitatory projection, 2) EPSCs had shorter latencies than IPSCs (p<0.001; see (d) below), and 3) bath application of the excitatory-glutamate receptor antagonists NBQX (2,3-dihydroxy-6-nitro-7-sulfamoyl-benzo[f]quinoxaline-2,3-dione) and APV ((2R)-amino-5-phosphonopentanoate) blocked both EPSCs and IPSCs, whereas bath application of the GABAA receptor antagonist picrotoxin blocked only IPSCs (see (e,f) below). (d) Onset latency of EPSCs was shorter than that of IPSCs (n=14 for EPSCs, n=16 for IPSCs. p<0.001, Wilcoxon ranksum test). (e) Bath application of 10 μM NBQX and 50 μM APV abolished both IPSCs and EPSCs (n=4) (top), whereas (f) 100 μM picrotoxin blocked IPSCs but not EPSCs (n=4) (bottom). Representative voltage-clamp traces from adBNST neurons held at −70 mV, displaying single peak (g) or double peaks (h) in response to a 5-ms blue light pulse. (i) Summary of responses observed in the adBNST neurons that exhibited EPSCs (n=31). Four 6 week old mice were injected with 0.5 μl AAV5:CaMKIIa::ChR2-eYFP in the BLA and implanted with a drivable microdrive containing 8 stereotrodes and a fiberoptic in adBNST to allow simultaneous optogenetic stimulation and recording of adBNST neurons. Representative PSTHs of adBNST single unit recordings showing increased activity time-locked to a 5-ms laser pulse (j) or persistent activity even after the end of the laser pulse (k). (l) Summary of adBNST single units that exhibited excitatory responses to blue light (n=20). Together with the results from FIG. 3, these data demonstrate that the adBNST neurons receive both direct excitatory inputs and indirect inhibitory inputs from the BLA, but the most common net response is excitation.

FIG. 20. Recurrent excitation may enable coordinated recruitment of BNST downstream projections. (a-c) Same experiment as FIG. 3a-c. ChR2:BLA-adBNST mice implanted with fiberoptic-stereotrode array in the adBNST received a 10-Hz light pulse train (5 ms pulse width) for 30-s period (bottom). Recruitment of different populations of adBNST projection neurons could involve recurrent excitation in the adBNST, consistent with findings from these in vivo multiunit recordings; persistent activity was seen in 28% of recordings after the end of BLA fiber stimulation. Shown are representative PSTHs of adBNST multiunit recordings showing increased activity time-locked to a laser pulse train. The example in (b) but not in (a), exhibits persistent activity even after the end of laser stimulation. (c)

Summary of adBNST multiunit recordings (n=103). (d) To test for persistent activity in a reduced BNST slice, we performed Ca2+ imaging, and found persistent activity in the adBNST slice following a single brief 0.2 ms stimulus. Oregon Green BAPTA-1 (OGB-1)-loaded adBNST neurons (image) were monitored in response to varying current levels of electrical stimulation. (e) Representative trace of cells showing persistent activity induced by 0.2-ms electrical stimulation, including late onset activation for neurons over 100 µm from the electrode. Location of each color-coded cell is indicated in (d). Vertical line indicates the time of electrical stimulation. (f) The fraction of activated cells increased with ascending electrical stimulation amplitude, and was reduced by over 40% after bath application of either 100 µM APV alone or 10 µM NBQX and 100 µM APV. (Histogram bin size: 234 ms=1 frame). (g) Duration of activation of neurons was enhanced by increasing amplitude of electrical stimulation indicating recruitment of persistent activity. Interestingly, while the fraction of activated neurons was reduced after application of NBQX and APV, the duration of activation for activated neurons was similar to the control condition (50 µA), suggesting that the reduction of excitatory transmission in the APV and NBQX conditions did not completely block persistent activity. (h) Scatterplot of onset of activity evoked by the 50 µA stimulus against the distance of the cell from the electrode tip. Regressed lines for different stimulation intensity are shown, indicating a propagation of onset of activity over distance (p<0.001 for 30, 40 and 50 µA stimulus conditions). (i) Mean ΔF/F of activated cells following electrical stimulation. Activity of cells averaged over the post-stimulation period (% ΔF/F) that were activated by electrical stimulation shows an increasing trend as the stimulation intensity is increased. Values are mean±s.e.m. * and *** indicate p<0.05 and 0.001, respectively. Statistical analysis is provided below.

TABLE 3

FIG. 20 Statistics. FIG. 20f-i. n for each condition is listed in the table below

| Condition | N (number of cells activated after stimulation) | N (all cells) |
|---|---|---|
| 0 µA | 37 | 220 |
| 10 µA | 109 | 370 |
| 20 µA | 127 | 370 |
| 30 µA | 130 | 369 |
| 40 µA | 129 | 372 |
| 50 µA | 148 | 371 |
| APV | 61 | 277 |
| NBQX + APV | 59 | 279 |

FIG. 20f. Chi-square test detected significant differences between: 0 µA-50 µA ($X^2(1, n=220)=49.26$, p<0.0001), 50 µA-APV ($X^2(1, n=277)=37.31$, p<0.0001) and 50 µA-NBQX+APV ($X^2(1, n=279)=41.32$, p<0.0001). FIG. 20g. One-way ANOVA detected significant main effect of stimulation condition: $F_{7,792}=8.512$, p<0.001. Post-hoc Tukey's test revealed significant differences between: 0 µA-50 µA (p=0.001), 10 µA-30 µA (p=0.019), 10 µA-40 µA (p=0.001), 10 µA-50 µA (p<0.001), 10 µA-APV (p=0.001), 10 µA-NBQX+APV (p=0.003), 20 µA-50 µA (p<0.001) and 30 µA-50 µA (p=0.022). FIG. 20h. n=137 adBNST neurons. Spearman's rho and p values:

TABLE 4

| Condition | N | Spearman's rho | p |
|---|---|---|---|
| 0 µA | 84 | −0.2542 | 0.1289 |
| 10 µA | 96 | −0.1326 | 0.1692 |
| 20 µA | 119 | 0.12 | 0.1791 |
| 30 µA | 133 | 0.3901 | $4.48 \times 10^{-6}$ |
| 40 µA | 126 | 0.457 | $5.22 \times 10^{-8}$ |
| 50 µA | 137 | 0.5729 | $2.76 \times 10^{-14}$ |

FIG. 20i. One-way ANOVA detected significant main effect of stimulation condition: $F_{7,792}=2.222$, p=0.031. Post-hoc Tukey's test failed to detect significant differences between conditions.

FIG. 21. The adBNST weakly projects to the ovBNST. (a) To examine connectivity between the ovBNST and the adBNST, rabies virus in which the glycoprotein is replaced by enhanced green fluorescent protein (RV-eGFP) was injected to the ovBNST. (b) Representative fluorescence image showing eGFP expression in local ovBNST neurons. Note the scarcity of eGFP-expressing neurons in the adBNST, indicating weak projections from the adBNST to the ovBNST. (c) Fluorescence image showing restricted eGFP expression in the CeA in the amygdala. Since the CeA projects to both the ovBNST and the adBNST while the BLA projects only to the adBNST but not to the ovBNST, this result indicates that the RV-eGFP injection in the ovBNST did not spread to the adBNST. All scale bars are 200 µm. All images are z-max projection of 20-µm section.

Next, we asked if the native firing rates of adBNST neurons in freely-moving mice encoded aspects of environmental safety, by recording activity with stereotrode arrays in the adBNST during exploration (FIGS. 22a and 22b). Indeed, greater adBNST multiunit activity was observed in safer locations in two paradigms (closed arms of the EPM and dark compartment of the light-dark test box, FIG. 23). To quantify the extent to which adBNST single units differentiated between closed and open arms in the EPM, we defined an EPM-score (see Methods; FIG. 24), in which a positive score indicates that firing rates are similar between arms of the same type (such as a pair of closed arms), but different across open and closed arms (e.g. FIG. 22c). This metric allowed calculation of specific EPM performance-related activity for each single unit both in light-on and light-off epochs. Without illumination, a subset of adBNST single units fired preferentially in the closed arms of the EPM, while other units did not exhibit preference (FIG. 22c). In fact, every adBNST single unit with a positive EPM score (66% of units) had higher firing rates in the closed arms than in the open arms, whereas simulations predict that if there were no dependence on environmental condition, only 33% of cells would have a positive EPM score, and those would be evenly divided between closed and open arm-preferring units (Methods).

Figure 25:
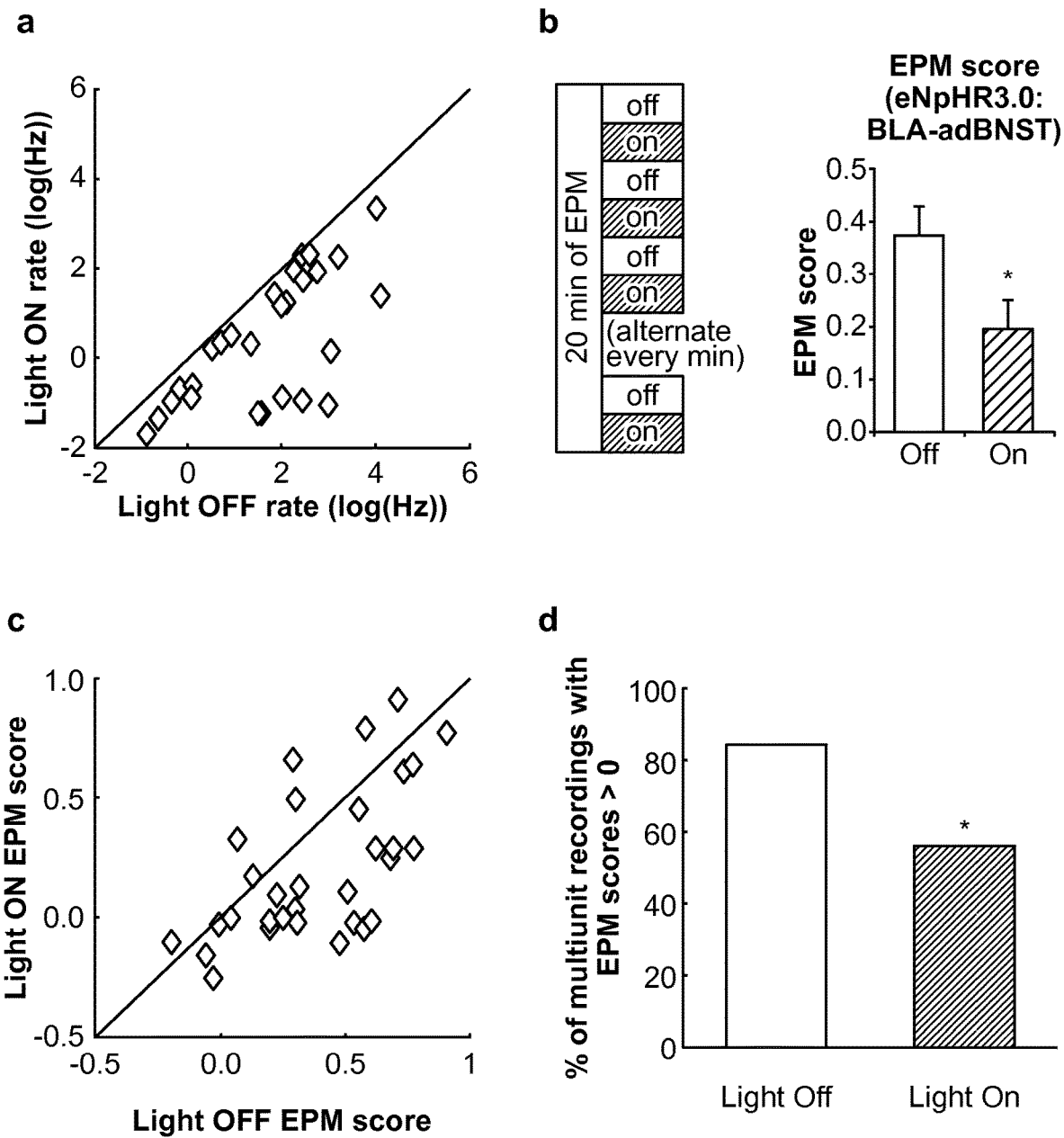
FIGS. 25A-D depict data showing that adBNST multiunit activity depends on BLA inputs to differentiate safe and aversive locations on the EPM.
Figure 26:
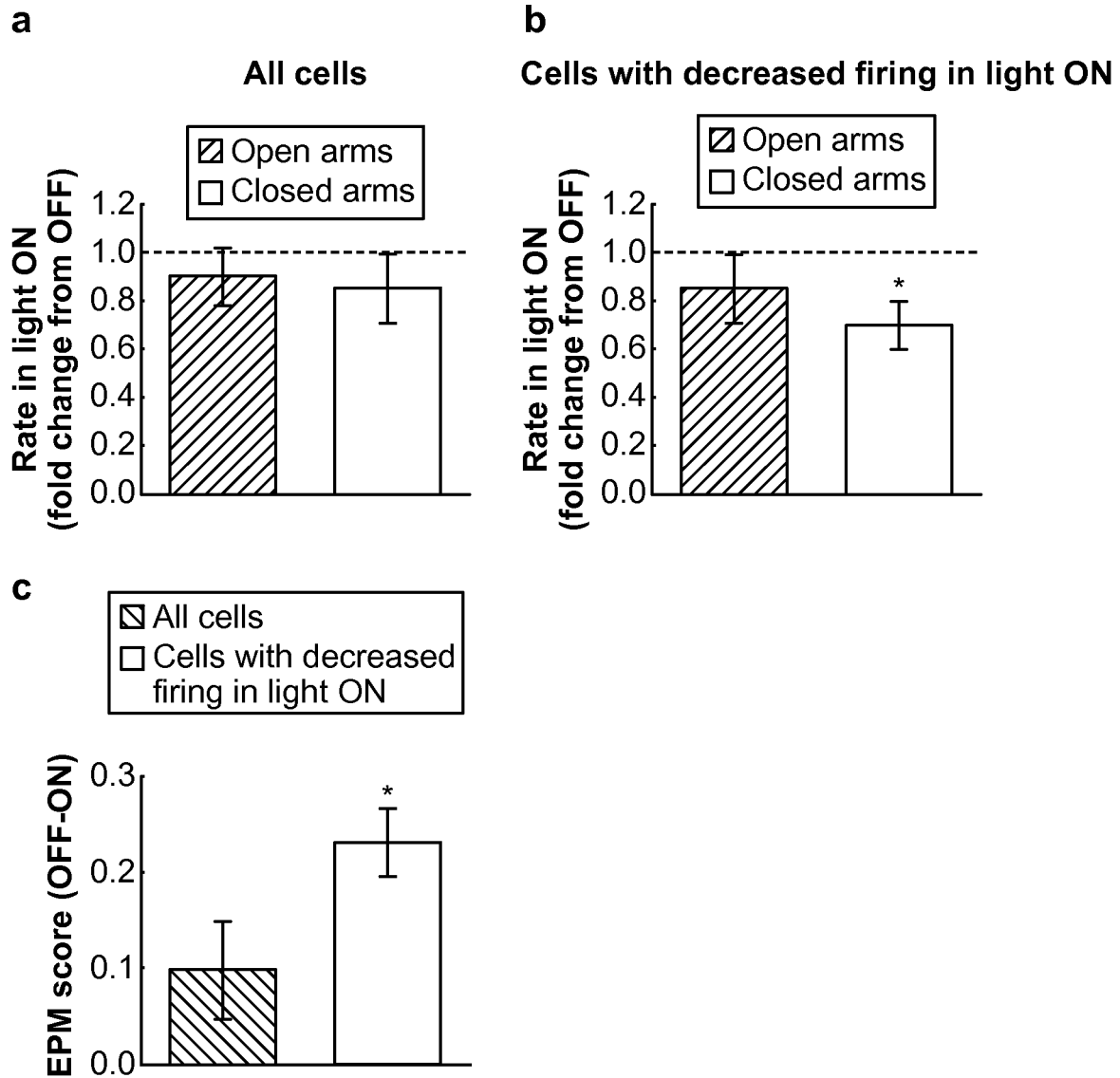
FIGS. 26A-C depict the effect of inhibiting the BLA-adBNST projection on firing rates in the closed arms and EPM scores.

We then implanted stereotrodes and a fiberoptic in the adBNST of eNpHR3.0:BLA-adBNST mice (FIG. 22a), allowing simultaneous recording and yellow light delivery to the adBNST. Illumination in these mice reduced multiunit activity in the adBNST (FIG. 22d; FIG. 25). Finally, we recorded from adBNST single units in eNpHR3.0:BLA-adBNST mice during the EPM test for 20 minutes, with alternating 1-min light off and on epochs (FIG. 22e), to allow calculation of EPM scores for each single unit in the presence or absence of inhibition of BLA afferents. Suggesting that representation of anxiety-related features in the adBNST may depend on BLA input, we observed that optogenetic inhibition of the BLA-adBNST projection decreased single-unit EPM scores (p<0.01; FIGS. 22f and 22g), and the decrease in EPM scores was higher in cells that had decreases in firing rate during the illuminated epochs (FIG. 26). These data indicate that native anxiety-related encoding of the EPM environment in the adBNST depends in part on BLA inputs; note that this same manipulation (inhibiting the BLA-adBNST projection) increased anxiety-like EPM behavior (FIG. 4g), in a manner consistent with causing increased overall anxiety that could deter transitions to the open arm.

Here, we have mapped the role of BNST circuit elements in the assembly and modulation of the anxious behavioral state. We have demonstrated that the ovBNST and adBNST increase and decrease anxiety-related behavior, respectively; the ovBNST could promote anxiety by suppressing the adBNST (see FIG. 27 for summary diagram) or via direct projections to structures such as the central amygdala. We next found that distinct adBNST projections modulate different features of the behavioral state associated with anxiolysis-decreased respiratory rate, positive conditioning valence, and decreased risk-avoidance behavior which are mediated by projections from the adBNST to the PB, VTA, and LH, respectively. This arrangement may facilitate modular adaptation of the state itself over development and experience; in principle, by tuning the strength of diverging projections, distinct features may be independently adjusted while maintaining upstream coordination of the behavioral state. Further work will be needed to determine circuit mechanisms by which functional differentiation of these pathways originates, as well as how coordination ultimately occurs. Coordinated recruitment of the different populations of adBNST projection neurons could involve recurrent excitation (FIGS. 19 and 20); indeed, in vivo multiunit recordings support the existence of recurrent excitation in the adBNST, as persistent activity was seen in 28% of recordings after termination of BLA fiber stimulation (FIGS. 20a-c), and $Ca^{2+}$ imaging in acute BNST slice revealed persistent activity in the adBNST following a single brief stimulus (FIGS. 20d-i).

Figure 22:
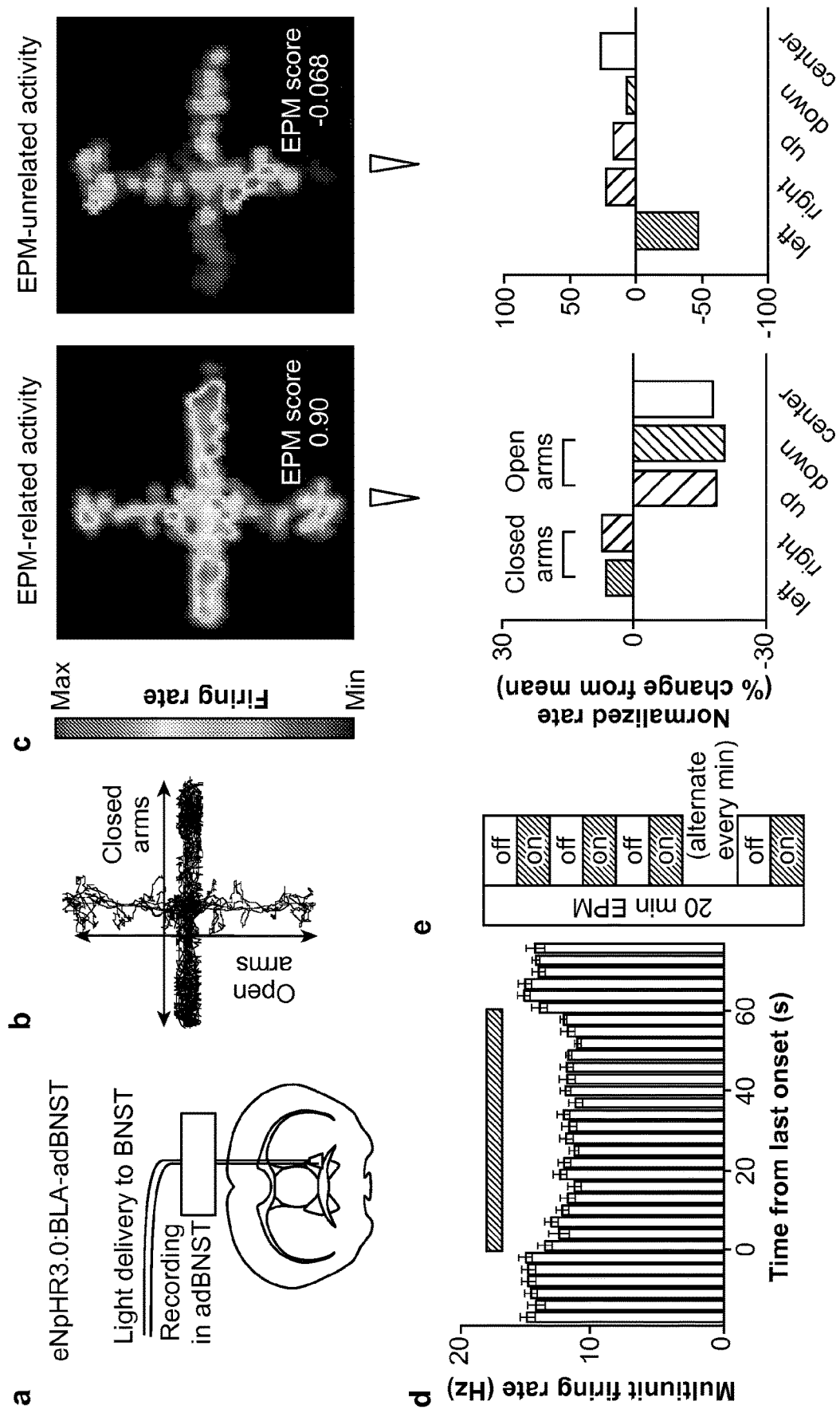
FIGS. 22A-G depict data showing that BNST neurons rely in part on BLA inputs to distinguish safe and anxiogenic locations.
Figure 22:
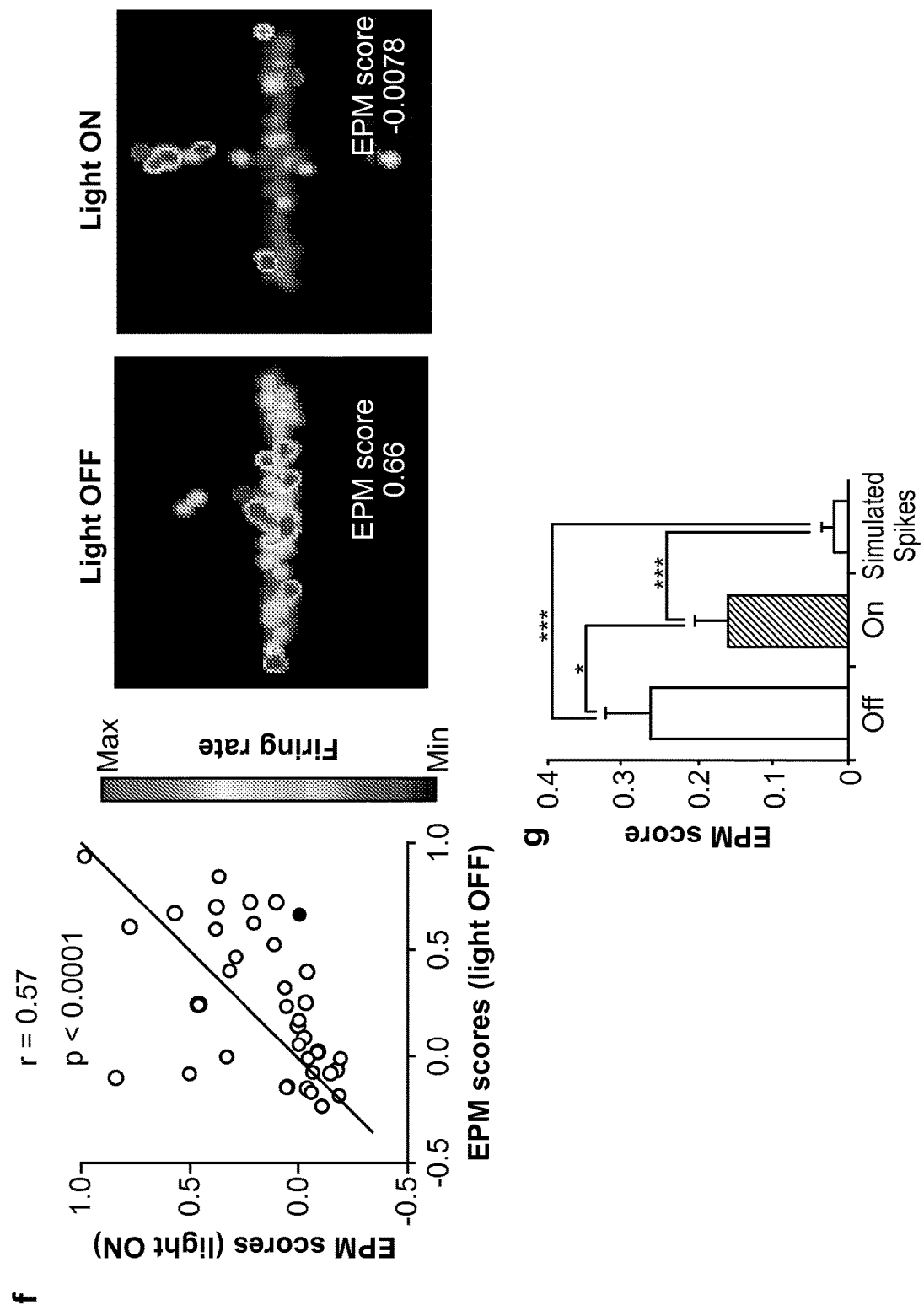

FIGS. 22a-g. BNST neurons rely in part on BLA inputs to distinguish safe and anxiogenic locations. (a) Schematic of in vivo recording configuration. (b) Representative behavioral track tracing from EPM. For all EPM figures, horizontal/vertical arms represent closed/open arms, respectively. (c) Top, spatial firing rate maps of two representative adBNST single units. One unit showed higher activity in closed arms (left), whereas the other did not exhibit preference (right); average normalized firing rates are color-coded for each pixel of spatial location. Bottom, normalized rates (')/0 change from mean firing rate) for each arm for example units. These rates were used to calculate EPM scores (Methods and FIG. 24); higher EPM scores indicate greater differentiation of closed and open arms. Light to inhibit the BLA-adBNST projection modestly suppressed multiunit activity in adBNST. (e) eNpHR3.0:BLA-adBNST mice were run in EPM for 20 min with alternating 1 min light-off and light-on epochs. (f) Left, scatterplot of EPM scores in light-off and light-on conditions. Right, spatial firing maps illustrating change in EPM score of one single unit (red point in scatterplot) in response to yellow light, which decreased EPM score of most (n=28/38) units. (g) Summary data across single units (n=38): mean change in EPM score with inhibition of the –adBNST projection. Notably, EPM scores even in light-on epochs were significantly higher than EPM scores generated from random simulated spikes (p<0.01), indicating that even in light-on, BNST units could differentiate closed and open arms, although less robustly than in light-off. Mean±s.e.m.; *=p<0.05; *=p<0.001. Statistics. FIG. 22f. n=38 adBNST single units. Spearman's rho=0.57, p<0.0001. FIG. 22**g. n=38 adBNST single units. EPM score in light-on epoch was smaller than EPM score in light-off epoch: p<0.05, Wilcoxon rank-sum test. EPM score generated from jittered spikes was smaller than EPM scores in light-on and -off epochs: p<0.001 for both, Wilcoxon rank-sum test.

Figure 23:
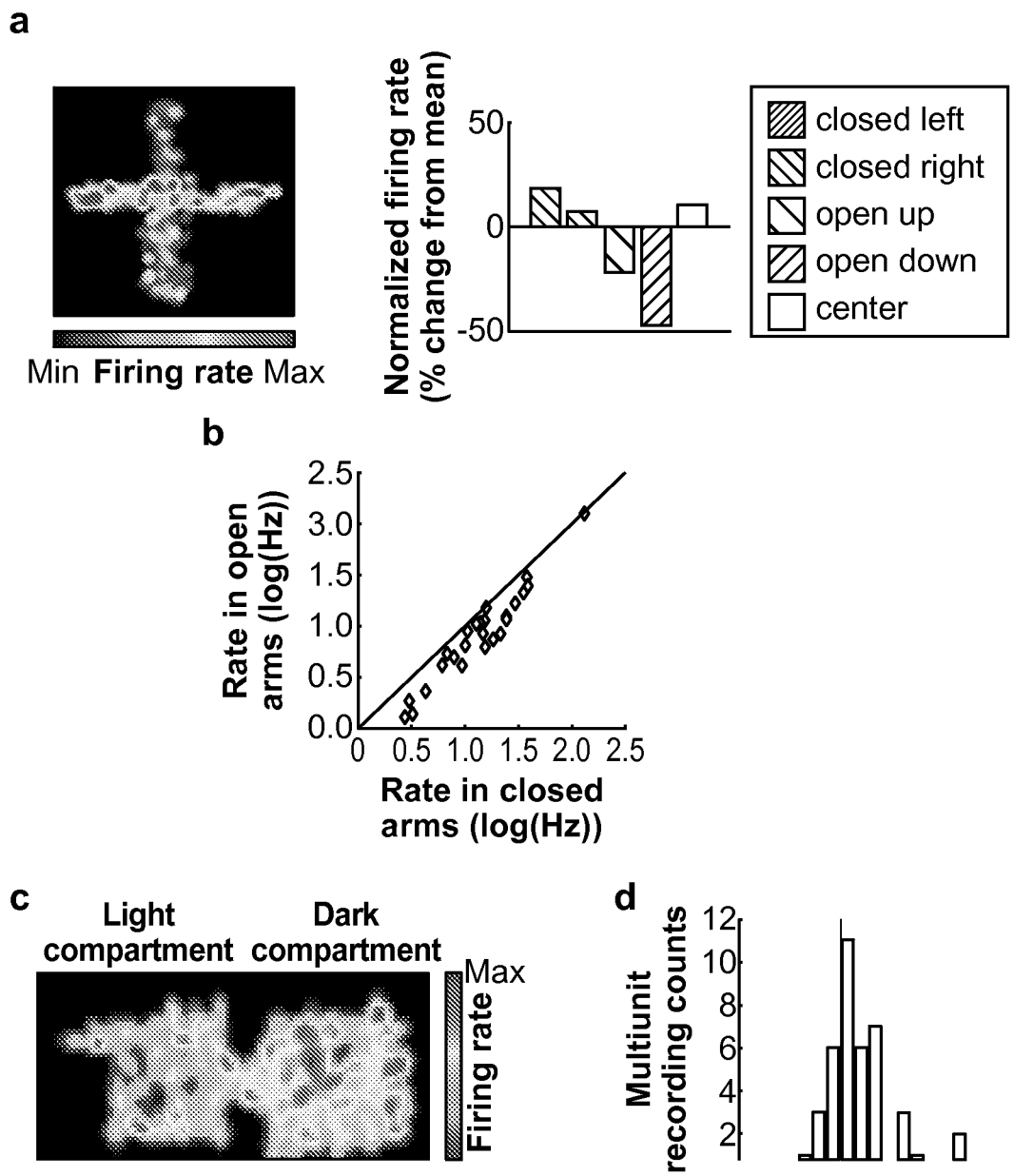
FIGS. 23A-D depict data showing that adBNST multiunit activity is higher in the safe compartments of anxiety paradigms.
Figure 24:
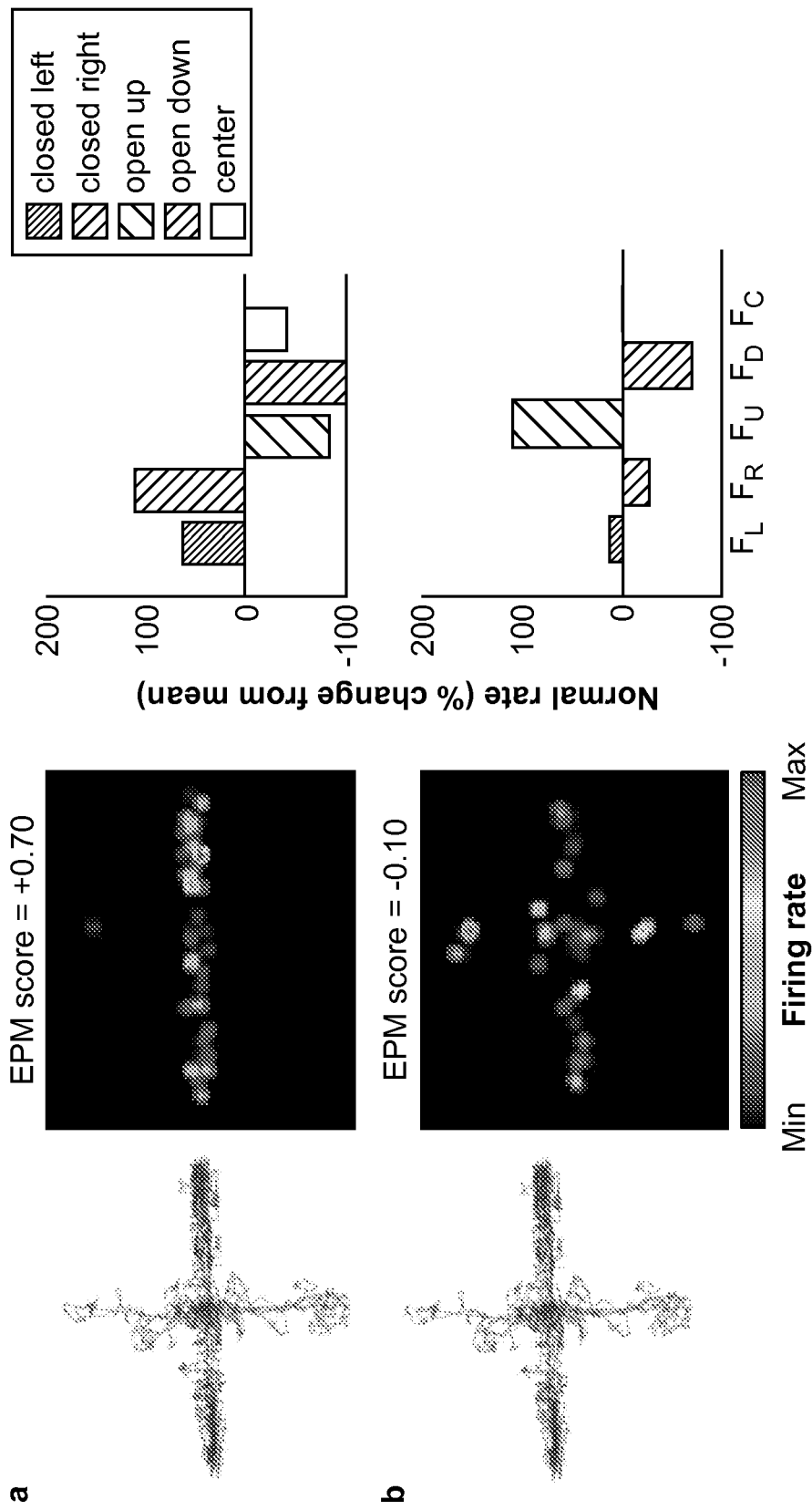
FIGS. 24A and 24B depict calculation of EPM scores to measure differentiation between closed and open arms by adBNST single units.

FIG. 23. adBNST multiunit activity is higher in the safe compartments of anxiety paradigms. Mice were implanted with a drivable microdrive containing 8 stereotrodes in the adBNST to allow recording of adBNST multiunit activity. Mice were run in the EPM (a-b) and the light-dark box (c-d). (a) Spatial firing rate map (left) and normalized firing rates (% difference from mean rate) from each arm are shown for a representative multiunit recording in the adBNST of a mouse exploring the EPM for 15 min. Note that activity is higher on both closed arms of the maze. Left: warmer colors correspond to higher firing rates. (b) Scatterplot showing rate in the closed arms and in the open arms for all multiunit recordings (n=32 multiunit recordings from 4 mice). Rates were significantly higher in closed arms (p<10-5, Wilcoxon signed-rank test). Note that adBNST multiunit activity from all channels in all mice was higher in the closed arms. Data were plotted as natural logarithm transforms of raw firing rates in Hz to allow for easier visualization. (c) Spatial firing rate map of a representative multiunit recording in the adBNST of a mouse exploring the light dark test for 15 minutes. Note that activity is higher in the dark compartment of the light-dark test box. The protrusion on the upper corner of the left chamber was caused by the position tracking LED reflecting off one of the walls. Warmer colors represent higher firing rates. (d) Histogram of multiunit firing rate in the dark compartment plotted as fold-increase from the light compartment. Note that the mean of this distribution is significantly higher than 1 (mean=1.16, p<0.005, Wilcoxon signed-rank test).

FIG. 24. Calculation of EPM scores to measure differentiation between closed and open arms by adBNST single units. Two representative single units from the same mouse were recorded simultaneously during a 15-min EPM exploration session. (a) Left panel: behavioral track showing the path taken by the mouse in the EPM. Middle panel: spatial firing rate map for a single unit that differentiated closed and open arms (higher rates are indicated by warmer colors). This unit was more active in the closed arms. Right panel: Bar graph showing normalized firing rates (plotted as % change from mean rate) for each sub-location in the EPM. Note that this unit fired more in both closed arms. The EPM score of this unit, which was calculated according to the formula below the figure, is displayed above its spatial firing rate map. FL, FR, FU, FD and FC indicate, respectively normalized firing rates (% change from mean rate) in the left arm, right arm, up arm, down arm and center of the EPM. (b) Same as (a), but for a single unit recorded in the same session that did not display task-related activity in the EPM. Note that although the unit fired differently in different arms, the unit did not consistently differentiate closed arms from open arms, resulting in a low EPM score (see Methods). In contrast, a high EPM score indicates that a unit has similar firing rates in arms of the same type and different firing rates in arms of different types. The unit in (a) has similar firing rates in arms of the same type, but closed and open rates are very different from each other.

FIG. 25. adBNST multiunit activity depends on BLA inputs to differentiate safe and aversive locations on the EPM. (a) Scatterplot of multiunit firing rates during yellow light OFF and ON epochs in eNpHR3.0:BLA-adBNST mice. (b) eNpHR3.0:BLA-adBNST mice were run in the EPM for 20 minutes with alternating 1-min laser-off and laser-on epochs (same experiment as FIG. 4). Inhibition of the BLA-adBNST projection decreased the EPM score of multiunit recordings (n=32 recordings, p<0.05, Wilcoxon signed-rank test), in agreement with single-unit data. Values are mean±s.e.m. (c) Scatterplot showing the distribution of EPM score changes. 25/32 recordings showed lower EPM scores in the light ON compared to the OFF epoch. EPM scores were significantly higher in the light OFF epoch (p<0.01, Wilcoxon signed-rank test). (d) The number of multiunit recordings with positive EPM scores also decreased with yellow light (p<0.05, Fisher's exact test).

FIG. 26. Inhibiting the BLA-adBNST projection decreases firing rates in the closed arms and EPM scores. eNpHR3.0:BLA-adBNST mice were run in the EPM for 20 minutes with alternating 1-min laser-off and laser-on epochs (same experiment as FIG. 4). (a) Inhibiting the BLA-adBNST projection tended to decrease firing rates of adBNST single units, but this effect did not reach statistical significance when pooling all neurons together (p<0.68, Wilcoxon's test, n=38 single units from 4 mice). (b) However, the adBNST single units that exhibited a significant decrease in firing rate during light ON epochs (n=20 out of 38 single units) displayed a significant decrease in rate in the closed arms (p<0.05, Wilcoxon signed-rank test), but not in the open arms (p<0.34, Wilcoxon signed-rank test). Significance of light-induced decreases in firing were tested by comparing rates across 10 one minute-long light OFF and 10 light ON epochs for each single unit. (c) Decreases in EPM scores were higher in adBNST single units with significant decreases in firing rate during light ON (n=38 for all cells, n=20 for cells with decreased firing in light ON, p<0.05, Wilcoxon signed rank test). Values are mean±s.e.m.

Figure 27:
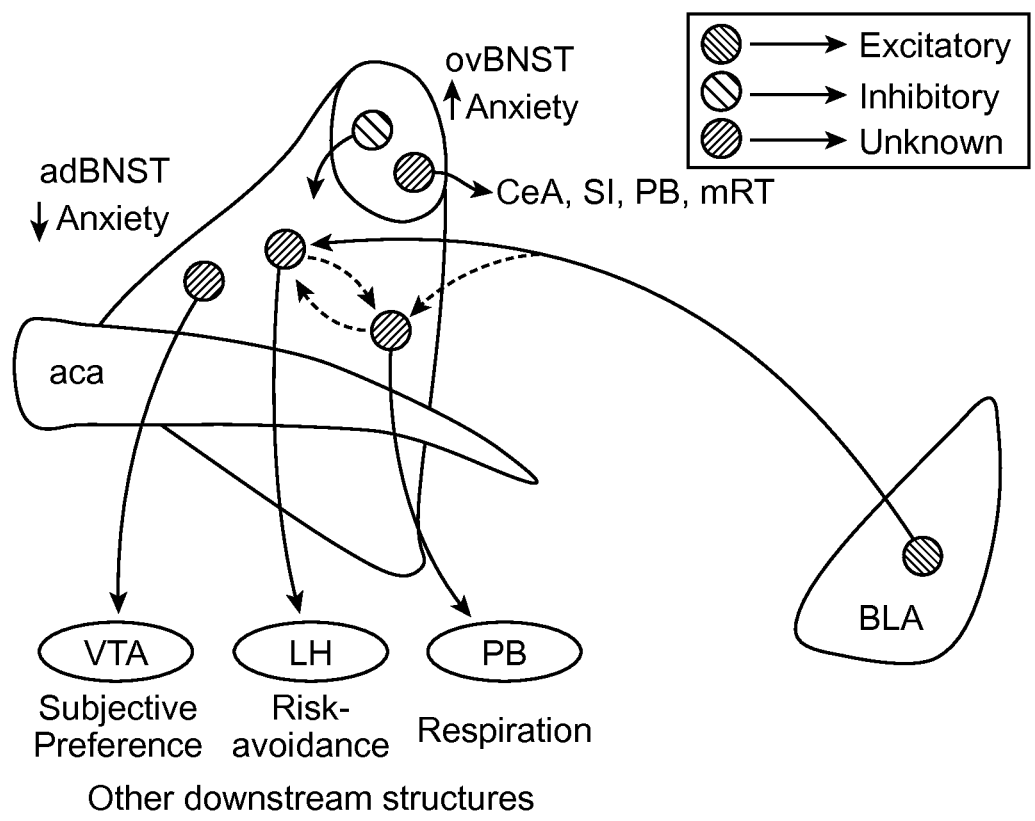
FIG. 27 schematically depicts a possible functional organization of BNST circuitry.

FIG. 27. Summary diagram. Schematic illustrating possible functional organization of BNST circuitry. The ovBNST inhibits the adBNST, whereas the adBNST sends only a weak projection to the ovBNST. The adBNST projects to the LH, PB and VTA. Each of these projections decreases distinct aspects of anxiety expression. The coordinated recruitment of these subpopulations may be implemented by recurrent circuitry in adBNST. BLA inputs likely recruits BNST output neurons to LH and PB, but not VTA in certain circumstances. The ovBNST may act to increase anxiety by inhibiting the adBNST or by independently influencing downstream structures, such as the central amygdala (CeA), substantia innominata (SI), PB or mesencephalic reticular formation (mRT). Red and blue arrows indicate excitatory and inhibitory projections, respectively. Purple arrows indicate projections with unknown neurotransmitter identity. Solid lines indicate the projections directly targeted and investigated in this study, and dashed lines indicate the projections suggested to exist by the data.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of reducing a feature of anxiety in a mammalian subject by inhibiting the activity of a bed nucleus of stria terminalis (BNST) neuron, a BNST subnucleus, or a neuronal output to or from a BNST neuron, said method comprising:
(i) administering directly into the BNST neuron or the BNST subnucleus of the mammalian subject, an effective amount of a recombinant viral vector comprising a nucleotide sequence encoding an inhibitory light-responsive opsin protein comprising: i) an amino acid sequence that is at least 95% identical to the amino acid sequence as set forth in SEQ ID NO: 1; ii) an ER export signal; and iii) a membrane trafficking signal, wherein the nucleotide sequence is operably linked to a neuron-specific promoter, wherein said administering provides for expression of the inhibitory light-responsive opsin protein in the BNST neuron or the BNST subnucleus;
(ii) implanting a light source into the brain of the mammalian subject around or near the BNST neuron or the BNST subnucleus; and
(iii) emitting light from the light source to activate the inhibitory light-responsive opsin protein in the BNST neuron or the BNST subnucleus,
wherein said emitting results in activation of the inhibitory light-responsive opsin protein expressed in the BNST neuron or the BNST subnucleus, resulting in a reduction of respiratory rate, risk avoidance, or aversion, thereby reducing anxiety and respiration rate.

2. The method of claim 1, wherein said reducing comprises inhibiting a BNST neuron, wherein said inhibiting is anxiolytic.

3. The method of claim 1, wherein said reducing comprises inhibiting the oval nucleus of a BNST, wherein said inhibiting is anxiolytic and reduces respiratory rate.

4. The method of claim 1, wherein the inhibitory light responsive protein comprises an amino acid sequence having at least about 98% amino acid sequence identity to the amino acid sequence set forth in SEQ ID NO:1.

5. The method of claim 1, wherein said emitting light from the light source comprises delivering light with a fiber optic light source.

6. The method of claim 1, wherein the inhibitory light-responsive protein comprises an amino acid sequence having at least 99% amino acid sequence identity to the amino acid sequence set forth in SEQ ID NO:1.

7. The method of claim 1, wherein the promoter is a synapsin-I promoter, a human synuclein 1 promoter, a human Thy1 promoter, or a calcium/calmodulin-dependent kinase II alpha (CAMKIIα) promoter.

8. The method of claim 1, wherein said administering is via stereotactic injection directly into the brain of the mammal.

9. The method of claim 1, wherein the ER export signal comprises the amino acid sequence selected from the group consisting of the amino acid sequences as set forth in SEQ ID NO: 24 and SEQ ID NO: 26.

10. The method of claim 1, wherein the membrane trafficking signal comprises the amino acid sequence as set forth in SEQ ID NO: 16.

* * * * *